US009775553B2

(12) United States Patent
Freeman et al.

(10) Patent No.: US 9,775,553 B2
(45) Date of Patent: Oct. 3, 2017

(54) METHOD AND APPARATUS FOR A FLUID SAMPLING DEVICE

(75) Inventors: Dominique Freeman, La Honda, CA (US); Tom Schulte, Redmond, WA (US); Michael Roger Caine, Toft (GB); Don Alden, Sunnyvale, CA (US); Matt Schumann, Toft (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 915 days.

(21) Appl. No.: 12/243,673

(22) Filed: Oct. 1, 2008

(65) Prior Publication Data
US 2009/0069716 A1 Mar. 12, 2009

Related U.S. Application Data

(63) Continuation-in-part of application No. 12/088,370, filed as application No. PCT/US2005/019445 on Jun. 3, 2005.
(Continued)

(51) Int. Cl.
*A61B 5/00* (2006.01)
*B65D 81/00* (2006.01)
(Continued)

(52) U.S. Cl.
CPC ............. *A61B 5/157* (2013.01); *A61B 5/151* (2013.01); *A61B 5/150022* (2013.01); *A61B 5/15113* (2013.01); *A61B 5/15117* (2013.01); *A61B 5/15123* (2013.01); *A61B 5/15128* (2013.01); *A61B 5/15132* (2013.01); *A61B 5/15151* (2013.01); *A61B 5/150152* (2013.01); *A61B 5/15161* (2013.01); *A61B 5/150167* (2013.01);
(Continued)

(58) Field of Classification Search
CPC ...................................................... A61B 5/00
USPC ............... 600/573, 575, 576, 583, 577, 578; 606/181, 1, 182; 3/573, 576, 577
See application file for complete search history.

(56) References Cited

U.S. PATENT DOCUMENTS 2,061 A 4/1841 Osdel ............................ 606/182
55,620 A 6/1866 Capewell ...................... 606/181
(Continued)

FOREIGN PATENT DOCUMENTS

CN 1946340 A 4/2007
DE 2206674 8/1972 ............. C07D 39/10
(Continued)

OTHER PUBLICATIONS

A. Bott, W. Heineman, Chronocoulometry, Current Separations, 2004, 20, pp. 121.
(Continued)

*Primary Examiner* — Jeffrey G Hoekstra
*Assistant Examiner* — May Abouelela
(74) *Attorney, Agent, or Firm* — Paul Davis; Beyer Law Group LLP

(57) ABSTRACT

A blood analyzer device has a housing with a top section coupled to a bottom section, a driver and a plurality of penetrating members housed in a disposable positionable in the housing. A gripper engages each penetrating member. A manually actuated button advances the disposable to move penetrating members into launch positions. A power is source coupled to the driver. A display is at the housing.

29 Claims, 36 Drawing Sheets

Related U.S. Application Data

(60) Provisional application No. 60/577,376, filed on Jun. 3, 2004, provisional application No. 60/577,412, filed on Jun. 3, 2004.

(51) Int. Cl.
*A61B 17/14* (2006.01)
*A61B 17/32* (2006.01)
*A61B 5/157* (2006.01)
*A61B 5/151* (2006.01)
*A61B 5/15* (2006.01)

(52) U.S. Cl.
CPC .. *A61B 5/150175* (2013.01); *A61B 5/150358* (2013.01); *A61B 5/150427* (2013.01); *A61B 5/150503* (2013.01); *A61B 5/150572* (2013.01)

(56) References Cited

U.S. PATENT DOCUMENTS

| | | | |
|---|---|---|---|
| 1,135,465 A | 4/1915 | Pollock | 606/181 |
| 1,733,847 A | 10/1929 | Wilmot | 292/332 |
| 2,258,857 A | 10/1941 | McCann | 601/81 |
| 2,628,319 A | 2/1953 | Vang | 310/15 |
| 2,714,890 A | 8/1955 | Alfred | 606/169 |
| 2,763,935 A | 9/1956 | Whaley | 33/511 |
| 2,801,633 A | 8/1957 | Ehrlich | 606/181 |
| 2,880,876 A | 4/1959 | Dujardin | 210/523 |
| 3,046,987 A | 7/1962 | Ehrlich | 128/314 |
| 3,030,959 A | 9/1962 | Grunert | 128/329 |
| 3,063,451 A | 11/1962 | Kowalk | 600/576 |
| 3,086,288 A | 4/1963 | Balamuth | 30/277.4 |
| 3,090,384 A | 5/1963 | Baldwin et al. | 604/272 |
| 3,208,452 A | 9/1965 | Stern | 606/182 |
| 3,358,689 A | 12/1967 | Higgins | 128/329 |
| 3,412,729 A | 11/1968 | Smith, Jr. | 128/2.05 |
| 3,424,154 A | 1/1969 | Kinsley | 604/70 |
| 3,448,307 A | 6/1969 | Rudolph | 310/23 |
| 3,494,358 A | 2/1970 | Grossenbacher | 128/218 |
| 3,607,097 A | 9/1971 | Auphan et al. | 422/66 |
| 3,620,209 A | 11/1971 | Kravitz | 601/79 |
| 3,626,929 A | 12/1971 | Sanz | 128/2 R |
| 3,628,026 A | 12/1971 | Cronin | 250/214.1 |
| 3,665,672 A | 5/1972 | Speelman | 53/435 |
| 3,673,475 A | 6/1972 | Britton | 318/122 |
| 3,712,292 A | 1/1973 | Zentmeyer, Jr. | 128/2 G |
| 3,712,293 A | 1/1973 | Mielke, Jr. | 128/2 |
| 3,734,812 A | 5/1973 | Yazawa | 428/107 |
| 3,742,954 A | 7/1973 | Strickland | 128/302 |
| 3,780,960 A | 12/1973 | Tokuno | 242/555.2 |
| 3,832,776 A | 9/1974 | Sawyer | 30/272 |
| 3,836,148 A | 9/1974 | Manning | 273/368 |
| 3,851,543 A | 12/1974 | Krom | 74/493 |
| 3,853,010 A | 12/1974 | Christen | 73/864.24 |
| 3,924,818 A | 12/1975 | Pfeifle | 242/364.7 |
| 3,938,526 A | 2/1976 | Anderson | 128/303.1 |
| 3,953,172 A | 4/1976 | Shapiro | 23/230 |
| 3,971,365 A | 7/1976 | Smith | 128/2.17 |
| 3,991,907 A * | 11/1976 | Kull | 221/84 |
| 4,057,394 A | 11/1977 | Genshaw | 23/230 |
| 4,077,200 A * | 3/1978 | Schneider | 368/69 |
| 4,077,406 A | 3/1978 | Sandhage | 604/61 |
| 4,109,655 A | 8/1978 | Chacornac | 128/253 |
| 4,139,011 A | 2/1979 | Benoit | 606/182 |
| 4,154,228 A | 5/1979 | Feldstein | 606/169 |
| 4,168,130 A | 9/1979 | Barth | 404/99 |
| 4,184,486 A | 1/1980 | Papa | 600/373 |
| 4,190,420 A | 2/1980 | Covington | 422/63 |
| 4,191,193 A | 3/1980 | Seo | 600/488 |
| 4,193,690 A | 3/1980 | Levenson | 356/301 |
| 4,203,446 A | 5/1980 | Hofert | 606/182 |
| 4,207,870 A | 6/1980 | Eldridge | 128/766 |
| 4,223,674 A | 9/1980 | Fluent | 604/504 |
| 4,224,125 A | 9/1980 | Nakamura | 204/195 B |
| 4,224,949 A | 9/1980 | Scott | 128/734 |
| 4,230,118 A | 10/1980 | Holman | 128/314 |
| 4,240,439 A | 12/1980 | Abe | 600/412 |
| 4,254,083 A | 3/1981 | Columbus | 422/55 |
| 4,258,001 A | 3/1981 | Pierce | 422/56 |
| 4,259,653 A | 3/1981 | McGonigal | 310/15 |
| 4,299,230 A | 11/1981 | Kubota | 600/300 |
| 4,301,412 A | 11/1981 | Hill | 324/442 |
| 4,321,397 A | 3/1982 | Nix | 548/366 |
| 4,340,669 A | 7/1982 | Bauer | 435/14 |
| 4,350,762 A | 9/1982 | De Luca | 435/10 |
| 4,353,984 A | 10/1982 | Yamada | 435/14 |
| 4,356,826 A | 11/1982 | Kubota | 600/300 |
| 4,360,016 A | 11/1982 | Sarrine | 128/763 |
| 4,388,922 A | 6/1983 | Telang | 604/319 |
| 4,391,905 A | 7/1983 | Bauer | 435/14 |
| 4,391,906 A | 7/1983 | Bauer | 435/14 |
| 4,392,933 A | 7/1983 | Nakamura | 204/403.14 |
| 4,394,512 A | 7/1983 | Batz | 548/365 |
| 4,397,556 A | 8/1983 | Muller | 356/301 |
| 4,407,008 A | 9/1983 | Schmidt | 356/301 |
| 4,411,266 A | 10/1983 | Cosman | 128/303.18 |
| 4,414,975 A | 11/1983 | Ryder | 128/314 |
| 4,418,037 A | 11/1983 | Katsuyama | 422/56 |
| 4,425,039 A | 1/1984 | Grant | 356/35.5 |
| 4,426,451 A | 1/1984 | Columbus | 436/518 |
| 4,426,884 A | 1/1984 | Polchaninoff | 73/172 |
| 4,440,301 A | 4/1984 | Intengan | 206/456 |
| 4,442,836 A | 4/1984 | Meinecke | 128/314 |
| 4,442,972 A | 4/1984 | Sahay | 236/1 EA |
| 4,449,529 A | 5/1984 | Burns | 606/182 |
| 4,462,405 A | 7/1984 | Ehrlich | 606/182 |
| 4,469,110 A | 9/1984 | Slama | 128/770 |
| 4,490,139 A | 12/1984 | Huizenga et al. | 604/57 |
| 4,517,978 A | 5/1985 | Levin | 128/314 |
| 4,518,384 A | 5/1985 | Tarello | 604/61 |
| 4,523,994 A | 6/1985 | Shono | 549/352 |
| 4,525,164 A | 6/1985 | Loeb et al. | |
| 4,535,769 A | 8/1985 | Burns | 128/314 |
| 4,535,773 A | 8/1985 | Yoon | 606/185 |
| 4,537,197 A | 8/1985 | Hulka | 128/633 |
| 4,539,988 A | 9/1985 | Shirley | 128/314 |
| 4,545,382 A | 10/1985 | Higgins | 128/635 |
| 4,553,541 A | 11/1985 | Burns | 128/314 |
| 4,561,445 A | 12/1985 | Berke | 128/642 |
| 4,577,630 A | 3/1986 | Nitzsche | 128/314 |
| 4,580,564 A | 4/1986 | Andersen | 502/8 |
| 4,580,565 A | 4/1986 | Cornell | 128/314 |
| 4,586,819 A | 5/1986 | Tochigi | 356/301 |
| 4,586,926 A | 5/1986 | Osborne | 604/272 |
| 4,595,479 A | 6/1986 | Kimura | 204/294 |
| 4,600,014 A | 7/1986 | Beraha | 128/754 |
| 4,603,209 A | 7/1986 | Tsien | 549/352 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,627,445 A | 12/1986 | Garcia | 600/583 |
| 4,628,929 A * | 12/1986 | Intengan | A61B 5/1411 606/182 |
| 4,637,403 A | 1/1987 | Garcia | 600/583 |
| 4,643,189 A | 2/1987 | Mintz | 128/314 |
| 4,648,408 A | 3/1987 | Hutcheson | 128/770 |
| 4,648,714 A | 3/1987 | Benner | 356/301 |
| 4,653,511 A | 3/1987 | Goch | 128/763 |
| 4,653,513 A | 3/1987 | Dombrowski | 600/578 |
| 4,655,225 A | 4/1987 | Dahne | 600/316 |
| 4,661,768 A | 4/1987 | Carusillo | 324/678 |
| 4,666,438 A | 5/1987 | Raulerson | 604/272 |
| 4,676,244 A | 6/1987 | Enstrom | 128/314 |
| 4,677,979 A | 7/1987 | Burns | 128/314 |
| 4,678,277 A | 7/1987 | Delhaye | 356/301 |
| 4,682,892 A | 7/1987 | Chawla | 356/353 |
| 4,695,273 A | 9/1987 | Brown | |
| 4,702,594 A | 10/1987 | Grant | 356/35.5 |
| 4,711,245 A | 12/1987 | Higgins | 128/635 |
| 4,712,460 A | 12/1987 | Allen | 83/208 |
| 4,712,548 A | 12/1987 | Enstrom | 128/314 |

(56) References Cited

U.S. PATENT DOCUMENTS

| | | | |
|---|---|---|---|
| 4,714,462 A | 12/1987 | DiDomenico | 604/67 |
| 4,715,374 A | 12/1987 | Maggio | 128/314 |
| 4,731,330 A | 3/1988 | Hill | 436/16 |
| 4,731,726 A | 3/1988 | Allen, III | 600/300 |
| 4,734,360 A | 3/1988 | Phillips | 435/25 |
| 4,735,203 A | 4/1988 | Ryder | 128/314 |
| 4,737,458 A | 4/1988 | Batz | 435/28 |
| 4,750,489 A | 6/1988 | Berkman | 606/166 |
| 4,753,776 A | 6/1988 | Hillman | 422/101 |
| 4,756,884 A | 7/1988 | Hillman | 422/73 |
| 4,757,022 A | 7/1988 | Shults | 204/403.05 |
| 4,774,192 A | 9/1988 | Teriniello | 436/530 |
| 4,784,486 A | 11/1988 | Van Wagenen | 356/301 |
| 4,787,398 A | 11/1988 | Garcia | 600/583 |
| 4,790,979 A | 12/1988 | Terminiello | 422/56 |
| 4,794,926 A | 1/1989 | Munsch | 606/183 |
| 4,797,283 A | 1/1989 | Allen | 424/443 |
| 4,814,142 A | 3/1989 | Gleisner | 422/56 |
| 4,814,661 A | 3/1989 | Ratzlaff | 310/328 |
| 4,817,603 A | 4/1989 | Turner | 606/182 |
| 4,818,493 A | 4/1989 | Coville | 422/102 |
| 4,820,010 A | 4/1989 | Sciefres | 385/43 |
| 4,820,399 A | 4/1989 | Senda et al. | 204/403 |
| 4,823,806 A | 4/1989 | Bajada | 600/557 |
| 4,824,639 A | 4/1989 | Hildenbrand | 422/56 |
| RE32,922 E | 5/1989 | Levin | 128/314 |
| 4,825,711 A | 5/1989 | Jensen | 73/865.8 |
| 4,827,763 A | 5/1989 | Bourland | 73/172 |
| 4,829,011 A | 5/1989 | Gibbons | 436/512 |
| 4,830,959 A | 5/1989 | McNeill | 435/53 |
| 4,836,904 A | 6/1989 | Armstron | 204/294 |
| 4,840,893 A | 6/1989 | Hill | 435/6 |
| 4,844,095 A | 7/1989 | Chiodo | 128/314 |
| 4,845,392 A | 7/1989 | Mumbower | 310/14 |
| 4,850,973 A | 7/1989 | Jordan | 604/157 |
| 4,857,274 A | 8/1989 | Simon | 422/74 |
| 4,868,129 A | 9/1989 | Gibbons | 436/179 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,877,026 A | 10/1989 | de Laforcade | 128/305 |
| 4,882,013 A | 11/1989 | Turner | 204/1 |
| 4,883,055 A | 11/1989 | Merrick | 128/633 |
| 4,883,068 A | 11/1989 | Dechow | 128/760 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,895,156 A | 1/1990 | Schulze | 600/342 |
| 4,897,173 A | 1/1990 | Nankai | 204/403 |
| 4,900,424 A | 2/1990 | Birch | 204/409 |
| 4,900,666 A | 2/1990 | Phillips | 435/25 |
| 4,911,794 A | 3/1990 | Parce | 204/1 T |
| 4,920,977 A | 5/1990 | Haynes | 128/770 |
| 4,924,879 A | 5/1990 | O'brien | 600/583 |
| 4,935,346 A | 6/1990 | Phillips | 435/14 |
| 4,938,218 A | 7/1990 | Goodman | 128/633 |
| 4,940,468 A | 7/1990 | Petillo | 606/170 |
| 4,944,304 A | 7/1990 | Nishina | 128/667 |
| 4,945,045 A | 7/1990 | Forrest | 435/25 |
| 4,946,795 A | 8/1990 | Gibbons | 436/179 |
| 4,948,727 A | 8/1990 | Cass | 435/18 |
| 4,948,961 A | 8/1990 | Hillman | 250/252.1 |
| 4,952,373 A | 8/1990 | Sugarman | 422/99 |
| 4,952,515 A | 8/1990 | Gleisner | 436/169 |
| 4,953,552 A | 9/1990 | DeMarzo | 128/635 |
| 4,953,976 A | 9/1990 | Adler-Golden | 356/301 |
| 4,963,498 A | 10/1990 | Hillman | 436/69 |
| 4,966,581 A | 10/1990 | Landau | 604/72 |
| 4,966,646 A | 10/1990 | Zdeblick | 156/633 |
| 4,966,671 A | 10/1990 | Nylander | 204/153.14 |
| 4,975,581 A | 12/1990 | Robinson | 250/339 |
| 4,976,724 A | 12/1990 | Nieto | 606/182 |
| 4,977,910 A | 12/1990 | Miyahara | 134/7 |
| 4,983,178 A | 1/1991 | Schnell | 606/181 |
| 4,984,085 A | 1/1991 | Landowski | 358/213 |
| 4,990,154 A | 2/1991 | Brown | 606/182 |
| 4,995,402 A | 2/1991 | Smith | 600/584 |
| 5,001,054 A | 3/1991 | Wagner | 435/14 |
| 5,001,873 A | 3/1991 | Rufin | 451/39 |
| 5,004,923 A | 4/1991 | Hillman | 250/341 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,026,388 A | 6/1991 | Ingalz | 606/182 |
| D318,331 S | 7/1991 | Phillips | D24/169 |
| 5,028,142 A | 7/1991 | Ostoich | 366/273 |
| 5,029,583 A | 7/1991 | Meserol | 600/316 |
| 5,035,704 A | 7/1991 | Lambert | 606/182 |
| 5,039,617 A | 8/1991 | McDonald | 436/69 |
| 5,043,143 A | 8/1991 | Shaw | 422/65 |
| 5,046,496 A | 9/1991 | Betts | 600/352 |
| 5,047,044 A | 9/1991 | Smith | 606/182 |
| 5,049,487 A | 9/1991 | Phillips | 435/4 |
| 5,049,673 A | 9/1991 | Tsien | 549/352 |
| 5,054,487 A | 10/1991 | Clarke | 128/633 |
| 5,054,499 A | 10/1991 | Swierczek | 128/770 |
| 5,057,082 A | 10/1991 | Burchette, Jr. | 604/164 |
| 5,057,277 A | 10/1991 | Mauze | 422/56 |
| 5,059,394 A | 10/1991 | Phillips | 422/68.1 |
| 5,059,789 A | 10/1991 | Salcudean | 250/206.1 |
| 5,060,174 A | 10/1991 | Gross | 702/139 |
| 5,062,898 A | 11/1991 | McDermott | 134/7 |
| 5,064,411 A | 11/1991 | Gordon, III | 604/48 |
| 5,070,874 A | 12/1991 | Barnes | 128/633 |
| 5,070,886 A | 12/1991 | Mitchen | 128/771 |
| 5,073,500 A | 12/1991 | Saito et al. | 436/53 |
| 5,074,872 A | 12/1991 | Brown | 606/182 |
| 5,077,017 A | 12/1991 | Gorin | 422/100 |
| 5,077,199 A | 12/1991 | Basagni | 435/14 |
| 5,080,865 A | 1/1992 | Leiner | 422/68.1 |
| 5,086,229 A | 2/1992 | Rosenthal | 250/341 |
| 5,089,112 A | 2/1992 | Skotheim | 204/403 |
| 5,092,842 A | 3/1992 | Bechtold | 604/135 |
| 5,094,943 A | 3/1992 | Siedel | 435/25 |
| 5,096,669 A | 3/1992 | Lauks | 204/403.02 |
| 5,097,810 A | 3/1992 | Fishman | 600/556 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,382 A | 4/1992 | Brinkerhoff et al. | 604/164.12 |
| 5,104,619 A | 4/1992 | Castro et al. | 422/56 |
| 5,104,813 A | 4/1992 | Besemer | 436/179 |
| 5,107,764 A | 4/1992 | Gasparrini | 101/425 |
| 5,108,564 A | 4/1992 | Szuminsky | 204/153.12 |
| 5,108,889 A * | 4/1992 | Smith et al. | 435/4 |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter | 204/403 |
| 5,128,015 A | 7/1992 | Szuminsky | 204/403 |
| 5,128,171 A | 7/1992 | Gleisner | 427/2 |
| 5,132,801 A | 7/1992 | Yamano | 358/213 |
| 5,133,730 A | 7/1992 | Biro | 606/182 |
| 5,135,719 A | 8/1992 | Hillman | 422/101 |
| 5,139,685 A | 8/1992 | Castro | 210/767 |
| 5,140,161 A | 8/1992 | Hillman | 250/341 |
| 5,141,868 A | 8/1992 | Shanks | 435/288 |
| 5,144,139 A | 9/1992 | Hillman | 250/341 |
| 5,145,565 A | 9/1992 | Kater | 600/341 |
| 5,146,091 A | 9/1992 | Knudson | 250/341.6 |
| 5,152,296 A | 10/1992 | Simons | 128/670 |
| 5,152,775 A | 10/1992 | Ruppert | 606/182 |
| 5,153,671 A | 10/1992 | Miles | 356/301 |
| 5,156,611 A | 10/1992 | Haynes | 606/181 |
| 5,162,525 A | 11/1992 | Masilamani | 549/352 |
| 5,163,442 A | 11/1992 | Ono | 128/760 |
| 5,164,598 A | 11/1992 | Hillman | 250/341 |
| 5,167,619 A | 12/1992 | Wuchinich | 604/22 |
| 5,170,364 A | 12/1992 | Gross | 702/139 |
| 5,174,726 A | 12/1992 | Findlay | 417/205 |
| D332,490 S | 1/1993 | Brown | D24/146 |
| 5,179,005 A | 1/1993 | Phillips | 435/14 |
| 5,185,256 A | 2/1993 | Nankai | 435/174 |
| 5,187,100 A | 2/1993 | Matzinger | 436/16 |

(56) References Cited

U.S. PATENT DOCUMENTS

| | | | |
|---|---|---|---|
| 5,188,118 A | 2/1993 | Terwilliger | 600/566 |
| 5,189,751 A | 3/1993 | Giuliani | 15/22.1 |
| 5,192,415 A | 3/1993 | Yoshioka | 204/403 |
| 5,194,391 A | 3/1993 | Mauze | 436/166 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,208,163 A | 5/1993 | Charlton et al. | 436/63 |
| 5,209,028 A | 5/1993 | McDermott | 51/426 |
| 5,211,652 A | 5/1993 | Derbyshire | 606/182 |
| 5,212,879 A | 5/1993 | Biro | 29/437 |
| 5,215,587 A | 6/1993 | McConnellogue | 118/699 |
| 5,217,476 A | 6/1993 | Wishinsky | 606/167 |
| 5,217,480 A | 6/1993 | Haber | 606/182 |
| 5,218,966 A | 6/1993 | Yamasawa | 600/499 |
| 5,222,504 A | 6/1993 | Solomon | 600/557 |
| 5,229,282 A | 7/1993 | Yoshioka | 435/177 |
| 5,230,866 A | 7/1993 | Shartle | 422/103 |
| 5,231,993 A | 8/1993 | Haber | 128/770 |
| 5,241,969 A | 9/1993 | Carson | 600/566 |
| 5,247,932 A | 9/1993 | Chung | 128/633 |
| 5,249,583 A | 10/1993 | Mallaby | 600/567 |
| 5,250,066 A | 10/1993 | Lambert | 606/181 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |
| 5,266,179 A | 11/1993 | Nankai | 204/401 |
| 5,266,359 A | 11/1993 | Spielvogel | 427/388.4 |
| D342,573 S | 12/1993 | Cerola | D24/147 |
| 5,267,974 A | 12/1993 | Lambert | 604/195 |
| 5,272,087 A | 12/1993 | El Murr | 435/291 |
| 5,279,294 A | 1/1994 | Anderson | 600/322 |
| 5,279,791 A | 1/1994 | Aldrich | 422/58 |
| 5,282,822 A | 2/1994 | Macors | 606/182 |
| 5,286,362 A | 2/1994 | Hoenes | 204/403 |
| 5,286,364 A | 2/1994 | Yacynych | 204/418 |
| 5,288,636 A | 2/1994 | Pollmann | 435/288 |
| 5,294,261 A | 3/1994 | McDermott | 134/7 |
| 5,296,378 A | 3/1994 | Sakata | 436/63 |
| 5,300,779 A | 4/1994 | Hillman | 250/341 |
| 5,304,192 A | 4/1994 | Crouse | 606/181 |
| 5,304,193 A | 4/1994 | Zhadanov | 606/182 |
| 5,304,347 A | 4/1994 | Mann | 422/67 |
| 5,304,468 A | 4/1994 | Phillips | 435/14 |
| 5,306,623 A | 4/1994 | Kiser | 435/14 |
| 5,307,263 A | 4/1994 | Brown | 600/301 |
| 5,312,590 A | 5/1994 | Gunasingham | 422/56 |
| 5,314,441 A | 5/1994 | Cusack | 606/182 |
| 5,314,442 A | 5/1994 | Morita | 606/182 |
| 5,315,793 A | 5/1994 | Peterson | 451/2 |
| 5,316,012 A | 5/1994 | Siegal | 128/744 |
| 5,316,229 A | 5/1994 | Draghetti | 606/171 |
| 5,318,583 A | 6/1994 | Rabenau | 606/182 |
| 5,318,584 A | 6/1994 | Lange | 606/182 |
| 5,320,607 A | 6/1994 | Ishibashi | 604/115 |
| 5,320,808 A | 6/1994 | Holen | 422/64 |
| 5,324,302 A | 6/1994 | Crouse | 606/181 |
| 5,324,303 A | 6/1994 | Strong | 606/181 |
| 5,330,634 A | 7/1994 | Wong | 205/777.5 |
| 5,332,479 A | 7/1994 | Uenoyama | 204/153.12 |
| 5,341,206 A | 8/1994 | Pittaro | 356/301 |
| 5,342,382 A | 8/1994 | Brinkerhoff | 606/182 |
| 5,344,703 A | 9/1994 | Kovar | 428/312.6 |
| 5,350,392 A | 9/1994 | Purcell | 606/182 |
| 5,354,287 A | 10/1994 | Wacks | 604/232 |
| 5,354,447 A | 10/1994 | Uenoyama | 204/403 |
| 5,356,420 A | 10/1994 | Czernecki | 606/182 |
| 5,360,410 A | 11/1994 | Wacks | 604/232 |
| 5,365,699 A | 11/1994 | Armstrong | 451/7 |
| 5,366,469 A | 11/1994 | Steg | 606/182 |
| 5,366,470 A | 11/1994 | Ramel | 606/183 |
| 5,366,609 A | 11/1994 | White | 204/403 |
| 5,368,047 A | 11/1994 | Suzuki | 600/578 |
| 5,370,509 A | 12/1994 | Golding | 417/423.1 |
| 5,372,135 A | 12/1994 | Mendelson | 600/322 |
| 5,375,397 A | 12/1994 | Ferrand | 54/66 |
| 5,378,628 A | 1/1995 | Graetzel | 435/288 |
| 5,382,346 A | 1/1995 | Uenoyama | 204/403 |
| 5,383,885 A | 1/1995 | Bland | 606/182 |
| 5,389,534 A | 2/1995 | Gentzkow | 435/180 |
| 5,390,450 A | 2/1995 | Goenka | 451/39 |
| 5,393,903 A | 2/1995 | Gratzel | 556/137 |
| 5,395,339 A | 3/1995 | Talonn | 604/111 |
| 5,395,387 A | 3/1995 | Burns | 606/181 |
| 5,397,334 A | 3/1995 | Schenk | 606/182 |
| 5,401,376 A | 3/1995 | Foos | 204/415 |
| 5,402,798 A | 4/1995 | Swierczek | 128/770 |
| 5,405,283 A | 4/1995 | Goenka | 451/39 |
| 5,405,510 A | 4/1995 | Betts | 205/782 |
| 5,407,545 A | 4/1995 | Hirose | 204/153.12 |
| 5,407,554 A | 4/1995 | Saurer | 204/403 |
| 5,407,818 A | 4/1995 | Gentzkow | 435/180 |
| 5,409,583 A | 4/1995 | Yoshioka | 204/153.12 |
| 5,409,664 A | 4/1995 | Allen | 422/56 |
| 5,410,059 A | 4/1995 | Fraser | 546/10 |
| 5,410,474 A | 4/1995 | Fox | 600/300 |
| 5,415,169 A | 5/1995 | Siczek | 600/427 |
| 5,418,142 A | 5/1995 | Kiser | 435/14 |
| 5,423,847 A | 6/1995 | Strong | 606/182 |
| 5,424,545 A | 6/1995 | Block | 350/343 |
| 5,426,032 A | 6/1995 | Phillips | 435/14 |
| 5,436,161 A | 7/1995 | Bergstrom | 435/291 |
| 5,437,999 A | 8/1995 | Diebold | 435/288 |
| 5,443,701 A | 8/1995 | Willner | 204/153 |
| 5,445,920 A | 8/1995 | Saito | 430/311 |
| D362,719 S | 9/1995 | Kaplan | D24/147 |
| 5,453,360 A | 9/1995 | Yu | 435/28 |
| 5,454,828 A | 10/1995 | Schraga | 606/181 |
| 5,456,875 A | 10/1995 | Lambert | 264/328.1 |
| 5,459,325 A | 10/1995 | Hueton | 250/458.1 |
| 5,460,182 A | 10/1995 | Goodman | 600/342 |
| 5,462,533 A | 10/1995 | Daugherty | 604/164 |
| 5,464,418 A | 11/1995 | Schraga | 606/182 |
| 5,465,722 A | 11/1995 | Fort | 600/447 |
| 5,471,102 A | 11/1995 | Becker | 310/50 |
| 5,472,427 A | 12/1995 | Rammler | 604/164.01 |
| 5,474,084 A | 12/1995 | Cunniff | 600/557 |
| 5,476,474 A | 12/1995 | Davis | 606/182 |
| 5,480,387 A | 1/1996 | Gabriel | 604/134 |
| 5,487,748 A | 1/1996 | Marshall | 606/182 |
| D367,109 S | 2/1996 | Ryner | D24/224 |
| 5,490,505 A | 2/1996 | Diab | 600/323 |
| 5,496,274 A | 3/1996 | Graves | 604/86 |
| 5,496,453 A | 3/1996 | Uenoyama | 205/777.5 |
| 5,498,542 A | 3/1996 | Corey | 435/283.1 |
| 5,501,836 A | 3/1996 | Myerson | 42/57 |
| 5,501,893 A | 3/1996 | Laermer | 428/161 |
| 5,507,629 A | 4/1996 | Jarvik | 417/423.3 |
| 5,509,410 A | 4/1996 | Hill | 128/637 |
| 5,510,266 A | 4/1996 | Bonner | 436/43 |
| 5,512,159 A | 4/1996 | Yoshioka | 204/403 |
| 5,514,152 A | 5/1996 | Smith | 606/182 |
| 5,515,170 A | 5/1996 | Matzinger | 356/423 |
| 5,518,006 A | 5/1996 | Mawhirt | 128/770 |
| D371,198 S | 6/1996 | Savage | D24/169 |
| 5,524,636 A | 6/1996 | Sarvazyan | 128/774 |
| 5,525,511 A | 6/1996 | D'Costa | 435/287.9 |
| 5,525,518 A | 6/1996 | Lundsgaard | 436/68 |
| 5,526,120 A | 6/1996 | Jina | 356/446 |
| 5,527,333 A | 6/1996 | Nikkels | 606/182 |
| 5,527,334 A | 6/1996 | Kanner | 606/182 |
| 5,529,074 A | 6/1996 | Greenfield | 600/557 |
| 5,540,676 A | 7/1996 | Freiberg | 606/3 |
| 5,540,709 A | 7/1996 | Ramel | 606/183 |
| 5,543,326 A | 8/1996 | Heller | 435/287.9 |
| 5,545,174 A | 8/1996 | Schenk | 606/182 |
| 5,545,291 A | 8/1996 | Smith | 438/107 |
| 5,547,702 A | 8/1996 | Gleisner | 427/2.13 |
| D373,419 S | 9/1996 | Muramatsu | D24/165 |
| 5,554,153 A | 9/1996 | Costello | 606/9 |
| 5,554,166 A | 9/1996 | Lange | 606/182 |
| 5,558,834 A | 9/1996 | Chu | 422/55 |

(56) References Cited

U.S. PATENT DOCUMENTS

| | | | |
|---|---|---|---|
| 5,562,384 A | 10/1996 | Alvite | 414/226.01 |
| 5,562,696 A | 10/1996 | Nobles | 606/185 |
| 5,563,031 A | 10/1996 | Yu | 435/4 |
| 5,563,042 A | 10/1996 | Phillips | 435/14 |
| 5,569,286 A | 10/1996 | Peckham | 606/181 |
| 5,569,287 A | 10/1996 | Tezuka | 606/182 |
| 5,571,132 A | 11/1996 | Mawhirt | 606/182 |
| 5,575,284 A | 11/1996 | Athan | 600/323 |
| 5,575,403 A | 11/1996 | Charlton | 221/31 |
| 5,575,895 A | 11/1996 | Ikeda | 204/403 |
| 5,582,697 A | 12/1996 | Ikeda | 204/403 |
| 5,584,846 A | 12/1996 | Mawhirt | 606/181 |
| 5,591,139 A | 1/1997 | Lin | 604/264 |
| 5,593,852 A | 1/1997 | Heller | 435/14 |
| 5,599,501 A | 2/1997 | Carey | 422/64 |
| 5,605,837 A | 2/1997 | Karimi | 436/14 |
| D378,612 S | 3/1997 | Clark | D24/169 |
| 5,608,006 A | 3/1997 | Myerson | 525/54.1 |
| 5,609,749 A | 3/1997 | Yamauchi | 205/777.5 |
| 5,611,809 A | 3/1997 | Marshall | 606/181 |
| 5,611,810 A | 3/1997 | Arnold | 606/185 |
| 5,613,978 A | 3/1997 | Harding | 606/181 |
| 5,616,135 A | 4/1997 | Thorne | 604/192 |
| 5,617,851 A | 4/1997 | Lipkovker | 600/573 |
| 5,618,297 A | 4/1997 | Hart | 606/185 |
| 5,620,579 A | 4/1997 | Genshaw | 204/402 |
| 5,620,863 A | 4/1997 | Tomasco | 435/14 |
| 5,624,458 A | 4/1997 | Lipscher | 606/181 |
| 5,624,459 A | 4/1997 | Kortenbach | 606/185 |
| 5,624,537 A | 4/1997 | Turner | 204/403 |
| D379,516 S | 5/1997 | Rutter | D24/146 |
| 5,628,764 A | 5/1997 | Schraga | 606/182 |
| 5,628,765 A | 5/1997 | Morita | 606/182 |
| 5,628,890 A | 5/1997 | Carter | 204/403.5 |
| 5,628,961 A | 5/1997 | Davis | 422/63 |
| 5,630,828 A | 5/1997 | Mawhirt | 606/167 |
| 5,630,986 A | 5/1997 | Charlton | 422/64 |
| 5,632,410 A | 5/1997 | Moulton | 221/79 |
| D381,591 S | 7/1997 | Rice | D10/81 |
| 5,643,306 A | 7/1997 | Schraga | 606/182 |
| 5,643,308 A | 7/1997 | Markman | 606/187 |
| 5,645,555 A | 7/1997 | Davis | 606/182 |
| 5,647,851 A | 7/1997 | Pokras | 604/131 |
| 5,650,062 A | 7/1997 | Ikeda | 205/778 |
| 5,653,863 A | 8/1997 | Genshaw | 205/777.5 |
| 5,657,760 A | 8/1997 | Ying | 128/660.03 |
| 5,658,444 A | 8/1997 | Black | 204/415 |
| 5,660,791 A | 8/1997 | Brenneman | 422/58 |
| D383,550 S | 9/1997 | Larson | D24/225 |
| 5,662,127 A | 9/1997 | De Vaughn | 128/765 |
| 5,662,672 A | 9/1997 | Pambianchi | 606/181 |
| 5,666,966 A | 9/1997 | Horie | 128/760 |
| 5,678,306 A | 10/1997 | Bozeman | 29/888.025 |
| 5,680,872 A | 10/1997 | Sesekura | 128/760 |
| 5,682,233 A | 10/1997 | Brinda | 356/246 |
| 5,682,884 A | 11/1997 | Hill | 128/637 |
| 5,683,562 A | 11/1997 | Schaffar | 204/403 |
| 5,691,898 A | 11/1997 | Rosenberg | 700/85 |
| 5,692,514 A | 12/1997 | Bowman | 600/504 |
| 5,695,947 A | 12/1997 | Guo | 435/11 |
| 5,700,695 A | 12/1997 | Yassinzadeh | 436/180 |
| 5,705,045 A | 1/1998 | Park | 204/403 |
| 5,707,384 A | 1/1998 | Kim | 606/181 |
| 5,708,247 A | 1/1998 | McAleer | 204/403 |
| 5,709,668 A | 1/1998 | Wacks | 604/232 |
| 5,710,011 A | 1/1998 | Forrow | 435/25 |
| 5,714,123 A | 2/1998 | Sohrab | 422/99 |
| 5,714,390 A | 2/1998 | Hallowitz | 436/526 |
| 5,719,034 A | 2/1998 | Kiser | 435/14 |
| 5,720,862 A | 2/1998 | Hamamoto | 204/403 |
| 5,720,924 A | 2/1998 | Eikmeier | 422/102 |
| D392,391 S | 3/1998 | Douglas | D24/225 |
| D392,740 S | 3/1998 | Yung | D24/169 |
| 5,723,284 A | 3/1998 | Ye | 435/4 |
| 5,727,548 A | 3/1998 | Hill | 128/637 |
| 5,729,905 A | 3/1998 | Mathiasmeier | 33/3 R |
| 5,730,753 A | 3/1998 | Morita | 606/181 |
| 5,733,085 A | 3/1998 | Shida | 411/442 |
| 5,733,300 A | 3/1998 | Pambianchi | 606/181 |
| D393,716 S | 4/1998 | Brenneman | D24/147 |
| D393,717 S | 4/1998 | Brenneman | D24/147 |
| 5,735,868 A | 4/1998 | Lee | 606/189 |
| 5,736,103 A | 4/1998 | Pugh | 422/68.1 |
| 5,738,244 A | 4/1998 | Charlton | 221/26 |
| 5,741,634 A | 4/1998 | Nozoe | 435/4 |
| RE35,803 E | 5/1998 | Lange | 606/182 |
| 5,746,217 A | 5/1998 | Erickson | 128/760 |
| 5,746,761 A | 5/1998 | Turchin | 606/181 |
| 5,753,429 A | 5/1998 | Pugh | 435/4 |
| 5,753,452 A | 5/1998 | Smith | 435/14 |
| 5,755,228 A | 5/1998 | Wilson | 600/459 |
| 5,755,733 A | 5/1998 | Morita | 606/182 |
| 5,758,643 A | 6/1998 | Wong | 600/309 |
| 5,759,364 A | 6/1998 | Charlton | 204/403 |
| 5,762,770 A | 6/1998 | Pritchard | 204/403 |
| 5,770,086 A | 6/1998 | Indriksons | 210/643 |
| 5,770,369 A | 6/1998 | Meade | 435/6 |
| 5,772,586 A | 6/1998 | Heinonen | 600/300 |
| 5,772,677 A | 6/1998 | Mawhirt | 606/181 |
| 5,773,270 A | 6/1998 | D'Orazio | 435/177 |
| 5,776,157 A | 7/1998 | Thorne | 606/182 |
| 5,776,719 A | 7/1998 | Douglas | 435/28 |
| 5,779,365 A | 7/1998 | Takaki | 374/161 |
| 5,780,304 A | 7/1998 | Matzinger | 436/169 |
| 5,782,770 A | 7/1998 | Mooradian | 600/476 |
| 5,782,852 A | 7/1998 | Foggia | 606/182 |
| 5,788,651 A | 8/1998 | Weilandt | 600/567 |
| 5,788,652 A | 8/1998 | Rahn | 600/577 |
| 5,789,255 A | 8/1998 | Yu | 536/95 |
| 5,795,725 A | 8/1998 | Buechler | 435/7.1 |
| 5,795,774 A | 8/1998 | Matsumoto | 435/287.9 |
| 5,797,940 A | 8/1998 | Mawhirt | 606/167 |
| 5,797,942 A | 8/1998 | Schraga | 606/182 |
| 5,798,030 A | 8/1998 | Raguse | 204/403 |
| 5,798,031 A | 8/1998 | Charlton | 204/403 |
| 5,800,781 A | 9/1998 | Gavin | 422/73 |
| 5,801,057 A | 9/1998 | Smart | 436/68 |
| 5,810,199 A | 9/1998 | Charlton | 221/31 |
| D399,566 S | 10/1998 | Sohrab | D24/169 |
| 5,820,551 A | 10/1998 | Hill | 600/347 |
| 5,823,973 A | 10/1998 | Racchini | 600/573 |
| 5,824,491 A | 10/1998 | Priest | 435/28 |
| 5,827,181 A | 10/1998 | Dias | 600/322 |
| 5,829,589 A | 11/1998 | Nguyen | 206/366 |
| 5,830,219 A | 11/1998 | Bird | 606/130 |
| 5,840,020 A | 11/1998 | Heinonen | 600/309 |
| 5,840,171 A | 11/1998 | Birch | 205/335 |
| 5,843,691 A | 12/1998 | Douglas | 435/14 |
| 5,843,692 A | 12/1998 | Phillips | 435/14 |
| 5,846,216 A | 12/1998 | Gonzales | 604/2 |
| 5,846,486 A | 12/1998 | Pugh | 422/56 |
| 5,846,490 A | 12/1998 | Yokota | 422/66 |
| 5,849,174 A | 12/1998 | Sanghera | 205/775 |
| 5,854,074 A | 12/1998 | Charlton | 436/46 |
| D403,975 S | 1/1999 | Douglas | D10/81 |
| 5,855,377 A | 1/1999 | Murphy | 279/50 |
| 5,855,801 A | 1/1999 | Lin | 216/2 |
| 5,856,174 A | 1/1999 | Lipshutz | 435/286.5 |
| 5,856,195 A | 1/1999 | Charlton | 436/50 |
| 5,857,967 A | 1/1999 | Frid | 600/301 |
| 5,857,983 A | 1/1999 | Douglas | 600/538 |
| 5,858,804 A | 1/1999 | Zanzucchi | 506/9 |
| 5,860,922 A | 1/1999 | Gordon | 600/431 |
| 5,863,800 A | 1/1999 | Eikmeier | 436/48 |
| 5,866,353 A | 2/1999 | Berneth | 435/26 |
| 5,868,772 A | 2/1999 | LeVaughn | 606/181 |
| 5,869,972 A | 2/1999 | Birch | 324/439 |
| 5,871,494 A | 2/1999 | Simons | 606/181 |
| 5,872,713 A | 2/1999 | Douglas | 702/85 |
| 5,873,856 A | 2/1999 | Hjertman et al. | |
| 5,873,887 A | 2/1999 | King | 606/182 |
| 5,876,351 A | 3/1999 | Rohde | 600/523 |
| 5,876,957 A | 3/1999 | Douglas | 435/28 |
| 5,879,311 A | 3/1999 | Duchon | 600/583 |

(56) References Cited

U.S. PATENT DOCUMENTS

| | | | | |
|---|---|---|---|---|
| 5,879,373 A | 3/1999 | Roeper | | 606/344 |
| 5,880,829 A | 3/1999 | Kauhaniemi | | 356/246 |
| 5,882,494 A | 3/1999 | van Antwerp | | 204/403 |
| 5,886,056 A | 3/1999 | Hershkowitz | | 518/703 |
| 5,890,128 A | 3/1999 | Diaz | | 705/2 |
| 5,891,053 A | 4/1999 | Sesekura | | 600/583 |
| 5,892,569 A | 4/1999 | Van de Velde | | 351/221 |
| 5,893,848 A | 4/1999 | Negus | | 606/41 |
| 5,897,569 A | 4/1999 | Kellogg | | 606/169 |
| 5,899,915 A | 5/1999 | Saadat | | 606/170 |
| 5,900,130 A | 5/1999 | Benvegnu | | 204/453 |
| 5,902,731 A | 5/1999 | Ouyang | | 435/26 |
| 5,906,921 A | 5/1999 | Ikeda | | 435/25 |
| D411,619 S | 6/1999 | Duchon | | D24/146 |
| 5,908,416 A | 6/1999 | Costello | | 606/9 |
| 5,911,937 A | 6/1999 | Hekal | | 264/255 |
| 5,912,134 A | 6/1999 | Shartle | | 435/7.24 |
| 5,916,156 A | 6/1999 | Hildenbrand | | 600/347 |
| 5,916,229 A | 6/1999 | Evans | | 606/171 |
| 5,916,230 A | 6/1999 | Brenneman | | 606/172 |
| 5,919,711 A | 7/1999 | Boyd | | 436/178 |
| 5,921,963 A | 7/1999 | Erez | | 604/192 |
| 5,922,188 A | 7/1999 | Ikeda | | 204/777.5 |
| 5,922,530 A | 7/1999 | Yu | | 435/4 |
| 5,922,591 A | 7/1999 | Anderson | | 435/287.2 |
| RE36,268 E | 8/1999 | Szuminsky | | 205/777.5 |
| 5,931,794 A | 8/1999 | Pitesky | | 600/556 |
| 5,935,075 A | 8/1999 | Casscells | | 600/474 |
| 5,938,635 A | 8/1999 | Kuhle | | 604/506 |
| 5,938,679 A | 8/1999 | Freeman | | 606/181 |
| 5,940,153 A | 8/1999 | Castaneda | | 349/3 |
| 5,942,189 A | 8/1999 | Wolfbeis | | 422/82.08 |
| 5,947,957 A | 9/1999 | Morris | | 606/13 |
| 5,951,492 A | 9/1999 | Douglas | | 600/583 |
| 5,951,493 A | 9/1999 | Douglas | | 600/583 |
| 5,951,582 A | 9/1999 | Thorne | | 606/182 |
| 5,951,836 A | 9/1999 | McAleer | | 204/403 |
| 5,954,738 A | 9/1999 | LeVaughn | | 606/181 |
| 5,957,846 A | 9/1999 | Chiang | | 600/447 |
| 5,958,199 A | 9/1999 | Miyamoto | | 204/403 |
| 5,959,098 A | 9/1999 | Goldberg | | 536/25.3 |
| 5,961,451 A | 10/1999 | Reber | | 600/322 |
| 5,965,380 A | 10/1999 | Heller | | 435/14 |
| 5,968,063 A | 10/1999 | Chu | | 606/185 |
| 5,968,760 A | 10/1999 | Phillips | | 435/14 |
| 5,968,836 A | 10/1999 | Matzinger | | 436/169 |
| 5,971,941 A * | 10/1999 | Simons et al. | | 600/573 |
| 5,972,199 A | 10/1999 | Heller | | 205/777.5 |
| 5,972,294 A | 10/1999 | Smith | | 422/58 |
| 5,976,085 A | 11/1999 | Kimball | | 600/309 |
| 5,983,193 A | 11/1999 | Heinonen | | 705/2 |
| 5,985,116 A | 11/1999 | Ikeda | | 204/403 |
| 5,986,754 A | 11/1999 | Harding | | 356/246 |
| 5,993,400 A | 11/1999 | Rincoe | | 600/595 |
| 5,993,434 A | 11/1999 | Dev | | 604/501 |
| D417,504 S | 12/1999 | Love | | D24/169 |
| 5,997,509 A | 12/1999 | Rosengart et al. | | |
| 5,997,561 A | 12/1999 | Boecker | | 606/182 |
| 5,997,817 A | 12/1999 | Crismore | | 422/58 |
| 5,997,818 A | 12/1999 | Hackner | | 422/681 |
| 6,001,067 A | 12/1999 | Shults | | 600/584 |
| 6,007,497 A | 12/1999 | Huitema | | 600/567 |
| D418,602 S | 1/2000 | Prokop | | D24/169 |
| 6,014,577 A | 1/2000 | Henning | | 600/345 |
| 6,018,289 A | 1/2000 | Sekura | | 340/309.4 |
| 6,020,110 A | 2/2000 | William | | 430/315 |
| 6,022,324 A | 2/2000 | Skinner | | 600/566 |
| 6,022,366 A | 2/2000 | Schraga | | 606/181 |
| 6,022,748 A | 2/2000 | Charych | | 436/527 |
| 6,023,629 A | 2/2000 | Tamada | | 600/347 |
| 6,027,459 A | 2/2000 | Shain | | 600/573 |
| 6,030,399 A | 2/2000 | Ignotz | | 606/167 |
| 6,030,827 A | 2/2000 | Davis | | 435/287 |
| 6,030,967 A | 2/2000 | Marui | | 514/215 |
| 6,032,059 A | 2/2000 | Henning | | 600/345 |
| 6,033,421 A | 3/2000 | Theiss | | 606/186 |
| 6,033,866 A | 3/2000 | Guo | | 435/14 |
| 6,036,924 A * | 3/2000 | Simons et al. | | 600/583 |
| 6,037,178 A | 3/2000 | Leiner | | 436/50 |
| 6,045,567 A | 4/2000 | Taylor | | 606/181 |
| 6,046,055 A | 4/2000 | Wolfbeis | | 436/172 |
| D424,696 S | 5/2000 | Ray | | D24/169 |
| 6,059,815 A | 5/2000 | Lee | | 606/209 |
| 6,060,327 A | 5/2000 | Keen | | 436/518 |
| 6,063,039 A | 5/2000 | Cunningham | | 600/573 |
| 6,066,243 A | 5/2000 | Anderson | | 422/82.01 |
| 6,066,296 A | 5/2000 | Brady | | 422/63 |
| 6,067,463 A | 5/2000 | Jeng | | 600/336 |
| D426,638 S | 6/2000 | Ray | | D24/169 |
| 6,070,761 A | 6/2000 | Bloom | | 222/81 |
| 6,071,249 A | 6/2000 | Cunningham | | 600/578 |
| 6,071,250 A | 6/2000 | Douglas | | 600/583 |
| 6,071,251 A | 6/2000 | Cunningham | | 600/584 |
| 6,071,294 A * | 6/2000 | Simons et al. | | 606/181 |
| 6,071,391 A | 6/2000 | Gotoh | | 204/403 |
| 6,074,360 A | 6/2000 | Haar | | 604/57 |
| 6,077,408 A | 6/2000 | Miyamoto | | 204/403 |
| 6,080,106 A | 6/2000 | Lloyd | | 600/300 |
| 6,080,172 A | 6/2000 | Fujiwara | | 606/166 |
| D428,150 S | 7/2000 | Ruf | | D24/146 |
| 6,083,196 A | 7/2000 | Trautman | | 604/46 |
| 6,083,710 A | 7/2000 | Heller | | 435/14 |
| 6,084,660 A | 7/2000 | Shartle | | 356/39 |
| 6,085,576 A | 7/2000 | Sunshine | | 73/29.01 |
| 6,086,544 A | 7/2000 | Hibner | | 600/568 |
| 6,086,562 A | 7/2000 | Jacobsen | | 604/156 |
| 6,090,078 A | 7/2000 | Erskine | | 604/198 |
| 6,091,975 A | 7/2000 | Daddona | | 600/345 |
| 6,093,156 A | 7/2000 | Cunningham | | 600/573 |
| D428,993 S | 8/2000 | Lubs | | D24/165 |
| 6,099,484 A | 8/2000 | Douglas | | 600/583 |
| 6,099,802 A | 8/2000 | Pugh | | 422/58 |
| 6,100,107 A | 8/2000 | Lei | | 438/50 |
| 6,102,933 A | 8/2000 | Lee | | 606/209 |
| 6,103,033 A | 8/2000 | Say | | 156/73.1 |
| 6,103,509 A | 8/2000 | Sode | | 435/190 |
| 6,104,940 A | 8/2000 | Watanabe | | 600/345 |
| 6,106,751 A | 8/2000 | Talbot | | 264/81 |
| 6,107,083 A | 8/2000 | Collins | | 435/288 |
| 6,117,115 A | 9/2000 | Hill et al. | | 606/189 |
| 6,117,630 A | 9/2000 | Reber | | 435/4 |
| 6,118,126 A | 9/2000 | Zanzucchi | | 250/458.1 |
| 6,119,033 A | 9/2000 | Spigelman | | 600/426 |
| 6,120,462 A | 9/2000 | Hibner | | 600/566 |
| 6,120,676 A | 9/2000 | Heller | | 205/777.5 |
| 6,121,009 A | 9/2000 | Heller | | 435/14 |
| 6,126,804 A | 10/2000 | Andresen | | 204/601 |
| 6,126,899 A | 10/2000 | Woudenberg | | 422/50 |
| 6,129,823 A | 10/2000 | Hughes | | 204/403.01 |
| 6,132,449 A | 10/2000 | Lum | | 606/181 |
| 6,133,837 A | 10/2000 | Riley | | 340/573.1 |
| 6,134,461 A | 10/2000 | Say | | 600/345 |
| 6,136,013 A | 10/2000 | Marshall | | 606/167 |
| 6,139,562 A | 10/2000 | Mauze | | 606/171 |
| 6,143,164 A | 11/2000 | Heller | | 600/583 |
| 6,144,976 A | 11/2000 | Silva et al. | | 708/100 |
| 6,149,203 A | 11/2000 | Hanlon | | 283/72 |
| 6,152,875 A | 11/2000 | Hakamata | | 600/319 |
| 6,152,942 A | 11/2000 | Brenneman | | 606/181 |
| 6,153,069 A | 11/2000 | Pottgen | | 204/403 |
| RE36,991 E | 12/2000 | Yamamoto | | 204/403 |
| 6,155,992 A | 12/2000 | Henning | | 600/583 |
| 6,156,051 A | 12/2000 | Schraga | | 606/181 |
| 6,157,442 A | 12/2000 | Raskas | | 356/39 |
| 6,159,147 A | 12/2000 | Lichter | | 600/300 |
| 6,159,424 A | 12/2000 | Kauhaniemi | | 422/63 |
| 6,162,397 A | 12/2000 | Jurik | | 422/56 |
| 6,162,611 A | 12/2000 | Heller | | 435/14 |
| 6,168,957 B1 | 1/2001 | Matzinger | | 436/518 |
| 6,171,325 B1 | 1/2001 | Mauze | | 606/171 |
| 6,172,743 B1 | 1/2001 | Kley et al. | | 356/39 |
| 6,175,752 B1 | 1/2001 | Say | | 600/345 |
| 6,176,847 B1 | 1/2001 | Humphreys | | 604/246 |
| 6,176,865 B1 | 1/2001 | Mauze | | 606/171 |

(56) References Cited

U.S. PATENT DOCUMENTS

| | | | |
|---|---|---|---|
| 6,177,000 B1 | 1/2001 | Peterson | 205/777.5 |
| 6,177,931 B1 | 1/2001 | Alexander | 725/52 |
| 6,183,489 B1 | 2/2001 | Douglas | 606/181 |
| 6,190,612 B1 | 2/2001 | Berger | 422/82.07 |
| 6,191,852 B1 | 2/2001 | Paffhausen | 356/244 |
| 6,192,891 B1 | 2/2001 | Gravel | 128/920 |
| 6,193,673 B1 | 2/2001 | Viola | 600/568 |
| 6,193,873 B1 | 2/2001 | Ohara | 205/792 |
| 6,194,900 B1 | 2/2001 | Freeman | 324/321 |
| 6,197,040 B1 | 3/2001 | LeVaughn | 606/182 |
| 6,197,257 B1 | 3/2001 | Raskas | 422/82.05 |
| 6,200,289 B1 * | 3/2001 | Hochman et al. | 604/67 |
| 6,200,773 B1 | 3/2001 | Ouyang | 435/26 |
| 6,203,504 B1 * | 3/2001 | Latterell | A61B 5/150389 600/576 |
| 6,206,841 B1 | 3/2001 | Cunningham et al. | 600/584 |
| 6,210,133 B1 | 4/2001 | Aboul-Hosn | 417/423.1 |
| 6,210,369 B1 | 4/2001 | Wilmot | 604/157 |
| 6,210,420 B1 | 4/2001 | Mauze | 606/182 |
| 6,210,421 B1 | 4/2001 | Bocker | 606/182 |
| 6,212,417 B1 | 4/2001 | Ikeda | 204/403.14 |
| 6,214,626 B1 | 4/2001 | Meller | 436/165 |
| 6,214,804 B1 | 4/2001 | Felgner | 514/44 |
| 6,218,571 B1 | 4/2001 | Zheng | 562/61 |
| 6,219,574 B1 | 4/2001 | Cormier | 604/20 |
| 6,221,023 B1 | 4/2001 | Matsuba | |
| 6,221,238 B1 | 4/2001 | Grundig | 205/777.5 |
| 6,224,617 B1 | 5/2001 | Saadat et al. | 606/170 |
| 6,225,078 B1 | 5/2001 | Ikeda | 435/25 |
| 6,228,100 B1 | 5/2001 | Schraga | 606/183 |
| 6,230,051 B1 | 5/2001 | Cormier | 604/20 |
| 6,230,501 B1 | 5/2001 | Bailey | 62/51.1 |
| 6,231,531 B1 | 5/2001 | Lum | 601/46 |
| 6,234,772 B1 | 5/2001 | Wampler | 417/423.12 |
| D444,235 S | 6/2001 | Roberts | D24/169 |
| 6,241,862 B1 | 6/2001 | McAleer | 204/403 |
| 6,242,207 B1 | 6/2001 | Douglas | 435/25 |
| 6,245,060 B1 | 6/2001 | Loomis | 606/9 |
| 6,245,215 B1 | 6/2001 | Douglas | 205/775 |
| 6,251,083 B1 | 6/2001 | Yum | 600/584 |
| 6,251,121 B1 | 6/2001 | Saadat | |
| 6,251,260 B1 | 6/2001 | Heller | 205/777.5 |
| 6,251,344 B1 | 6/2001 | Goldstein | 422/123 |
| D444,557 S | 7/2001 | Levaughn | D24/146 |
| 6,254,831 B1 | 7/2001 | Barnard | 422/82.08 |
| 6,256,533 B1 | 7/2001 | Yuzhakov | 604/21 |
| 6,258,111 B1 | 7/2001 | Ross | 606/171 |
| 6,258,229 B1 | 7/2001 | Winarta | 204/403 |
| 6,258,254 B1 | 7/2001 | Miyamoto | 205/777.5 |
| 6,261,241 B1 | 7/2001 | Burbank | 600/564 |
| 6,261,245 B1 | 7/2001 | Kawai | 600/576 |
| 6,261,519 B1 | 7/2001 | Harding | 422/58 |
| 6,264,635 B1 | 7/2001 | Wampler | 604/151 |
| 6,268,161 B1 | 7/2001 | Han | 435/14 |
| 6,268,162 B1 | 7/2001 | Phillips | 435/14 |
| 6,269,314 B1 | 7/2001 | Iitawaki | 702/23 |
| 6,270,637 B1 | 8/2001 | Crismore | 204/403 |
| 6,272,359 B1 | 8/2001 | Kivela | 455/567 |
| 6,272,364 B1 | 8/2001 | Kurnik | 600/345 |
| 6,275,717 B1 | 8/2001 | Gross | 600/345 |
| 6,280,254 B1 | 8/2001 | Wu | 439/630 |
| 6,281,006 B1 | 8/2001 | Heller | 435/287.9 |
| 6,283,926 B1 | 9/2001 | Cunningham | 600/573 |
| 6,283,982 B1 | 9/2001 | Levaughn | 606/172 |
| 6,284,478 B1 | 9/2001 | Heller | 435/14 |
| 6,285,448 B1 | 9/2001 | Kuenstner | 356/39 |
| 6,285,454 B1 | 9/2001 | Douglas | 356/446 |
| 6,289,254 B1 | 9/2001 | Shimizu | 700/96 |
| 6,290,683 B1 | 9/2001 | Erez | 604/273 |
| 6,295,506 B1 | 9/2001 | Heinonen | 702/104 |
| 6,299,578 B1 | 10/2001 | Kurnik | 600/309 |
| 6,299,596 B1 | 10/2001 | Ding | 604/96.01 |
| 6,299,757 B1 | 10/2001 | Feldman | 205/775 |
| 6,302,855 B1 | 10/2001 | Lav | 600/584 |
| 6,306,104 B1 | 10/2001 | Cunningham | 600/573 |
| 6,306,152 B1 | 10/2001 | Verdonk | 606/182 |
| 6,306,347 B1 | 10/2001 | Mason | 422/58 |
| 6,309,351 B1 | 10/2001 | Kurnik | 600/309 |
| 6,309,370 B1 | 10/2001 | Haim et al. | |
| 6,309,535 B1 | 10/2001 | Williams | 205/777.5 |
| 6,312,612 B1 | 11/2001 | Sherman | 216/2 |
| 6,315,738 B1 | 11/2001 | Nishikawa | 600/583 |
| 6,318,970 B1 | 11/2001 | Backhouse | 417/92 |
| 6,319,210 B1 | 11/2001 | Douglas | 600/583 |
| 6,322,574 B1 | 11/2001 | Lloyd | 606/181 |
| 6,322,808 B1 | 11/2001 | Trautman | 424/448 |
| 6,322,963 B1 | 11/2001 | Bauer | 435/4 |
| 6,331,163 B1 | 12/2001 | Kaplan | 600/486 |
| 6,332,871 B1 * | 12/2001 | Douglas et al. | 600/583 |
| 6,334,363 B1 | 1/2002 | Testud | 73/862 |
| 6,334,856 B1 | 1/2002 | Allen | 604/191 |
| 6,335,203 B1 | 1/2002 | Patel | 436/169 |
| 6,336,900 B1 | 1/2002 | Alleckson | 600/485 |
| 6,338,790 B1 | 1/2002 | Feldman | 205/777.5 |
| 6,346,120 B1 | 2/2002 | Yamazaki | 623/3.13 |
| 6,350,273 B1 | 2/2002 | Minagawa | 606/186 |
| 6,350,451 B1 | 2/2002 | Horn | 424/184.1 |
| 6,352,514 B1 | 3/2002 | Douglas | 600/583 |
| 6,352,523 B1 | 3/2002 | Brown | 604/207 |
| 6,353,753 B1 | 3/2002 | Flock | 600/473 |
| 6,358,196 B1 | 3/2002 | Rayman | |
| 6,364,889 B1 * | 4/2002 | Kheiri et al. | 606/181 |
| 6,364,890 B1 | 4/2002 | Lum | 606/181 |
| 6,375,626 B1 | 4/2002 | Allen et al. | 600/584 |
| 6,375,627 B1 | 4/2002 | Mauze | 600/584 |
| 6,379,301 B1 | 4/2002 | WOrthington | 600/309 |
| 6,379,317 B1 | 4/2002 | Kintzig | 600/573 |
| 6,379,324 B1 | 4/2002 | Gartstein | 604/22 |
| 6,379,969 B1 | 4/2002 | Mauze | 436/68 |
| D456,910 S | 5/2002 | Clark | D24/225 |
| 6,387,709 B1 | 5/2002 | Mason | 436/164 |
| 6,391,005 B1 | 5/2002 | Lum | 604/117 |
| 6,395,227 B1 | 5/2002 | Kiser | 422/56 |
| 6,398,522 B2 | 6/2002 | Skill | 417/410.3 |
| 6,398,562 B1 | 6/2002 | Butler | 439/91 |
| 6,399,394 B1 | 6/2002 | Dahm | 436/180 |
| 6,402,701 B1 | 6/2002 | Kaplan | 600/567 |
| 6,402,704 B1 | 6/2002 | Mcmorrow | 600/576 |
| 6,409,740 B1 | 6/2002 | Kuhr | 606/182 |
| 6,413,410 B1 | 7/2002 | Hodges | 205/775 |
| 6,413,411 B1 | 7/2002 | Pottgen | 205/777.5 |
| 6,415,821 B2 | 7/2002 | Kamholz | 137/827 |
| 6,419,661 B1 | 7/2002 | Kuhr et al. | |
| 6,420,128 B1 | 7/2002 | Ouyang | 435/14 |
| 6,421,633 B1 | 7/2002 | Heinonen | 703/11 |
| 6,423,014 B1 | 7/2002 | Churchill | 600/587 |
| 6,428,664 B1 | 8/2002 | Bhullar | 204/403.03 |
| 6,436,055 B1 | 8/2002 | Roe | 600/584 |
| 6,436,256 B1 | 8/2002 | Williams | 204/403.06 |
| 6,436,721 B1 | 8/2002 | Kuo | 436/514 |
| 6,440,645 B1 | 8/2002 | Yon-Hin | 430/322 |
| 6,444,115 B1 | 9/2002 | Hodges | 205/792 |
| 6,447,119 B1 | 9/2002 | Stewart et al. | 351/212 |
| 6,447,265 B1 | 9/2002 | Antaki | 417/354 |
| 6,451,040 B1 | 9/2002 | Purcell | 606/181 |
| 6,453,810 B1 | 9/2002 | Rossmeisl | 101/123 |
| 6,458,258 B2 | 10/2002 | Taniike | 204/403 |
| 6,461,496 B1 | 10/2002 | Feldman | 205/777.5 |
| 6,462,162 B2 | 10/2002 | van Antwerp | 528/77 |
| 6,471,903 B2 | 10/2002 | Sherman | 264/328.1 |
| 6,472,220 B1 | 10/2002 | Simons | |
| 6,475,360 B1 | 11/2002 | Hodges | 204/403.14 |
| 6,475,372 B1 | 11/2002 | Ohara | 205/777.5 |
| 6,475,436 B1 | 11/2002 | Schabbach | 422/64 |
| 6,475,750 B1 | 11/2002 | Han | 435/14 |
| 6,484,046 B1 | 11/2002 | Say | 600/345 |
| 6,485,439 B1 | 11/2002 | Roe | 600/578 |
| 6,485,461 B1 | 11/2002 | Mason | 604/132 |
| 6,485,923 B1 | 11/2002 | Yani | 435/14 |
| 6,488,827 B1 | 12/2002 | Shartle | 204/403 |
| 6,488,872 B1 | 12/2002 | Beebe et al. | 264/31 |
| 6,488,891 B2 | 12/2002 | Mason | 422/58 |
| 6,489,133 B2 | 12/2002 | Phillips | 435/14 |
| 6,491,709 B2 | 12/2002 | Sharma | 606/181 |

(56) References Cited

U.S. PATENT DOCUMENTS

| | | | |
|---|---|---|---|
| 6,491,870 B2 | 12/2002 | Patel | 422/58 |
| 6,497,845 B1 | 12/2002 | Sacherer | 422/104 |
| 6,501,404 B2 | 12/2002 | Walker | 341/143 |
| 6,501,976 B1 | 12/2002 | Sohrab | 600/347 |
| 6,503,209 B2 | 1/2003 | Hakky et al. | |
| 6,503,210 B1 | 1/2003 | Hirao | 600/576 |
| 6,503,231 B1 | 1/2003 | Prausnitz | 604/272 |
| 6,503,290 B1 | 1/2003 | Jarosinski | 75/252 |
| 6,506,165 B1 | 1/2003 | Sweeney | 600/562 |
| 6,506,168 B1 | 1/2003 | Fathallah | 600/578 |
| 6,506,575 B1 | 1/2003 | Knappe | 435/25 |
| 6,508,785 B1 | 1/2003 | Eppstein | 604/113 |
| 6,512,986 B1 | 1/2003 | Harmon | 702/84 |
| 6,514,270 B1 | 2/2003 | Schraga | 606/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,521,110 B1 | 2/2003 | Hodges | 204/403.14 |
| 6,521,182 B1 | 2/2003 | Shartle | 422/58 |
| 6,527,521 B2 | 3/2003 | Noda | 417/355 |
| 6,527,716 B1 | 3/2003 | Epstein | 600/309 |
| 6,527,778 B2 | 3/2003 | Athanasiou | 606/80 |
| 6,529,377 B1 | 3/2003 | Nelson | 361/699 |
| 6,530,892 B1 | 3/2003 | Kelly | 600/583 |
| 6,530,937 B1 | 3/2003 | Schraga | 606/182 |
| 6,531,322 B1 | 3/2003 | Jurik | 436/95 |
| 6,533,949 B1 | 3/2003 | Yeshurun | 216/11 |
| 6,537,242 B1 | 3/2003 | Palmer | 604/22 |
| 6,537,264 B1 | 3/2003 | Cormier et al. | 604/506 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,547,954 B2 | 4/2003 | Ikeda | 205/777.5 |
| 6,549,796 B2 | 4/2003 | Sohrab | 600/345 |
| 6,551,494 B1 | 4/2003 | Heller | 205/777.5 |
| 6,555,061 B1 | 4/2003 | Leong | 422/58 |
| D475,136 S | 5/2003 | Taniguchi | D24/165 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,561,989 B2 | 5/2003 | Whitson | 600/573 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,572,822 B2 | 6/2003 | Jurik | 422/56 |
| 6,574,490 B2 | 6/2003 | Abbink | 600/316 |
| 6,576,101 B1 | 6/2003 | Heller | 204/403.1 |
| 6,576,416 B2 | 6/2003 | Haviland | 435/4 |
| 6,579,690 B1 | 6/2003 | Bonnecaze | 435/14 |
| 6,584,338 B1 | 6/2003 | Van Muiswinkel | 600/419 |
| D477,670 S | 7/2003 | Jurik | D24/225 |
| 6,586,199 B2 | 7/2003 | Ouyang | 435/26 |
| 6,587,705 B1 | 7/2003 | Kim | 600/347 |
| 6,589,260 B1 | 7/2003 | Schmelzeisen | 606/181 |
| 6,589,261 B1 | 7/2003 | Abulhaj | 606/181 |
| 6,591,124 B2 | 7/2003 | Sherman | 600/345 |
| 6,591,125 B1 | 7/2003 | Buse | 600/347 |
| 6,592,744 B1 | 7/2003 | Hodges | 205/775 |
| 6,592,745 B1 | 7/2003 | Feldman | 205/777.5 |
| 6,599,281 B1 | 7/2003 | Struys et al. | |
| 6,599,407 B2 | 7/2003 | Taniike | 204/403.1 |
| 6,599,693 B1 | 7/2003 | Webb | 435/4 |
| 6,599,769 B2 | 7/2003 | Kondo | 438/28 |
| 6,601,534 B2 | 8/2003 | Hebrank | 119/6.8 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,607,362 B2 | 8/2003 | Lum | 417/53 |
| 6,607,658 B1 | 8/2003 | Heller | 205/777.5 |
| 6,612,111 B1 | 9/2003 | Hodges | 60/593 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,620,310 B1 | 9/2003 | Ohara | 205/792 |
| 6,623,501 B2 | 9/2003 | Heller | 606/181 |
| 6,626,851 B2 | 9/2003 | Hirao | 600/576 |
| 6,632,349 B1 | 10/2003 | Hodges | 205/792 |
| 6,635,222 B2 | 10/2003 | Kent | 422/22 |
| 6,638,415 B1 | 10/2003 | Hodges | 205/775 |
| 6,641,533 B2 | 11/2003 | Causey | 600/300 |
| 6,645,368 B1 | 11/2003 | Beaty | 205/792 |
| 6,649,416 B1 | 11/2003 | Kauer | 436/164 |
| 6,652,720 B1 | 11/2003 | Mansouri | 204/403.11 |
| 6,652,734 B1 | 11/2003 | Hodges | 205/777.5 |
| 6,652,814 B1 | 11/2003 | House | 422/104 |
| D484,600 S | 12/2003 | Kaar | D24/169 |
| 6,656,428 B1 | 12/2003 | Clark et al. | 422/404 |
| 6,656,697 B1 | 12/2003 | Ouyang | 435/7.9 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,662,439 B1 | 12/2003 | Bhullar | 29/825 |
| 6,669,669 B2 | 12/2003 | Flaherty | 604/132 |
| 6,671,527 B2 | 12/2003 | Peterson | 600/316 |
| D484,980 S | 1/2004 | Hartwein | D24/165 |
| 6,673,617 B2 | 1/2004 | Patel | 436/8 |
| 6,676,995 B2 | 1/2004 | Dick | 427/286 |
| 6,679,841 B2 | 1/2004 | Bojan | 600/309 |
| 6,679,852 B1 | 1/2004 | Schmelzeisen | 600/583 |
| 6,682,933 B2 | 1/2004 | Patel | 436/8 |
| 6,689,411 B2 | 2/2004 | Dick | 427/2.13 |
| 6,706,000 B2 | 3/2004 | Perez | 600/583 |
| 6,706,159 B2 | 3/2004 | Moerman | 204/403.03 |
| 6,706,232 B2 | 3/2004 | Hasegawa | 264/403.09 |
| 6,709,692 B2 | 3/2004 | Sudor | 427/2.1 |
| 6,713,660 B1 | 3/2004 | Roe | 604/361 |
| 6,716,577 B1 | 4/2004 | Yu | 435/6 |
| 6,719,887 B2 | 4/2004 | Hasegawa | 204/403.09 |
| 6,719,923 B2 | 4/2004 | Stiene | 252/511 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,729,546 B2 | 5/2004 | Roustaei | 235/462.45 |
| 6,730,494 B1 | 5/2004 | Toranto | 435/28 |
| 6,731,966 B1 | 5/2004 | Spigelman | 600/407 |
| 6,733,493 B2 | 5/2004 | Gruzdev | 606/9 |
| 6,736,777 B2 | 5/2004 | Kim | 600/365 |
| 6,738,654 B2 | 5/2004 | Sohrab | 600/345 |
| 6,740,215 B1 | 5/2004 | Yamamoto | 204/403.14 |
| 6,743,211 B1 | 6/2004 | PraUSnitz | 604/239 |
| 6,743,597 B1 | 6/2004 | Guo | 435/14 |
| 6,746,872 B2 | 6/2004 | Zheng | 436/16 |
| 6,749,740 B2 | 6/2004 | Liamos | 205/792 |
| 6,749,792 B2 | 6/2004 | Olsen | 264/328.1 |
| 6,749,887 B1 | 6/2004 | Dick | 427/2.13 |
| 6,751,491 B2 | 6/2004 | Lew | 600/345 |
| 6,752,817 B2 | 6/2004 | Flora | 606/181 |
| 6,753,187 B2 | 6/2004 | Cizdziel | 436/169 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |

(56) References Cited

U.S. PATENT DOCUMENTS

| | | | | |
|---|---|---|---|---|
| 6,800,488 | B2 | 10/2004 | Khan | 436/166 |
| 6,801,041 | B2 | 10/2004 | Karinka | 324/444 |
| 6,801,804 | B2 | 10/2004 | Miller | 604/20 |
| 6,802,199 | B2 | 10/2004 | Hilgers | 72/370.1 |
| 6,802,811 | B1 | 10/2004 | Slepian | 600/309 |
| 6,802,957 | B2 | 10/2004 | Jung | 205/777.5 |
| 6,805,780 | B1 | 10/2004 | Ryu | 204/403.01 |
| 6,808,908 | B2 | 10/2004 | Yao | 435/181 |
| 6,808,937 | B2 | 10/2004 | Ligler | 436/518 |
| 6,809,807 | B1 | 10/2004 | Erickson | 356/213 |
| 6,811,406 | B2 | 11/2004 | Grube | 439/66 |
| 6,811,557 | B2 | 11/2004 | Schraga | 606/182 |
| 6,811,659 | B2 | 11/2004 | Vachon | 204/224 |
| 6,811,753 | B2 | 11/2004 | Hirao | 422/101 |
| 6,811,792 | B2 | 11/2004 | Roser | 424/423 |
| 6,812,031 | B1 | 11/2004 | Carlsson | 436/52 |
| 6,814,843 | B1 | 11/2004 | Bhullar | 204/403.01 |
| 6,814,844 | B2 | 11/2004 | Bhullar | 204/403.1 |
| 6,814,845 | B2 | 11/2004 | Wilson | 204/486 |
| 6,815,186 | B2 | 11/2004 | Clark | 435/183 |
| 6,816,742 | B2 | 11/2004 | Kim | 600/345 |
| 6,818,180 | B2 | 11/2004 | Douglas | 422/58 |
| 6,821,483 | B2 | 11/2004 | Phillips | 422/58 |
| 6,823,750 | B2 | 11/2004 | Hodges | 73/864.72 |
| 6,825,047 | B1 | 11/2004 | Woudenberg | 436/518 |
| 6,827,250 | B2 | 12/2004 | Uhland | 228/110.1 |
| 6,827,829 | B2 | 12/2004 | Kawanaka | 204/403.02 |
| 6,829,507 | B1 | 12/2004 | Lidman | 607/19 |
| 6,830,551 | B1 | 12/2004 | Uchigaki | 600/584 |
| 6,830,668 | B2 | 12/2004 | Musho | 204/400 |
| 6,830,669 | B2 | 12/2004 | Miyazaki | 204/409 |
| 6,830,934 | B1 | 12/2004 | Hardling | 436/166 |
| 6,833,540 | B2 | 12/2004 | MacKenzie | 250/214 |
| 6,835,184 | B1 | 12/2004 | Sage | 604/46 |
| 6,835,553 | B2 | 12/2004 | Han | 435/14 |
| 6,835,570 | B2 | 12/2004 | Patel | 436/8 |
| 6,837,858 | B2 | 1/2005 | Cunningham | 600/573 |
| 6,837,976 | B2 | 1/2005 | Cai | 204/403.14 |
| 6,837,988 | B2 | 1/2005 | Leong | 205/792 |
| 6,840,912 | B2 | 1/2005 | Kloepfer | 600/583 |
| 6,841,052 | B2 | 1/2005 | Musho | 204/401 |
| 6,843,254 | B2 | 1/2005 | Tapper | 128/898 |
| 6,843,902 | B1 | 1/2005 | Penner | 205/76 |
| 6,847,451 | B2 | 1/2005 | Pugh | 356/436 |
| 6,849,052 | B2 | 2/2005 | Uchigaki | 600/584 |
| 6,849,168 | B2 | 2/2005 | Crumly | 204/416 |
| 6,849,216 | B2 | 2/2005 | Rappin | 264/134 |
| 6,849,456 | B2 | 2/2005 | Patel | 436/8 |
| 6,850,790 | B2 | 2/2005 | Berner | 600/347 |
| 6,852,119 | B1 | 2/2005 | Abulhaj | 606/182 |
| 6,852,212 | B2 | 2/2005 | Maxwell | 205/775 |
| 6,852,500 | B1 | 2/2005 | Hoss | 435/14 |
| 6,853,854 | B1 | 2/2005 | Proniewicz | 600/319 |
| 6,855,243 | B2 | 2/2005 | Khan | 205/777.5 |
| 6,856,125 | B2 | 2/2005 | Kermani | 324/71.1 |
| 6,856,928 | B2 | 2/2005 | Harmon | 702/84 |
| 6,858,015 | B2 | 2/2005 | List | 600/583 |
| 6,858,401 | B2 | 2/2005 | Phillips | 435/14 |
| 6,859,738 | B2 | 2/2005 | Bush | 702/25 |
| 6,862,466 | B2 | 3/2005 | Ackerman | 600/347 |
| 6,862,534 | B2 | 3/2005 | Sterling | 702/23 |
| 6,863,800 | B2 | 3/2005 | Karinka | 205/777.5 |
| 6,863,801 | B2 | 3/2005 | Hodges | 205/792 |
| 6,865,408 | B1 | 3/2005 | Abbink | 600/310 |
| 6,866,641 | B2 | 3/2005 | Marshall | 600/583 |
| 6,866,675 | B2 | 3/2005 | Perez | 606/181 |
| 6,866,758 | B2 | 3/2005 | Bhullar | 204/403.2 |
| 6,866,822 | B1 | 3/2005 | House | 422/82.05 |
| 6,872,297 | B2 | 3/2005 | Mansouri | 205/775 |
| 6,872,298 | B2 | 3/2005 | Kermani | 205/777.5 |
| 6,872,299 | B2 | 3/2005 | Kermani | 205/777.5 |
| 6,872,358 | B2 | 3/2005 | Hagen | 422/61 |
| 6,875,327 | B1 | 4/2005 | Miyazaki | 204/403.14 |
| 6,881,541 | B2 | 4/2005 | Petersen | 435/6 |
| 6,887,202 | B2 | 5/2005 | Currie | 600/309 |
| 6,911,937 | B1 | 6/2005 | Sparrow | 342/188 |
| 6,913,210 | B2 | 7/2005 | Baasch | 239/407 |
| 6,913,668 | B2 | 7/2005 | Matzinger | 156/256 |
| 6,918,901 | B1 | 7/2005 | Theeuwes | 604/500 |
| 6,929,631 | B1 | 8/2005 | Brugger | 604/502 |
| RE38,803 | E | 9/2005 | Rodgers, Jr. | |
| 6,939,685 | B2 | 9/2005 | Ouyang | 435/26 |
| 6,960,323 | B2 | 11/2005 | Guo | 422/60 |
| 6,977,722 | B2 | 12/2005 | Wohlstadter et al. | 356/246 |
| 6,982,431 | B2 | 1/2006 | Modlin | 250/573 |
| 7,041,210 | B2 | 5/2006 | Hodges | 205/792 |
| 7,043,821 | B2 | 5/2006 | Hodges | 29/594 |
| 7,045,046 | B2 | 5/2006 | Chambers | 204/400 |
| 7,049,087 | B2 | 5/2006 | Jenny | 435/13 |
| D522,656 | S | 6/2006 | Orr | D24/169 |
| 7,059,352 | B2 | 6/2006 | Bohm | 137/828 |
| 7,060,168 | B2 | 6/2006 | Taniike | 204/403.04 |
| 7,079,252 | B1 | 7/2006 | Debreczeny | 356/451 |
| 7,113,172 | B2 | 9/2006 | Hohl | 345/168 |
| 7,134,550 | B2 | 11/2006 | Groth | 206/366 |
| 7,141,034 | B2 | 11/2006 | Eppstein | 604/22 |
| 7,144,709 | B2 | 12/2006 | Ouyang | 435/7.9 |
| 7,156,117 | B2 | 1/2007 | Bohm | 137/14 |
| 7,156,810 | B2 | 1/2007 | Cho | 600/365 |
| 7,157,723 | B2 | 1/2007 | Colvin | 250/458.1 |
| 7,160,678 | B1 | 1/2007 | Kayyem | 435/6 |
| 7,162,289 | B2 | 1/2007 | Shah | 600/345 |
| 7,166,208 | B2 | 1/2007 | Zweig | 205/777.5 |
| 7,167,735 | B2 | 1/2007 | Uchida | 600/310 |
| 7,169,116 | B2 | 1/2007 | Day | 600/583 |
| 7,169,117 | B2 | 1/2007 | Allen | 600/584 |
| 7,169,289 | B2 | 1/2007 | Schulein | 205/777.5 |
| 7,169,600 | B2 | 1/2007 | Hoss | 435/287.1 |
| 7,172,728 | B2 | 2/2007 | Otake | 422/58 |
| 7,174,799 | B2 | 2/2007 | Yoshida | 600/347 |
| 7,175,641 | B1 | 2/2007 | Schraga | 606/181 |
| 7,175,642 | B2 | 2/2007 | Briggs | 606/181 |
| 7,179,233 | B2 | 2/2007 | Chang | 600/584 |
| 7,182,910 | B2 | 2/2007 | Allen | 422/50 |
| 7,183,068 | B2 | 2/2007 | Burson | 435/14 |
| 7,183,508 | B2 | 2/2007 | Kasai | 200/51.09 |
| 7,188,034 | B2 | 3/2007 | Staib | 702/22 |
| 7,189,576 | B2 | 3/2007 | Fukuoka | 436/170 |
| 7,190,988 | B2 | 3/2007 | Say | 600/345 |
| 7,192,405 | B2 | 3/2007 | DeNuzzio | 600/583 |
| 7,192,450 | B2 | 3/2007 | Brauker | 623/23.76 |
| 7,195,704 | B2 | 3/2007 | Kermani | 205/777.5 |
| 7,198,606 | B2 | 4/2007 | Boecker | 600/583 |
| 7,199,594 | B2 | 4/2007 | Kermani | 324/663 |
| 7,202,854 | B2 | 4/2007 | Hohl | 345/168 |
| 7,206,620 | B2 | 4/2007 | Erickson | 600/310 |
| 7,206,623 | B2 | 4/2007 | Blank | 600/344 |
| D542,681 | S | 5/2007 | Young | D10/80 |
| 7,211,052 | B2 | 5/2007 | Roe | 600/584 |
| 7,211,096 | B2 | 5/2007 | Kuhr | 606/182 |
| 7,212,925 | B2 | 5/2007 | Genshaw | 702/23 |
| 7,213,720 | B2 | 5/2007 | Giraud | 220/839 |
| 7,215,982 | B2 | 5/2007 | Oshima | 600/310 |
| 7,215,983 | B2 | 5/2007 | Cho | 600/316 |
| 7,223,248 | B2 | 5/2007 | Erickson | 600/584 |
| 7,225,008 | B1 | 5/2007 | Ward | 600/345 |
| D543,878 | S | 6/2007 | Castillo | D10/81 |
| D545,438 | S | 6/2007 | Huang | D24/186 |
| 7,225,535 | B2 | 6/2007 | Feldman | 29/831 |
| 7,226,414 | B2 | 6/2007 | Ballerstadt | 600/365 |
| 7,226,461 | B2 | 6/2007 | Boecker | 606/181 |
| 7,226,978 | B2 | 6/2007 | Tapsak | 525/296 |
| 7,227,156 | B2 | 6/2007 | Colvin | 250/458.1 |
| 7,228,159 | B2 | 6/2007 | Petersson | 600/316 |
| 7,228,162 | B2 | 6/2007 | Ward | 600/345 |
| 7,228,163 | B2 | 6/2007 | Ackerman | 600/347 |
| 7,229,458 | B2 | 6/2007 | Freeman | 606/181 |
| 7,232,451 | B2 | 6/2007 | Boecker | 606/181 |
| 7,232,510 | B2 | 6/2007 | Miyazaki | 204/403.1 |
| 7,233,816 | B2 | 6/2007 | Blank | 600/310 |
| 7,235,056 | B2 | 6/2007 | Duchon | 600/583 |
| 7,235,170 | B2 | 6/2007 | Watanabe | 205/777.5 |
| 7,235,378 | B2 | 6/2007 | Yonehara | 435/14 |
| 7,236,812 | B1 | 6/2007 | Ballerstadt | 600/316 |

(56) References Cited

U.S. PATENT DOCUMENTS

| | | | | |
|---|---|---|---|---|
| 7,236,814 B2 | 6/2007 | Shioi | | 600/344 |
| D545,705 S | 7/2007 | Voege | | D10/81 |
| D546,216 S | 7/2007 | Bolognesi | | D10/81 |
| D546,218 S | 7/2007 | Grasso | | D10/81 |
| 2,747,138 A1 | 7/2007 | Reghabi | | 600/365 |
| 7,238,192 B2 | 7/2007 | List | | 606/182 |
| 7,238,534 B1 | 7/2007 | Zimmer | | 436/169 |
| 7,241,265 B2 | 7/2007 | Cummings | | 600/300 |
| 7,244,264 B2 | 7/2007 | Roe | | 606/181 |
| 7,244,265 B2 | 7/2007 | Freeman | | 606/181 |
| 7,244,266 B2 | 7/2007 | Garthe | | 606/181 |
| 7,247,144 B2 | 7/2007 | Douglas | | 600/583 |
| 7,250,037 B2 | 7/2007 | Shermer | | 604/134 |
| 7,250,056 B2 | 7/2007 | Hamamoto | | 606/181 |
| 7,250,095 B2 | 7/2007 | Black | | 204/403.14 |
| 7,250,105 B1 | 7/2007 | Davies | | 205/777.5 |
| 7,251,513 B2 | 7/2007 | Kondoh | | 600/310 |
| 7,251,514 B2 | 7/2007 | Cho | | 600/316 |
| 7,251,515 B2 | 7/2007 | Cho | | 600/316 |
| 7,251,516 B2 | 7/2007 | Walker | | 600/316 |
| 7,251,517 B2 | 7/2007 | Cho | | 600/316 |
| 7,251,518 B2 | 7/2007 | Herrmann | | 600/322 |
| 7,252,804 B2 | 8/2007 | Miyashita | | 422/104 |
| 7,254,426 B2 | 8/2007 | Cho | | 600/316 |
| 7,254,427 B2 | 8/2007 | Cho | | 600/316 |
| 7,254,428 B2 | 8/2007 | Cho | | 600/316 |
| 7,254,429 B2 | 8/2007 | Schurman | | 600/316 |
| 7,254,430 B2 | 8/2007 | Cho | | 600/316 |
| 7,254,432 B2 | 8/2007 | Fine | | 600/335 |
| 7,258,673 B2 | 8/2007 | Racchini | | 600/583 |
| 7,258,693 B2 | 8/2007 | Freeman | | 606/181 |
| 7,262,061 B2 | 8/2007 | Petrich | | 436/169 |
| 7,264,139 B2 | 9/2007 | Brickwood | | 221/270 |
| 7,264,627 B2 | 9/2007 | Perez | | 606/181 |
| 7,266,400 B2 | 9/2007 | Fine | | 600/316 |
| 7,267,665 B2 | 9/2007 | Steil | | 604/131 |
| 7,267,750 B2 | 9/2007 | Watanabe | | 204/403.04 |
| 7,270,247 B2 | 9/2007 | Charlton | | 221/59 |
| 7,271,912 B2 | 9/2007 | Sterling | | 356/436 |
| 7,273,484 B2 | 9/2007 | Thoes | | 606/181 |
| 7,276,027 B2 | 10/2007 | Haar | | 600/309 |
| 7,276,029 B2 | 10/2007 | Goode | | 600/365 |
| 7,276,146 B2 | 10/2007 | Wilsey | | 205/792 |
| 7,276,147 B2 | 10/2007 | Wilsey | | 205/792 |
| 7,276,380 B2 | 10/2007 | Fukuyama | | 436/164 |
| 7,277,740 B2 | 10/2007 | Rohleder | | 600/316 |
| 7,278,983 B2 | 10/2007 | Ireland | | 604/66 |
| 7,279,130 B2 | 10/2007 | Brown | | 422/64 |
| 7,282,058 B2 | 10/2007 | Levin | | 606/181 |
| 7,287,318 B2 | 10/2007 | Bhullar | | 29/825 |
| 7,288,073 B2 | 10/2007 | Effenhauser | | 600/584 |
| 7,288,102 B2 | 10/2007 | Griffin | | 606/182 |
| 7,288,174 B2 | 10/2007 | Cui | | 204/403.14 |
| 7,289,836 B2 | 10/2007 | Colvin | | 600/316 |
| 7,291,117 B2 | 11/2007 | Boecker | | 600/583 |
| 7,291,159 B2 | 11/2007 | Schmelzeisen | | 606/181 |
| 7,291,256 B2 | 11/2007 | Teodorczyk | | 205/777.5 |
| 7,291,497 B2 | 11/2007 | Holmes | | 435/287.2 |
| 7,294,246 B2 | 11/2007 | Gundel | | 204/403.14 |
| 7,295,867 B2 | 11/2007 | Berner | | 600/345 |
| 7,297,122 B2 | 11/2007 | Boecker | | 600/583 |
| 7,297,151 B2 | 11/2007 | Boecker | | 606/181 |
| 7,297,152 B2 | 11/2007 | Fukuzawa | | 606/181 |
| 7,297,241 B2 | 11/2007 | Kontschieder | | 204/403.01 |
| 7,297,248 B2 | 11/2007 | Bae | | 205/777.5 |
| 7,297,627 B2 | 11/2007 | Shah | | 438/622 |
| 7,299,079 B2 | 11/2007 | Rebec | | 600/316 |
| 7,299,080 B2 | 11/2007 | Acosta | | 600/316 |
| 7,299,081 B2 | 11/2007 | Mace | | 600/345 |
| 7,299,082 B2 | 11/2007 | Feldman | | 600/347 |
| 7,300,402 B2 | 11/2007 | Iliff | | 600/300 |
| 7,301,629 B2 | 11/2007 | Bambot | | 356/337 |
| 7,303,573 B2 | 12/2007 | D'Agostino | | 606/181 |
| 7,303,726 B2 | 12/2007 | McAllister | | 422/68.1 |
| 7,303,922 B2 | 12/2007 | Jeng | | 436/164 |
| 7,305,896 B2 | 12/2007 | Howell | | 73/864.02 |
| 7,306,560 B2 | 12/2007 | Iliff | | 600/300 |
| 7,308,164 B1 | 12/2007 | Banks | | 385/12 |
| 7,308,292 B2 | 12/2007 | Colvin | | 600/310 |
| 7,310,542 B2 | 12/2007 | Jeon | | 600/344 |
| 7,310,543 B2 | 12/2007 | Smart | | 600/345 |
| 7,310,544 B2 | 12/2007 | Brister | | 600/345 |
| 7,311,718 B2 | 12/2007 | Schraga | | 606/181 |
| 7,311,812 B2 | 12/2007 | Forrow | | 204/403.06 |
| 7,312,042 B1 | 12/2007 | Petyt | | 435/7.1 |
| 7,313,425 B2 | 12/2007 | Finarov | | 600/310 |
| 7,314,453 B2 | 1/2008 | Kuo | | 600/584 |
| 7,315,752 B2 | 1/2008 | Kraemer | | 600/316 |
| 7,316,700 B2 | 1/2008 | Alden | | 606/181 |
| 7,316,766 B2 | 1/2008 | Chen | | 204/403.01 |
| 7,316,929 B2 | 1/2008 | Purcell | | 436/8 |
| 7,317,938 B2 | 1/2008 | Lorenz | | 600/316 |
| 7,317,939 B2 | 1/2008 | Fine | | 600/322 |
| 7,322,942 B2 | 1/2008 | Roe | | 600/583 |
| 7,322,996 B2 | 1/2008 | Taylor | | 606/181 |
| 7,322,997 B2 | 1/2008 | Shi | | 606/181 |
| 7,322,998 B2 | 1/2008 | Kuhr | | 606/182 |
| 7,323,098 B2 | 1/2008 | Miyashita | | 205/777.5 |
| 7,323,141 B2 | 1/2008 | Kirchhevel | | 422/68.1 |
| 7,323,315 B2 | 1/2008 | Marfurt | | 435/7.25 |
| 7,324,012 B2 | 1/2008 | Mann | | 340/870.07 |
| 7,328,052 B2 | 2/2008 | Samsoondar | | 600/310 |
| 7,331,931 B2 | 2/2008 | Freeman | | 600/583 |
| 7,335,292 B2 | 2/2008 | Hodges | | 205/775 |
| 7,335,294 B2 | 2/2008 | Heller | | 205/792 |
| 7,337,918 B2 | 3/2008 | Fowler | | 221/65 |
| 7,338,639 B2 | 3/2008 | Burke | | 422/82.1 |
| 7,343,188 B2 | 3/2008 | Sohrab | | 600/345 |
| 7,344,499 B1 | 3/2008 | Prausnitz | | 600/309 |
| 7,344,500 B2 | 3/2008 | Talbot | | 600/365 |
| 7,344,507 B2 | 3/2008 | Briggs | | 600/583 |
| 7,344,626 B2 | 3/2008 | Harding | | 204/403.01 |
| 7,347,925 B2 | 3/2008 | Hsieh | | 205/777.5 |
| 7,347,926 B2 | 3/2008 | Morita | | 205/792 |
| 7,347,973 B2 | 3/2008 | Douglas | | 422/61 |
| RE40,198 E | 4/2008 | Buck | | 205/777.5 |
| 7,351,213 B2 | 4/2008 | Wong | | 600/584 |
| 7,351,323 B2 | 4/2008 | Iketaki | | 205/777.5 |
| 7,351,375 B2 | 4/2008 | Noda | | 422/82.01 |
| 7,351,770 B2 | 4/2008 | Liu | | 525/283 |
| 7,357,808 B2 | 4/2008 | Kennedy | | 606/181 |
| 7,357,851 B2 | 4/2008 | Reid | | 204/403.04 |
| 7,361,182 B2 | 4/2008 | Fukuda | | 606/181 |
| 7,361,307 B2 | 4/2008 | Shartle | | 422/82.01 |
| 7,371,247 B2 | 5/2008 | Boecker | | 606/181 |
| 7,372,277 B2 | 5/2008 | Diamond | | 324/444 |
| 7,374,544 B2 | 5/2008 | Freeman | | 600/583 |
| 7,374,546 B2 | 5/2008 | Roe | | 600/583 |
| 7,378,007 B2 | 5/2008 | Moerman | | 204/403.03 |
| 7,378,270 B2 | 5/2008 | Azarnia | | 435/287.2 |
| 7,402,616 B2 | 7/2008 | Rodgers | | 523/160 |
| 7,404,815 B2 | 7/2008 | Kollias | | 604/501 |
| 7,410,468 B2 | 8/2008 | Freeman | | 600/583 |
| 7,429,630 B2 | 9/2008 | Liu | | 525/283 |
| 7,431,814 B2 | 10/2008 | Hodges | | 204/403.02 |
| 7,431,820 B2 | 10/2008 | Hodges | | 205/777.5 |
| 7,438,694 B2 | 10/2008 | Boozer | | 600/583 |
| D579,652 S | 11/2008 | Lim | | D3/201 |
| D579,653 S | 11/2008 | Lim | | D3/201 |
| 7,458,956 B1 | 12/2008 | Adams | | |
| 7,462,265 B2 | 12/2008 | Leach | | 204/403.14 |
| 7,465,380 B2 | 12/2008 | Rodgers | | 204/403.14 |
| 7,468,125 B2 | 12/2008 | Kraft | | 205/792 |
| D585,314 S | 1/2009 | Schvetz | | D10/78 |
| 7,473,264 B2 | 1/2009 | Allen | | 606/181 |
| 7,474,390 B2 | 1/2009 | Robinson | | 356/42 |
| 7,474,391 B2 | 1/2009 | Baskeyfield | | 356/42 |
| 7,481,776 B2 | 1/2009 | Boecker | | 600/583 |
| 7,481,818 B2 | 1/2009 | Allen | | 606/181 |
| D586,465 S | 2/2009 | Faulkner | | D24/146 |
| D586,466 S | 2/2009 | Smith | | D24/186 |
| D586,678 S | 2/2009 | Schvetz | | D10/81 |
| D586,916 S | 2/2009 | Faulkner | | D24/146 |
| 7,485,128 B2 | 2/2009 | Boecker | | 606/181 |

(56) References Cited

U.S. PATENT DOCUMENTS

| | | | |
|---|---|---|---|
| 7,491,178 B2 | 2/2009 | Boecker | 600/583 |
| 7,498,132 B2 | 3/2009 | Yu | 435/6 |
| 7,501,052 B2 | 3/2009 | Iyengar | 205/777.5 |
| 7,501,093 B2 | 3/2009 | Demelo | 422/58 |
| 7,521,019 B2 | 4/2009 | Polak | 422/82.06 |
| 7,524,293 B2 | 4/2009 | Freeman | 600/583 |
| 7,537,571 B2 | 5/2009 | Freeman | 600/583 |
| 7,547,287 B2 | 6/2009 | Boecker | 600/583 |
| 7,548,772 B2 | 6/2009 | Shartle | 600/345 |
| 7,553,511 B2 | 6/2009 | Hleong | 427/2.28 |
| 7,563,232 B2 | 7/2009 | Freeman | 600/583 |
| D598,126 S | 8/2009 | Alvarez-Icaza | D24/225 |
| 7,572,356 B2 | 8/2009 | Rodgers | 204/403.05 |
| 7,575,558 B2 | 8/2009 | Boecker | 600/573 |
| D600,349 S | 9/2009 | Bell | D24/169 |
| D600,812 S | 9/2009 | Lei | D24/169 |
| D600,813 S | 9/2009 | Bell | D24/169 |
| D601,255 S | 9/2009 | Schvetz | D24/169 |
| D601,258 S | 9/2009 | Bell | D24/169 |
| 7,582,063 B2 | 9/2009 | Wurster | 600/584 |
| 7,582,099 B2 | 9/2009 | Freeman | 606/181 |
| 7,586,590 B2 | 9/2009 | Baskeyfield | 356/42 |
| 7,588,670 B2 | 9/2009 | Rodgers | 204/403.14 |
| 7,589,828 B2 | 9/2009 | Robinson | 356/42 |
| 7,592,151 B2 | 9/2009 | Liu | 435/14 |
| 7,593,097 B2 | 9/2009 | Robinson | 356/42 |
| 7,604,592 B2 | 10/2009 | Freeman | 600/309 |
| 7,604,722 B2 | 10/2009 | Hodges | 204/403.02 |
| 7,608,175 B2 | 10/2009 | Hodges | 204/403.02 |
| 7,618,522 B2 | 11/2009 | Davies | 204/403.14 |
| 7,645,263 B2 | 1/2010 | Angel et al. | |
| 7,648,468 B2 | 1/2010 | Boecker | 600/583 |
| 7,648,469 B2 | 1/2010 | Boecker | 600/583 |
| 7,653,492 B2 | 1/2010 | Davies | 702/22 |
| 7,654,127 B2 | 2/2010 | Krulevitch | 73/1.16 |
| 7,655,119 B2 | 2/2010 | Davies | 204/403.14 |
| 7,665,303 B2 | 2/2010 | Bohm | 60/643 |
| 7,666,287 B2 | 2/2010 | Zhao | 204/600 |
| D611,151 S | 3/2010 | Lei | D24/169 |
| D611,372 S | 3/2010 | Salter | D10/81 |
| D611,489 S | 3/2010 | Bell | D14/486 |
| D611,853 S | 3/2010 | Salter | D10/81 |
| D612,274 S | 3/2010 | Heidemann | D10/78 |
| D612,275 S | 3/2010 | Salter | D10/81 |
| D612,279 S | 3/2010 | Heidemann | D10/103 |
| 7,674,232 B2 | 3/2010 | Boecker | 600/583 |
| 7,682,318 B2 | 3/2010 | Alden | 600/583 |
| 7,713,214 B2 | 5/2010 | Freeman et al. | 600/583 |
| 7,749,174 B2 | 7/2010 | Alden et al. | |
| 7,833,172 B2 | 11/2010 | Hein et al. | 600/583 |
| 7,879,058 B2 | 2/2011 | Ikeda | 606/182 |
| 7,901,365 B2 | 3/2011 | Freeman et al. | 600/583 |
| 7,976,778 B2 | 7/2011 | Drucker et al. | |
| 8,062,235 B2 | 11/2011 | Planman et al. | |
| 8,079,960 B2 | 12/2011 | Briggs et al. | 600/583 |
| 8,162,968 B2 | 4/2012 | Boozer et al. | 606/182 |
| 8,197,421 B2 | 6/2012 | Freeman et al. | |
| 8,206,319 B2 | 6/2012 | Freeman et al. | 600/583 |
| 8,231,548 B2 | 7/2012 | Hoenes | 600/583 |
| 8,251,922 B2 | 8/2012 | List et al. | 600/584 |
| 8,282,576 B2 | 10/2012 | Marsot et al. | |
| 8,388,639 B2 | 3/2013 | Nicholls et al. | |
| 8,491,500 B2 | 7/2013 | Briggs et al. | |
| 2001/0017269 A1 | 8/2001 | Heller | 205/777.5 |
| 2001/0018353 A1 | 8/2001 | Ishigaki | 455/566 |
| 2001/0023349 A1 | 9/2001 | Van Tassel et al. | 606/53 |
| 2001/0027328 A1 | 10/2001 | Lum | 606/186 |
| 2001/0031931 A1 | 10/2001 | Cunningham | 600/573 |
| 2001/0037072 A1 | 11/2001 | Virtanen | |
| 2001/0037355 A1 | 11/2001 | Britt | 709/201 |
| 2001/0042004 A1 | 11/2001 | Taub | 705/11 |
| 2001/0045355 A1 | 11/2001 | Gephart | 204/400 |
| 2001/0054319 A1 | 12/2001 | Heller | 73/849 |
| 2002/0002326 A1 | 1/2002 | Causey | 600/300 |
| 2002/0002344 A1 | 1/2002 | Douglas | 600/583 |
| 2002/0004196 A1 | 1/2002 | Whitson | 600/573 |
| 2002/0016568 A1 | 2/2002 | Lebel | 604/131 |
| 2002/0016923 A1 | 2/2002 | Knaus | 713/200 |
| 2002/0019606 A1 | 2/2002 | Lebel | 604/66 |
| 2002/0019747 A1 | 2/2002 | Ware | 705/2 |
| 2002/0020646 A1 | 2/2002 | Groth et al. | |
| 2002/0025469 A1 | 2/2002 | Heller | 429/43 |
| 2002/0029058 A1 | 3/2002 | Levaughn | 606/181 |
| 2002/0040208 A1 | 4/2002 | Flaherty | 604/288.01 |
| 2002/0040230 A1 | 4/2002 | Kuhr | 606/181 |
| 2002/0042090 A1 | 4/2002 | Heller | 435/14 |
| 2002/0042594 A1 | 4/2002 | Lum | 604/117 |
| 2002/0044890 A1 | 4/2002 | Black | 422/56 |
| 2002/0052618 A1 | 5/2002 | Haar | 606/181 |
| 2002/0053523 A1 | 5/2002 | Liamos | 205/787 |
| 2002/0057993 A1 | 5/2002 | Maisey | 422/82.01 |
| 2002/0058902 A1 | 5/2002 | Kollias et al. | 604/20 |
| 2002/0076349 A1 | 6/2002 | Aitken | 422/58 |
| 2002/0078091 A1 | 6/2002 | Vu | 707/513 |
| 2002/0081588 A1 | 6/2002 | Lumley-Woodyear | 435/6 |
| 2002/0082543 A1 | 6/2002 | Park | 604/21 |
| 2002/0084196 A1 | 7/2002 | Liamos | 205/792 |
| 2002/0087056 A1* | 7/2002 | Aceti et al. | 600/309 |
| 2002/0092612 A1 | 7/2002 | Davies | 156/292 |
| 2002/0099308 A1 | 7/2002 | Bojan | 600/573 |
| 2002/0103499 A1 | 8/2002 | Perez | 606/182 |
| 2002/0109600 A1 | 8/2002 | Mault et al. | |
| 2002/0111634 A1 | 8/2002 | Stoianovici et al. | |
| 2002/0120216 A1 | 8/2002 | Fritz | 600/583 |
| 2002/0123335 A1 | 9/2002 | Luna | 455/419 |
| 2002/0130042 A1 | 9/2002 | Moerman | 204/403.01 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0141032 A1 | 10/2002 | Guarr et al. | 359/265 |
| 2002/0148739 A2 | 10/2002 | Liamos | 205/787 |
| 2002/0156355 A1 | 10/2002 | Gough | 600/345 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0169393 A1 | 11/2002 | Cunningham | 600/573 |
| 2002/0169394 A1 | 11/2002 | Eppstein | 600/573 |
| 2002/0176984 A1 | 11/2002 | Smart | 428/336 |
| 2002/0177761 A1 | 11/2002 | Orloff | 600/309 |
| 2002/0177763 A1 | 11/2002 | Burns | 600/345 |
| 2002/0188224 A1 | 12/2002 | Roe | 600/584 |
| 2003/0014010 A1 | 1/2003 | Carpenter | 604/117 |
| 2003/0018282 A1 | 1/2003 | Effenhauser | 600/583 |
| 2003/0018300 A1 | 1/2003 | Duchon | 604/164.01 |
| 2003/0028126 A1 | 2/2003 | List | 600/583 |
| 2003/0032077 A1 | 2/2003 | Itoh | 435/14 |
| 2003/0038047 A1 | 2/2003 | Sleva | 206/370 |
| 2003/0050573 A1 | 3/2003 | Kuhr | 600/567 |
| 2003/0050656 A1 | 3/2003 | Schraga | 606/182 |
| 2003/0057391 A1 | 3/2003 | Krulevitch | 251/11 |
| 2003/0060730 A1 | 3/2003 | Perez | 600/576 |
| 2003/0069509 A1 | 4/2003 | Matzinger et al. | 600/504 |
| 2003/0072647 A1 | 4/2003 | Lum | 415/1 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker | 600/573 |
| 2003/0083685 A1 | 5/2003 | Freeman | 606/181 |
| 2003/0083686 A1* | 5/2003 | Freeman et al. | 606/181 |
| 2003/0088191 A1 | 5/2003 | Freeman | 600/583 |
| 2003/0089730 A1 | 5/2003 | May | 221/232 |
| 2003/0092982 A1 | 5/2003 | Eppstein | |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0109860 A1 | 6/2003 | Black | 606/10 |
| 2003/0111357 A1 | 6/2003 | Black | 205/775 |
| 2003/0113827 A1 | 6/2003 | Burkoth | 435/14 |
| 2003/0116447 A1 | 6/2003 | Surridge | 205/777.5 |
| 2003/0120297 A1 | 6/2003 | Beyerlein | 606/185 |
| 2003/0135333 A1 | 7/2003 | Aceti | 702/31 |
| 2003/0136189 A1 | 7/2003 | Lauman | 73/304 C |
| 2003/0143113 A2 | 7/2003 | Yuzhakov | 422/56 |
| 2003/0144608 A1 | 7/2003 | Kojima | 600/583 |

(56) References Cited

U.S. PATENT DOCUMENTS

| | | |
|---|---|---|
| 2003/0144609 A1 | 7/2003 | Kennedy ................. 600/583 |
| 2003/0146110 A1 | 8/2003 | Karinka ................ 205/777.5 |
| 2003/0149348 A1 | 8/2003 | Raskas .................... 600/310 |
| 2003/0149377 A1 | 8/2003 | Erickson .................. 600/573 |
| 2003/0150745 A1 | 8/2003 | Teodorczyk et al. |
| 2003/0153900 A1 | 8/2003 | Aceti ..................... 604/890.1 |
| 2003/0191376 A1 | 10/2003 | Samuels ................. 600/309 |
| 2003/0191415 A1 | 10/2003 | Moerman ............... 600/584 |
| 2003/0195435 A1 | 10/2003 | Williams ................ 600/583 |
| 2003/0195540 A1 | 10/2003 | Moerman ............... 606/181 |
| 2003/0199744 A1 | 10/2003 | Buse ...................... 600/347 |
| 2003/0199789 A1 | 10/2003 | Boecker ................. 600/575 |
| 2003/0199790 A1 | 10/2003 | Boecker ................. 600/576 |
| 2003/0199791 A1 | 10/2003 | Boecker ................. 600/576 |
| 2003/0199891 A1 | 10/2003 | Argauer ................. 606/181 |
| 2003/0199893 A1 | 10/2003 | Boecker ................. 606/181 |
| 2003/0199894 A1 | 10/2003 | Boecker ................. 606/181 |
| 2003/0199896 A1* | 10/2003 | Boecker et al. ......... 606/181 |
| 2003/0199897 A1 | 10/2003 | Boecker ................. 606/181 |
| 2003/0199898 A1 | 10/2003 | Boecker ................. 606/181 |
| 2003/0199899 A1 | 10/2003 | Boecker ................. 606/181 |
| 2003/0199900 A1 | 10/2003 | Boecker ................. 606/181 |
| 2003/0199901 A1 | 10/2003 | Boecker ................. 606/181 |
| 2003/0199902 A1 | 10/2003 | Boecker ................. 606/181 |
| 2003/0199903 A1 | 10/2003 | Boecker ................. 606/181 |
| 2003/0199904 A1 | 10/2003 | Boecker ................. 606/181 |
| 2003/0199905 A1 | 10/2003 | Boecker ................. 606/181 |
| 2003/0199906 A1 | 10/2003 | Boecker ................. 606/181 |
| 2003/0199907 A1 | 10/2003 | Boecker ................. 606/181 |
| 2003/0199908 A1* | 10/2003 | Boecker et al. ......... 606/181 |
| 2003/0199909 A1* | 10/2003 | Boecker et al. ......... 606/181 |
| 2003/0199910 A1* | 10/2003 | Boecker et al. ......... 606/181 |
| 2003/0199911 A1* | 10/2003 | Boecker et al. ......... 606/181 |
| 2003/0199912 A1 | 10/2003 | Pugh ..................... 606/182 |
| 2003/0201194 A1 | 10/2003 | Heller .................. 205/777.5 |
| 2003/0203352 A1 | 10/2003 | Haviland ................ 435/4 |
| 2003/0206828 A1 | 11/2003 | Bell ....................... 422/44 |
| 2003/0208140 A1 | 11/2003 | Pugh ..................... 600/584 |
| 2003/0210811 A1 | 11/2003 | Dubowsky .............. 382/128 |
| 2003/0211619 A1 | 11/2003 | Olson et al. ............ 436/44 |
| 2003/0212344 A1 | 11/2003 | Yuzhakov ............... 600/583 |
| 2003/0212345 A1 | 11/2003 | McAllister .............. 600/584 |
| 2003/0212346 A1 | 11/2003 | McAllister .............. 600/584 |
| 2003/0212347 A1 | 11/2003 | Sohrab ................... 600/584 |
| 2003/0212379 A1 | 11/2003 | Bylund ................... 604/504 |
| 2003/0212423 A1 | 11/2003 | Pugh ..................... 606/181 |
| 2003/0212424 A1* | 11/2003 | Briggs et al. ............ 606/181 |
| 2003/0216767 A1 | 11/2003 | List ....................... 606/181 |
| 2003/0217918 A1 | 11/2003 | Davies ................. 204/403.14 |
| 2003/0220552 A1 | 11/2003 | Reghabi .................. 600/365 |
| 2003/0220663 A1 | 11/2003 | Fletcher ................. 606/182 |
| 2003/0223906 A1 | 12/2003 | McAllister .............. 422/58 |
| 2003/0225429 A1 | 12/2003 | Garthe ................... 606/182 |
| 2003/0225430 A1 | 12/2003 | Schraga ................. 606/182 |
| 2003/0228637 A1 | 12/2003 | Wang .................... 435/7.9 |
| 2003/0232370 A1 | 12/2003 | Trifiro .................... 435/6 |
| 2003/0233055 A1 | 12/2003 | Erickson ................ 600/573 |
| 2003/0233112 A1 | 12/2003 | Alden et al. ............ 606/181 |
| 2003/0233113 A1 | 12/2003 | Alden et al. ............ 606/182 |
| 2004/0006285 A1 | 1/2004 | Douglas .................. 600/583 |
| 2004/0007585 A1 | 1/2004 | Griffith .................. 221/232 |
| 2004/0009100 A1 | 1/2004 | Simons ................... 422/102 |
| 2004/0010279 A1 | 1/2004 | Freeman ................. 606/182 |
| 2004/0015064 A1 | 1/2004 | Parsons .................. 600/347 |
| 2004/0019250 A1 | 1/2004 | Catelli .................... 600/1 |
| 2004/0026243 A1 | 2/2004 | Davies ................ 204/403.14 |
| 2004/0026244 A1 | 2/2004 | Hodges .................. 204/409 |
| 2004/0030353 A1 | 2/2004 | Schmelzeisen .......... 606/201 |
| 2004/0031682 A1 | 2/2004 | Wilsey ................... 204/403.1 |
| 2004/0034318 A1 | 2/2004 | Fritz ...................... 604/19 |
| 2004/0038045 A1 | 2/2004 | Smart .................... 428/446 |
| 2004/0039303 A1* | 2/2004 | Wurster et al. ......... 600/584 |
| 2004/0039342 A1 | 2/2004 | Eppstein ................. 604/200 |
| 2004/0039407 A1 | 2/2004 | Schraga ................. 606/181 |
| 2004/0039408 A1 | 2/2004 | Abulhaj ................. 606/181 |
| 2004/0049219 A1* | 3/2004 | Briggs et al. ............ 606/181 |
| 2004/0049220 A1 | 3/2004 | Boecker ................. 606/181 |
| 2004/0054267 A1 | 3/2004 | Feldman ................. 600/316 |
| 2004/0055898 A1 | 3/2004 | Heller ................. 205/777.5 |
| 2004/0059256 A1 | 3/2004 | Perez ..................... 600/583 |
| 2004/0060818 A1 | 4/2004 | Feldman ............... 204/403.01 |
| 2004/0061841 A1 | 4/2004 | Black ..................... 355/30 |
| 2004/0064068 A1 | 4/2004 | DeNuzzio ............... 600/583 |
| 2004/0065669 A1 | 4/2004 | Giraud et al. |
| 2004/0068093 A1 | 4/2004 | Merrigan et al. |
| 2004/0068283 A1 | 4/2004 | Fukuzawa et al. ...... 606/181 |
| 2004/0069657 A1 | 4/2004 | Hodges .................. 205/787 |
| 2004/0092995 A1 | 5/2004 | Boecker ................. 606/181 |
| 2004/0096991 A1 | 5/2004 | Zhang .................... 436/518 |
| 2004/0098010 A1 | 5/2004 | Davison ................. 606/181 |
| 2004/0102803 A1 | 5/2004 | Boecker ................. 606/183 |
| 2004/0106858 A1 | 6/2004 | Say ....................... 600/345 |
| 2004/0106859 A1 | 6/2004 | Say ....................... 600/345 |
| 2004/0106860 A1 | 6/2004 | Say ....................... 600/345 |
| 2004/0106904 A1 | 6/2004 | Gonnelli ................. 604/173 |
| 2004/0106941 A1 | 6/2004 | Roe ....................... 606/181 |
| 2004/0115754 A1 | 6/2004 | Chang ................... 435/14 |
| 2004/0115831 A1 | 6/2004 | Meathrel ................ 436/514 |
| 2004/0116829 A1 | 6/2004 | Raney ................... 600/573 |
| 2004/0122339 A1 | 6/2004 | Roe |
| 2004/0127818 A1 | 7/2004 | Roe ....................... 600/583 |
| 2004/0127819 A1 | 7/2004 | Roe ....................... 600/583 |
| 2004/0127928 A1 | 7/2004 | Whitson ................. 606/181 |
| 2004/0127929 A1 | 7/2004 | Roe ....................... 606/181 |
| 2004/0132167 A1 | 7/2004 | Rule ..................... 435/287.1 |
| 2004/0133125 A1 | 7/2004 | Miyashita .............. 600/573 |
| 2004/0133127 A1 | 7/2004 | Roe ....................... 600/583 |
| 2004/0133227 A1* | 7/2004 | Shang ............. A61B 17/32093 606/182 |
| 2004/0138541 A1 | 7/2004 | Ward ..................... 600/345 |
| 2004/0138588 A1 | 7/2004 | Saikley .................. 600/583 |
| 2004/0138612 A1* | 7/2004 | Shermer et al. ......... 604/93.01 |
| 2004/0138688 A1 | 7/2004 | Giraud ................... 606/181 |
| 2004/0146958 A1 | 7/2004 | Bae ....................... 435/14 |
| 2004/0154932 A1 | 8/2004 | Deng .................. 205/777.5 |
| 2004/0157017 A1 | 8/2004 | Mauze .................. 428/35.7 |
| 2004/0157149 A1 | 8/2004 | Hofmann ................ 430/131 |
| 2004/0157319 A1 | 8/2004 | Keen ................... 435/287.2 |
| 2004/0157338 A1 | 8/2004 | Burke .................... 436/147 |
| 2004/0157339 A1 | 8/2004 | Burke .................... 436/149 |
| 2004/0158137 A1 | 8/2004 | Eppstein ................. 600/347 |
| 2004/0158271 A1 | 8/2004 | Hamamoto .............. 606/181 |
| 2004/0161737 A1 | 8/2004 | Yang ..................... 435/5 |
| 2004/0162473 A1 | 8/2004 | Sohrab ................... 600/345 |
| 2004/0162474 A1 | 8/2004 | Kiser ..................... 600/345 |
| 2004/0162506 A1 | 8/2004 | Duchon ................. 600/583 |
| 2004/0162573 A1 | 8/2004 | Keheiri .................. 606/182 |
| 2004/0167383 A1 | 8/2004 | Kim ...................... 600/365 |
| 2004/0171057 A1 | 9/2004 | Yang ..................... 435/6 |
| 2004/0171968 A1 | 9/2004 | Katsuki .................. 600/583 |
| 2004/0172000 A1 | 9/2004 | Roe ....................... 604/361 |
| 2004/0173472 A1 | 9/2004 | Jung ................... 205/777.5 |
| 2004/0173488 A1 | 9/2004 | Griffin ................... 206/363 |
| 2004/0176705 A1 | 9/2004 | Stevens .................. 600/584 |
| 2004/0176732 A1 | 9/2004 | Frazier .................. 604/345 |
| 2004/0178066 A1 | 9/2004 | Miyazaki ............. 204/403.01 |
| 2004/0178067 A1 | 9/2004 | Miyazaki .............. 204/403.1 |
| 2004/0178216 A1 | 9/2004 | Brickwood ............. 221/268 |
| 2004/0180379 A1 | 9/2004 | van Duyne ............. 435/7.1 |
| 2004/0182703 A1 | 9/2004 | Bell .................... 204/403.11 |
| 2004/0185568 A1 | 9/2004 | Matsumoto ............. 436/8 |
| 2004/0186359 A1 | 9/2004 | Beaudoin ............... 600/310 |
| 2004/0186394 A1 | 9/2004 | Roe ....................... 600/598 |
| 2004/0186500 A1 | 9/2004 | Koilke ................... 606/181 |
| 2004/0193201 A1 | 9/2004 | Kim ...................... 606/181 |
| 2004/0194302 A1 | 10/2004 | Bhullar .................. 29/847 |
| 2004/0197231 A1 | 10/2004 | Katsuki .................. 422/68.1 |
| 2004/0197821 A1 | 10/2004 | Bauer .................... 437/7.1 |
| 2004/0199062 A1 | 10/2004 | Petersson ............... 600/316 |
| 2004/0200720 A1 | 10/2004 | Musho ................ 204/403.01 |
| 2004/0200721 A1 | 10/2004 | Bhullar ................ 204/403.01 |
| 2004/0202576 A1 | 10/2004 | Aceti ................... 422/82.05 |
| 2004/0204662 A1 | 10/2004 | Perez ..................... 600/583 |
| 2004/0206625 A1 | 10/2004 | Bhullar ................ 204/403.1 |

(56) References Cited

U.S. PATENT DOCUMENTS

| | | | |
|---|---|---|---|
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.01 |
| 2004/0214253 A1 | 10/2004 | Paek | 435/7.92 |
| 2004/0215224 A1* | 10/2004 | Sakata et al. | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |
| 2004/0231983 A1 | 11/2004 | Shen | 204/403.01 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Shraga | 606/181 |
| 2004/0238357 A1 | 12/2004 | Bhullar | 204/400 |
| 2004/0238358 A1 | 12/2004 | Forrow | 204/403 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267121 A1 | 12/2004 | Sarvazyan et al. | |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1* | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1* | 1/2005 | Douglas et al. | 600/573 |
| 2005/0010137 A1 | 1/2005 | Hodges | 600/583 |
| 2005/0010198 A1 | 1/2005 | Marchitto | 606/9 |
| 2005/0011759 A1* | 1/2005 | Moerman et al. | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027181 A1 | 2/2005 | Goode, Jr. | 600/365 |
| 2005/0033196 A1 | 2/2005 | Alroy | |
| 2005/0033340 A1 | 2/2005 | Lipoma | 606/181 |
| 2005/0035014 A1* | 2/2005 | Cane | 206/365 |
| 2005/0049472 A1 | 3/2005 | Manda | 600/345 |
| 2005/0054908 A1 | 3/2005 | Blank | 600/316 |
| 2005/0059872 A1 | 3/2005 | Shartle | 600/347 |
| 2005/0061668 A1 | 3/2005 | Brenneman | 204/403.01 |
| 2005/0064528 A1 | 3/2005 | Kwon | 435/14 |
| 2005/0112712 A1 | 5/2005 | Ouyang | 435/14 |
| 2005/0118062 A1 | 6/2005 | Otake | 422/68.1 |
| 2005/0121343 A1* | 6/2005 | Miller et al. | A61M 5/3205 206/366 |
| 2005/0131440 A1 | 6/2005 | Starnes | |
| 2005/0140659 A1 | 6/2005 | Hohl | 345/169 |
| 2005/0149090 A1 | 7/2005 | Morita | 606/181 |
| 2005/0163176 A1 | 7/2005 | You et al. | 372/36 |
| 2005/0164299 A1 | 7/2005 | Stewart | 435/7.1 |
| 2005/0169810 A1 | 8/2005 | Hagen | 422/102 |
| 2005/0176153 A1 | 8/2005 | O'hara | 436/70 |
| 2005/0187442 A1 | 8/2005 | Cho et al. | |
| 2005/0205136 A1 | 9/2005 | Freeman | 137/554 |
| 2006/0030050 A1 | 2/2006 | Milne | 436/67 |
| 2006/0030761 A1 | 2/2006 | Raskas | 600/316 |
| 2006/0037859 A1 | 2/2006 | Hodges | 204/400 |
| 2006/0094985 A1 | 5/2006 | Aceti | 600/575 |
| 2006/0100542 A9 | 5/2006 | Wong | 600/583 |
| 2006/0160100 A1 | 7/2006 | Gao | 435/6 |
| 2006/0163061 A1 | 7/2006 | Hodges | 204/401 |
| 2006/0184065 A1 | 8/2006 | Deshmukh | 600/583 |
| 2006/0201804 A1 | 9/2006 | Chambers | 204/400 |
| 2006/0222566 A1 | 10/2006 | Brauker et al. | 422/68.1 |
| 2006/0229652 A1 | 10/2006 | Lio et al. | 606/182 |
| 2006/0231421 A1 | 10/2006 | Diamond | 205/777.5 |
| 2006/0231423 A1 | 10/2006 | Harding | 205/792 |
| 2006/0231425 A1 | 10/2006 | Harding | 205/792 |
| 2006/0232278 A1 | 10/2006 | Diamond | 324/444 |
| 2006/0232528 A1 | 10/2006 | Harding | 345/87 |
| 2006/0233666 A1 | 10/2006 | Vu | 422/68.1 |
| 2006/0234263 A1 | 10/2006 | Light, II | 435/6 |
| 2006/0247154 A1 | 11/2006 | Palmieri | 514/8 |
| 2006/0254932 A1 | 11/2006 | Hodges | 205/775 |
| 2006/0266644 A1 | 11/2006 | Pugh | 204/400 |
| 2006/0266765 A1 | 11/2006 | Pugh | 222/1 |
| 2006/0279431 A1 | 12/2006 | Bakarania | 340/870.02 |
| 2006/0281187 A1 | 12/2006 | Emery | 436/169 |
| 2007/0016239 A1 | 1/2007 | Sato | 606/181 |
| 2007/0017805 A1 | 1/2007 | Hodges | 204/400 |
| 2007/0027370 A1 | 2/2007 | Brauker | 600/309 |
| 2007/0027427 A1 | 2/2007 | Trautman | 604/46 |
| 2007/0032812 A1 | 2/2007 | Loerwald | 606/181 |
| 2007/0032813 A1 | 2/2007 | Flynn | 606/181 |
| 2007/0038149 A1 | 2/2007 | Calasso | 600/583 |
| 2007/0038235 A1 | 2/2007 | Freeman | 606/181 |
| 2007/0043305 A1 | 2/2007 | Boecker | 600/583 |
| 2007/0043386 A1 | 2/2007 | Freeman | 606/181 |
| 2007/0049901 A1 | 3/2007 | Wu | 604/506 |
| 2007/0049959 A1 | 3/2007 | Feaster | 606/181 |
| 2007/0055174 A1 | 3/2007 | Freeman | 600/583 |
| 2007/0055297 A1 | 3/2007 | Fukuzawa | 606/181 |
| 2007/0055298 A1 | 3/2007 | Uehata | 606/181 |
| 2007/0060842 A1 | 3/2007 | Alvarez-Icaza | 600/583 |
| 2007/0060843 A1 | 3/2007 | Alvarez-Icaza | 600/583 |
| 2007/0060844 A1 | 3/2007 | Alvarez-Icaza | 600/583 |
| 2007/0060845 A1 | 3/2007 | Perez | 600/583 |
| 2007/0061393 A1 | 3/2007 | Chen | 205/777.5 |
| 2007/0062250 A1 | 3/2007 | Krulevitch | 73/1.16 |
| 2007/0062251 A1 | 3/2007 | Anex | 73/1.36 |

(56) References Cited

U.S. PATENT DOCUMENTS

| | | | |
|---|---|---|---|
| 2007/0062315 A1 | 3/2007 | Hodges | 73/864.72 |
| 2007/0064516 A1 | 3/2007 | Briggs | 365/230.05 |
| 2007/0066939 A1 | 3/2007 | Krulevitch | 604/152 |
| 2007/0066940 A1 | 3/2007 | Karunaratne | 604/152 |
| 2007/0068807 A1 | 3/2007 | Feldman | 204/403.01 |
| 2007/0073188 A1 | 3/2007 | Freeman | 600/583 |
| 2007/0073189 A1 | 3/2007 | Freeman | 600/583 |
| 2007/0074977 A1 | 4/2007 | Guo | 205/792 |
| 2007/0078358 A1 | 4/2007 | Escutia | 600/573 |
| 2007/0078360 A1 | 4/2007 | Matsumoto | 600/583 |
| 2007/0078474 A1 | 4/2007 | Kim | 606/181 |
| 2007/0080093 A1 | 4/2007 | Boozer | 206/569 |
| 2007/0083130 A1 | 4/2007 | Thomson | 600/583 |
| 2007/0083131 A1 | 4/2007 | Escutia | 600/583 |
| 2007/0083222 A1 | 4/2007 | Schraga | 606/181 |
| 2007/0083335 A1 | 4/2007 | Moerman | 702/19 |
| 2007/0084749 A1 | 4/2007 | Demelo | 206/569 |
| 2007/0088377 A1 | 4/2007 | LeVaughn | 606/181 |
| 2007/0092923 A1 | 4/2007 | Chang | 435/14 |
| 2007/0093728 A1 | 4/2007 | Douglas | 600/583 |
| 2007/0093752 A1 | 4/2007 | Zhao | 604/131 |
| 2007/0093753 A1 | 4/2007 | Krulevitch | 604/131 |
| 2007/0093863 A1 | 4/2007 | Pugh | 606/181 |
| 2007/0093864 A1 | 4/2007 | Pugh | 606/181 |
| 2007/0095178 A1 | 5/2007 | Schraga | 83/13 |
| 2007/0100255 A1 | 5/2007 | Boecker | 600/583 |
| 2007/0100256 A1 | 5/2007 | Sansom | 600/583 |
| 2007/0100364 A1 | 5/2007 | Sansom | 606/181 |
| 2007/0102312 A1 | 5/2007 | Cha | 206/363 |
| 2007/0106178 A1 | 5/2007 | Roe | 600/583 |
| 2007/0108048 A1 | 5/2007 | Wang | 204/403.01 |
| 2007/0112281 A1 | 5/2007 | Olson | 600/583 |
| 2007/0112367 A1 | 5/2007 | Olson | 606/181 |
| 2007/0118051 A1 | 5/2007 | Korner et al. | 600/583 |
| 2007/0119710 A1 | 5/2007 | Goldberger | 204/403.01 |
| 2007/0123801 A1 | 5/2007 | Goldberger | 600/583 |
| 2007/0123802 A1 | 5/2007 | Freeman | 600/583 |
| 2007/0123803 A1 | 5/2007 | Fujiwara et al. | 600/583 |
| 2007/0129618 A1 | 6/2007 | Goldberger | 600/345 |
| 2007/0129650 A1 | 6/2007 | Freeman | 600/583 |
| 2007/0131565 A1 | 6/2007 | Fujiwara | 205/777.5 |
| 2007/0135828 A1 | 6/2007 | Rutynowski | 606/181 |
| 2007/0142747 A1 | 6/2007 | Boecker | 600/583 |
| 2007/0142748 A1 | 6/2007 | Freeman | 600/583 |
| 2007/0142776 A9 | 6/2007 | Kovelman | 604/136 |
| 2007/0142854 A1 | 6/2007 | Schraga | 606/181 |
| 2007/0144235 A1 | 6/2007 | Werner | 73/1.82 |
| 2007/0149875 A1 | 6/2007 | Ouyang | 600/347 |
| 2007/0149897 A1 | 6/2007 | Ghesquiere | 600/583 |
| 2007/0161960 A1 | 7/2007 | Chen | 604/187 |
| 2007/0162064 A1 | 7/2007 | Starnes | 606/181 |
| 2007/0162065 A1 | 7/2007 | Li | 606/182 |
| 2007/0167869 A1 | 7/2007 | Roe | 600/583 |
| 2007/0167870 A1 | 7/2007 | Freeman | 600/583 |
| 2007/0167871 A1 | 7/2007 | Freeman | 600/583 |
| 2007/0167872 A1 | 7/2007 | Freeman | 600/583 |
| 2007/0167873 A1 | 7/2007 | Freeman | 600/583 |
| 2007/0167874 A1 | 7/2007 | Freeman | 600/583 |
| 2007/0167875 A1 | 7/2007 | Freeman | 600/583 |
| 2007/0173739 A1 | 7/2007 | Chan | 600/583 |
| 2007/0173740 A1 | 7/2007 | Chan | 600/583 |
| 2007/0173741 A1 | 7/2007 | Boeker | 600/583 |
| 2007/0173742 A1 | 7/2007 | Freeman | 600/583 |
| 2007/0173743 A1 | 7/2007 | Freeman | 600/583 |
| 2007/0173874 A1 | 7/2007 | Uschold | 606/181 |
| 2007/0173875 A1 | 7/2007 | Uschold | 606/181 |
| 2007/0173876 A1 | 7/2007 | Aylett | 606/181 |
| 2007/0176120 A1 | 8/2007 | Schwind | 250/492.1 |
| 2007/0179356 A1 | 8/2007 | Wessel | 600/300 |
| 2007/0179404 A1 | 8/2007 | Escutia | 600/583 |
| 2007/0179405 A1 | 8/2007 | Emery | 600/583 |
| 2007/0179406 A1 | 8/2007 | DeNuzzio | 600/583 |
| 2007/0182051 A1 | 8/2007 | Harttig | 264/138 |
| 2007/0185412 A1 | 8/2007 | Boecker | 600/583 |
| 2007/0185515 A1 | 8/2007 | Stout | 606/181 |
| 2007/0185516 A1 | 8/2007 | Schosnig | 606/181 |
| 2007/0191702 A1 | 8/2007 | Yodfat | 600/365 |
| 2007/0191737 A1 | 8/2007 | Freeman | 600/583 |
| 2007/0191738 A1 | 8/2007 | Raney | 600/583 |
| 2007/0191739 A1 | 8/2007 | Roe | 600/583 |
| 2007/0193019 A1 | 8/2007 | Feldman | 29/592.1 |
| 2007/0193882 A1 | 8/2007 | Dai | 204/403.02 |
| 2007/0196240 A1 | 8/2007 | Boozer | 422/102 |
| 2007/0196242 A1 | 8/2007 | Boozer | 422/102 |
| 2007/0203514 A1 | 8/2007 | Flaherty | 606/181 |
| 2007/0203903 A1 | 8/2007 | Attaran Rezaei | 707/5 |
| 2007/0205103 A1 | 9/2007 | Hodges | 204/403.01 |
| 2007/0207498 A1 | 9/2007 | Palmieri | 435/7.1 |
| 2007/0213601 A1 | 9/2007 | Freeman | 600/300 |
| 2007/0213637 A1 | 9/2007 | Boozer | 600/583 |
| 2007/0213682 A1 | 9/2007 | Haar | 604/500 |
| 2007/0213756 A1 | 9/2007 | Freeman | 606/181 |
| 2007/0218543 A1 | 9/2007 | Flaherty | 435/287.1 |
| 2007/0219346 A1 | 9/2007 | Trifiro | 530/308 |
| 2007/0219432 A1 | 9/2007 | Thompson | 600/300 |
| 2007/0219436 A1 | 9/2007 | Takase | 600/310 |
| 2007/0219462 A1 | 9/2007 | Briggs | 600/583 |
| 2007/0219463 A1 | 9/2007 | Briggs | 600/583 |
| 2007/0219572 A1 | 9/2007 | Deck | 606/181 |
| 2007/0219573 A1 | 9/2007 | Freeman | 606/183 |
| 2007/0219574 A1 | 9/2007 | Freeman | 606/185 |
| 2007/0225741 A1 | 9/2007 | Ikeda | 606/182 |
| 2007/0225742 A1 | 9/2007 | Abe | 606/182 |
| 2007/0227907 A1 | 10/2007 | Shah | 205/777.5 |
| 2007/0227911 A1 | 10/2007 | Wang | 205/792 |
| 2007/0227912 A1 | 10/2007 | Chatelier | 205/792 |
| 2007/0229085 A1 | 10/2007 | Kawai | 324/450 |
| 2007/0232872 A1 | 10/2007 | Prough | 600/316 |
| 2007/0232956 A1 | 10/2007 | Harman | 600/573 |
| 2007/0233013 A1 | 10/2007 | Schoenberg | 604/192 |
| 2007/0233166 A1 | 10/2007 | Stout | 606/182 |
| 2007/0233167 A1 | 10/2007 | Weiss | 606/182 |
| 2007/0233395 A1 | 10/2007 | Neel | 702/19 |
| 2007/0235329 A1 | 10/2007 | Harding | 204/403.01 |
| 2007/0235347 A1 | 10/2007 | Chatelier | 205/792 |
| 2007/0239068 A1 | 10/2007 | Rasch-Menges | 600/573 |
| 2007/0239188 A1 | 10/2007 | Boozer | 606/181 |
| 2007/0239189 A1 | 10/2007 | Freeman | 606/181 |
| 2007/0239190 A1 | 10/2007 | Alden | 606/181 |
| 2007/0240984 A1 | 10/2007 | Popovich | 204/403.01 |
| 2007/0240986 A1 | 10/2007 | Reymond | 204/412 |
| 2007/0244380 A1 | 10/2007 | Say | 600/347 |
| 2007/0244412 A1 | 10/2007 | Lav | 600/584 |
| 2007/0244498 A1 | 10/2007 | Steg | 606/181 |
| 2007/0244499 A1 | 10/2007 | Briggs | 606/182 |
| 2007/0249921 A1 | 10/2007 | Groll | 600/347 |
| 2007/0249962 A1 | 10/2007 | Alden | 600/583 |
| 2007/0249963 A1 | 10/2007 | Alden | 600/583 |
| 2007/0250099 A1 | 10/2007 | Flora | 606/181 |
| 2007/0251836 A1 | 11/2007 | Hsu | 205/792 |
| 2007/0254359 A1 | 11/2007 | Rezania | 435/325 |
| 2007/0255141 A1 | 11/2007 | Esenaliev | 600/475 |
| 2007/0255178 A1 | 11/2007 | Alvarez-Icaza | 600/583 |
| 2007/0255179 A1 | 11/2007 | Alvarez-Icaza | 600/583 |
| 2007/0255180 A1 | 11/2007 | Alvarez-Icaza | 600/583 |
| 2007/0255181 A1 | 11/2007 | Alvarez-Icaza | 600/583 |
| 2007/0255300 A1 | 11/2007 | Vanhiel | 606/181 |
| 2007/0255301 A1 | 11/2007 | Freeman | 606/181 |
| 2007/0255302 A1 | 11/2007 | Koeppel | 606/182 |
| 2007/0260271 A1 | 11/2007 | Freeman | 606/181 |
| 2007/0260272 A1 | 11/2007 | Weiss | 606/181 |
| 2007/0264721 A1 | 11/2007 | Buck | 436/150 |
| 2007/0265511 A1 | 11/2007 | Renouf | 600/319 |
| 2007/0265532 A1 | 11/2007 | Maynard | 600/477 |
| 2007/0265654 A1 | 11/2007 | Iio et al. | 606/185 |
| 2007/0273901 A1 | 11/2007 | Baskeyfield | 358/1.9 |
| 2007/0273903 A1 | 11/2007 | Baskeyfield | 358/1.9 |
| 2007/0273904 A1 | 11/2007 | Robinson | 358/1.9 |
| 2007/0273928 A1 | 11/2007 | Robinson | 358/1.9 |
| 2007/0276197 A1 | 11/2007 | Harmon | 600/300 |
| 2007/0276211 A1 | 11/2007 | Mir | 600/345 |
| 2007/0276290 A1 | 11/2007 | Boecker | 600/583 |
| 2007/0276425 A1 | 11/2007 | Kim | 606/186 |
| 2007/0276621 A1 | 11/2007 | Davies | 702/104 |

(56) References Cited

U.S. PATENT DOCUMENTS

| | | | |
|---|---|---|---|
| 2007/0278097 A1 | 12/2007 | Bhullar | 204/403.01 |
| 2007/0282186 A1 | 12/2007 | Gilmore | 600/365 |
| 2007/0282362 A1 | 12/2007 | Berg | 606/181 |
| 2007/0288047 A1 | 12/2007 | Thoes | 606/182 |
| 2007/0293743 A1 | 12/2007 | Monfre | 600/316 |
| 2007/0293744 A1 | 12/2007 | Monfre | 600/316 |
| 2007/0293790 A1 | 12/2007 | Bainczyk | 600/583 |
| 2007/0293882 A1 | 12/2007 | Harttig | 606/181 |
| 2007/0293883 A1 | 12/2007 | Horie | 606/181 |
| 2007/0295616 A1 | 12/2007 | Harding | 205/777.5 |
| 2008/0004651 A1 | 1/2008 | Nicholls | 606/182 |
| 2008/0007141 A1 | 1/2008 | Deck | 310/328 |
| 2008/0009767 A1 | 1/2008 | Effenhauser | 600/583 |
| 2008/0009768 A1 | 1/2008 | Sohrab | 600/583 |
| 2008/0009892 A1 | 1/2008 | Freeman | 606/181 |
| 2008/0009893 A1 | 1/2008 | LeVaughn | 606/181 |
| 2008/0015425 A1 | 1/2008 | Douglas | 600/347 |
| 2008/0015623 A1 | 1/2008 | Deck | 606/181 |
| 2008/0017522 A1 | 1/2008 | Heller | 205/777.5 |
| 2008/0019870 A1 | 1/2008 | Newman | 422/68.1 |
| 2008/0021291 A1 | 1/2008 | Zocchi | 600/300 |
| 2008/0021293 A1 | 1/2008 | Schurman | 600/316 |
| 2008/0021295 A1 | 1/2008 | Wang | 600/347 |
| 2008/0021296 A1 | 1/2008 | Creaven | 600/365 |
| 2008/0021346 A1 | 1/2008 | Haar | 600/583 |
| 2008/0021490 A1 | 1/2008 | Briggs | 606/181 |
| 2008/0021491 A1 | 1/2008 | Freeman | 606/181 |
| 2008/0021492 A1 | 1/2008 | Freeman | 606/181 |
| 2008/0021493 A1 | 1/2008 | Levaughn | 606/181 |
| 2008/0021494 A1 | 1/2008 | Schmelzeisen | 606/181 |
| 2008/0027385 A1 | 1/2008 | Freeman | 604/117 |
| 2008/0031778 A1 | 2/2008 | Kramer | 422/68.1 |
| 2008/0033268 A1 | 2/2008 | Stafford | 600/345 |
| 2008/0033318 A1 | 2/2008 | Mace | 600/583 |
| 2008/0033319 A1 | 2/2008 | Kloepfer | 600/583 |
| 2008/0033468 A1 | 2/2008 | Lathrop | 606/181 |
| 2008/0033469 A1 | 2/2008 | Winheim | 606/181 |
| 2008/0034834 A1 | 2/2008 | Schell | 73/1.02 |
| 2008/0034835 A1 | 2/2008 | Schell | 73/1.02 |
| 2008/0039885 A1 | 2/2008 | Purcell | 606/182 |
| 2008/0039886 A1 | 2/2008 | Shi | 606/182 |
| 2008/0039887 A1 | 2/2008 | Conway | 606/182 |
| 2008/0040919 A1 | 2/2008 | Griss | 29/777 |
| 2008/0045825 A1 | 2/2008 | Melker | 600/365 |
| 2008/0045992 A1 | 2/2008 | Schraga | 606/182 |
| 2008/0047764 A1 | 2/2008 | Lee | G08C 21/00 |
| 2008/0053201 A1 | 3/2008 | Roesicke | 73/61.41 |
| 2008/0057484 A1 | 3/2008 | Miyata | 434/739 |
| 2008/0058624 A1 | 3/2008 | Smart | 600/345 |
| 2008/0058626 A1 | 3/2008 | Miyata | 600/365 |
| 2008/0058631 A1 | 3/2008 | Draudt | 600/385 |
| 2008/0058847 A1 | 3/2008 | Abe | 606/181 |
| 2008/0058848 A1 | 3/2008 | Griffin | 606/182 |
| 2008/0058849 A1 | 3/2008 | Conway | 606/183 |
| 2008/0060424 A1 | 3/2008 | Babic | 73/61.41 |
| 2008/0064986 A1 | 3/2008 | Kraemer | 600/583 |
| 2008/0064987 A1 | 3/2008 | Escutia | 600/583 |
| 2008/0065130 A1 | 3/2008 | Patel | 606/181 |
| 2008/0065131 A1 | 3/2008 | List | 606/181 |
| 2008/0065132 A1 | 3/2008 | Trissel | 606/182 |
| 2008/0065133 A1 | 3/2008 | Kennedy | 606/182 |
| 2008/0065134 A1 | 3/2008 | Conway | 606/182 |
| 2008/0073224 A1 | 3/2008 | Diamond | 205/775 |
| 2008/0077048 A1 | 3/2008 | Escutia | 600/583 |
| 2008/0077167 A1 | 3/2008 | Flynn | 606/172 |
| 2008/0077168 A1 | 3/2008 | Nicholls | 606/182 |
| 2008/0081969 A1 | 4/2008 | Feldman | 600/322 |
| 2008/0081976 A1 | 4/2008 | Hodges | 600/345 |
| 2008/0082023 A1 | 4/2008 | Deck | 600/583 |
| 2008/0082116 A1 | 4/2008 | Lathrop | 606/181 |
| 2008/0082117 A1 | 4/2008 | Ruf | 606/182 |
| 2008/0086042 A1 | 4/2008 | Brister | 600/347 |
| 2008/0086044 A1 | 4/2008 | Brister | 600/365 |
| 2008/0086273 A1 | 4/2008 | Shults | 702/19 |
| 2008/0093227 A1 | 4/2008 | Diamond | 205/775 |
| 2008/0093228 A1 | 4/2008 | Diamond | 205/782 |
| 2008/0093230 A1 | 4/2008 | Diamond | 205/792 |
| 2008/0094804 A1 | 4/2008 | Reynolds | 361/727 |
| 2008/0097171 A1 | 4/2008 | Smart | 600/309 |
| 2008/0097241 A1 | 4/2008 | Maltezos | 600/576 |
| 2008/0097503 A1 | 4/2008 | Creaven | 606/182 |
| 2008/0098802 A1 | 5/2008 | Burke | 73/61.61 |
| 2008/0103396 A1 | 5/2008 | Johnson | 600/477 |
| 2008/0103415 A1 | 5/2008 | Roe | 600/583 |
| 2008/0103517 A1 | 5/2008 | Takemoto | 606/182 |
| 2008/0105024 A1 | 5/2008 | Creaven | 73/1.02 |
| 2008/0105568 A1 | 5/2008 | Wu | 205/780.5 |
| 2008/0108130 A1 | 5/2008 | Nakaminami | 435/287.1 |
| 2008/0108942 A1 | 5/2008 | Brister | 604/118 |
| 2008/0109024 A1 | 5/2008 | Berkovitch | 606/181 |
| 2008/0109025 A1 | 5/2008 | Yang | 606/182 |
| 2008/0109259 A1 | 5/2008 | Thompson | 705/3 |
| 2008/0114227 A1 | 5/2008 | Haar | 600/347 |
| 2008/0114228 A1 | 5/2008 | McCluskey | 600/365 |
| 2008/0118400 A1 | 5/2008 | Neel | 422/68.1 |
| 2008/0119703 A1 | 5/2008 | Brister | 600/347 |
| 2008/0119704 A1 | 5/2008 | Brister | 600/347 |
| 2008/0119706 A1 | 5/2008 | Brister | 600/365 |
| 2008/0119761 A1 | 5/2008 | Boecker | 600/583 |
| 2008/0119883 A1 | 5/2008 | Conway | 606/181 |
| 2008/0119884 A1 | 5/2008 | Flora | 606/182 |
| 2008/0121533 A1 | 5/2008 | Hodges | 205/775 |
| 2008/0125800 A1 | 5/2008 | List | 606/181 |
| 2008/0125801 A1 | 5/2008 | List | 606/181 |
| 2008/0134806 A1 | 6/2008 | Capriccio | 73/863.21 |
| 2008/0134810 A1 | 6/2008 | Neel | 73/866 |
| 2008/0135559 A1 | 6/2008 | Byrd | 220/506 |
| 2008/0140105 A1 | 6/2008 | Zhong | 606/182 |
| 2008/0144022 A1 | 6/2008 | Schulat | 356/213 |
| 2008/0146899 A1 | 6/2008 | Ruchti | 600/316 |
| 2008/0146966 A1 | 6/2008 | LeVaughn | 600/583 |
| 2008/0147108 A1 | 6/2008 | Kennedy | 606/182 |
| 2008/0149268 A1 | 6/2008 | Zhao | 156/299 |
| 2008/0149599 A1 | 6/2008 | Bohm | 216/94 |
| 2008/0152507 A1 | 6/2008 | Bohm | 417/44.1 |
| 2008/0154187 A1 | 6/2008 | Krulevitch | 604/48 |
| 2008/0154513 A1 | 6/2008 | Kovatchev | 702/19 |
| 2008/0159913 A1 | 7/2008 | Jung | 422/57 |
| 2008/0161664 A1 | 7/2008 | Mastrototaro | 600/347 |
| 2008/0161724 A1 | 7/2008 | Roe | 600/583 |
| 2008/0161725 A1 | 7/2008 | Wong | 600/583 |
| 2008/0166269 A1 | 7/2008 | Jansen | 422/63 |
| 2008/0167578 A1 | 7/2008 | Bryer | 600/583 |
| 2008/0167673 A1 | 7/2008 | Zhong | 606/181 |
| 2008/0188771 A1 | 8/2008 | Boecker | 600/583 |
| 2008/0194987 A1 | 8/2008 | Boecker | 600/583 |
| 2008/0194989 A1 | 8/2008 | Briggs | 600/583 |
| 2008/0200782 A1 | 8/2008 | Planman et al. | |
| 2008/0208026 A1 | 8/2008 | Noujaim | 600/365 |
| 2008/0208079 A1 | 8/2008 | Hein | 600/583 |
| 2008/0210574 A1 | 9/2008 | Boecker | 205/777.5 |
| 2008/0214909 A1 | 9/2008 | Fuerst | 600/309 |
| 2008/0214917 A1 | 9/2008 | Boecker | 600/347 |
| 2008/0214919 A1 | 9/2008 | Harmon | 600/365 |
| 2008/0214956 A1 | 9/2008 | Briggs | 600/575 |
| 2008/0228212 A1 | 9/2008 | List | 606/182 |
| 2008/0249435 A1 | 10/2008 | Haar | 600/583 |
| 2008/0249554 A1 | 10/2008 | Freeman | 606/181 |
| 2008/0255598 A1 | 10/2008 | LeVaughn et al. | 606/183 |
| 2008/0262387 A1 | 10/2008 | List | 600/583 |
| 2008/0262388 A1 | 10/2008 | List | 600/583 |
| 2008/0267822 A1 | 10/2008 | List | 422/68.1 |
| 2008/0269723 A1 | 10/2008 | Mastrototaro | 604/890.1 |
| 2008/0269791 A1 | 10/2008 | Hoenes | 606/181 |
| 2008/0275365 A1 | 11/2008 | Guthrie | 600/584 |
| 2008/0275384 A1 | 11/2008 | Mastrototaro | 604/66 |
| 2008/0277291 A1 | 11/2008 | Heller | 205/777.5 |
| 2008/0277292 A1 | 11/2008 | Heller | 205/777.5 |
| 2008/0277293 A1 | 11/2008 | Heller | 205/777.5 |
| 2008/0277294 A1 | 11/2008 | Heller | 205/777.5 |
| 2008/0286149 A1 | 11/2008 | Roe | 422/58 |
| 2008/0294068 A1 | 11/2008 | Briggs | 600/583 |
| 2008/0300614 A1 | 12/2008 | Freeman | 606/181 |
| 2008/0318193 A1 | 12/2008 | Alvarez-Icaza | 434/262 |

(56) References Cited

U.S. PATENT DOCUMENTS

| | | | |
|---|---|---|---|
| 2008/0319284 A1 | 12/2008 | Alvarez-Icaza | 600/309 |
| 2008/0319291 A1 | 12/2008 | Freeman | 600/347 |
| 2009/0005664 A1 | 1/2009 | Freeman | 600/347 |
| 2009/0020438 A1 | 1/2009 | Hodges | 205/782 |
| 2009/0024009 A1 | 1/2009 | Freeman | 600/309 |
| 2009/0024059 A1 | 1/2009 | Hoerauf | 600/583 |
| 2009/0026075 A1 | 1/2009 | Harding | 204/403.14 |
| 2009/0026091 A1 | 1/2009 | Harding | 205/777.5 |
| 2009/0027040 A1 | 1/2009 | Kermani | 324/123 |
| 2009/0029479 A1 | 1/2009 | Docherty | 436/149 |
| 2009/0043177 A1 | 2/2009 | Milledge | 600/309 |
| 2009/0043183 A1 | 2/2009 | Kermani | 600/365 |
| 2009/0048536 A1 | 2/2009 | Freeman | 600/583 |
| 2009/0054813 A1 | 2/2009 | Freeman | 600/584 |
| 2009/0057146 A1 | 3/2009 | Teodorczyk | 204/403.01 |
| 2009/0069716 A1 | 3/2009 | Freeman | 600/583 |
| 2009/0076415 A1 | 3/2009 | Moerman | |
| 2009/0084687 A1 | 4/2009 | Chatelier | 205/792 |
| 2009/0099477 A1 | 4/2009 | Hoenes et al. | |
| 2009/0105572 A1 | 4/2009 | Malecha | 600/365 |
| 2009/0105573 A1 | 4/2009 | Malecha | 600/365 |
| 2009/0112123 A1 | 4/2009 | Freeman | 600/583 |
| 2009/0112155 A1 | 4/2009 | Zhao | 604/67 |
| 2009/0112180 A1 | 4/2009 | Krulevitch | 604/506 |
| 2009/0112185 A1 | 4/2009 | Krulevitch | 604/523 |
| 2009/0112247 A1 | 4/2009 | Freeman et al. | |
| 2009/0118752 A1 | 5/2009 | Perez et al. | |
| 2009/0119760 A1 | 5/2009 | Hung et al. | |
| 2009/0124932 A1 | 5/2009 | Freeman | 606/181 |
| 2009/0131829 A1 | 5/2009 | Freeman | 600/583 |
| 2009/0131830 A1 | 5/2009 | Freeman | 600/583 |
| 2009/0131964 A1 | 5/2009 | Freeman | 606/181 |
| 2009/0131965 A1 | 5/2009 | Freeman | 606/181 |
| 2009/0137930 A1 | 5/2009 | Freeman | 600/583 |
| 2009/0138032 A1 | 5/2009 | Freeman | 606/181 |
| 2009/0139300 A1 | 6/2009 | Pugh | 73/1.36 |
| 2009/0177117 A1 | 7/2009 | Amano et al. | 600/583 |
| 2009/0184004 A1 | 7/2009 | Chatelier | 205/777.5 |
| 2009/0187351 A1 | 7/2009 | Orr | 702/19 |
| 2009/0192410 A1 | 7/2009 | Freeman | 600/583 |
| 2009/0192411 A1 | 7/2009 | Freeman | 600/583 |
| 2009/0196580 A1 | 8/2009 | Freeman | 386/124 |
| 2009/0204025 A1 | 8/2009 | Marsot | 600/573 |
| 2009/0216100 A1 | 8/2009 | Ebner | 600/347 |
| 2009/0237262 A1 | 9/2009 | Smith | 340/634 |
| 2009/0240127 A1 | 9/2009 | Pinaki | 600/365 |
| 2009/0247838 A1 | 10/2009 | Cummings | 600/309 |
| 2009/0247982 A1 | 10/2009 | Krulevitch | 604/500 |
| 2009/0259146 A1 | 10/2009 | Freeman | 600/583 |
| 2009/0270765 A1 | 10/2009 | Ghesquiere et al. | |
| 2009/0275860 A1 | 11/2009 | Nakamura et al. | |
| 2009/0280551 A1 | 11/2009 | Cardosi | 435/190 |
| 2009/0281457 A1 | 11/2009 | Faulkner | 600/583 |
| 2009/0281458 A1 | 11/2009 | Faulkner | 600/583 |
| 2009/0281459 A1 | 11/2009 | Faulkner | 600/583 |
| 2009/0301899 A1 | 12/2009 | Hodges | 205/777.5 |
| 2009/0302872 A1 | 12/2009 | Haggett | 324/715 |
| 2009/0302873 A1 | 12/2009 | Haggett | 324/724 |
| 2009/0322630 A1 | 12/2009 | Friman | 343/720 |
| 2009/0325307 A1 | 12/2009 | Haggett | 436/150 |
| 2010/0016700 A1 | 1/2010 | Sieh | 600/365 |
| 2010/0018878 A1 | 1/2010 | Davies | 205/782 |
| 2010/0030110 A1 | 2/2010 | Choi | 600/583 |
| 2010/0041084 A1 | 2/2010 | Stephens | 435/14 |
| 2010/0094170 A1 | 4/2010 | Wilson et al. | |
| 2010/0094172 A1* | 4/2010 | List et al. | A61B 5/15146 600/583 |
| 2010/0094324 A1 | 4/2010 | Huang et al. | |
| 2010/0113981 A1 | 5/2010 | Oki et al. | 600/587 |
| 2010/0145377 A1 | 6/2010 | Lai et al. | |
| 2010/0198107 A1 | 8/2010 | Groll et al. | 600/583 |
| 2010/0210970 A1 | 8/2010 | Horikawa et al. | |
| 2010/0256525 A1 | 10/2010 | List et al. | 600/583 |
| 2010/0274273 A1 | 10/2010 | Schraga et al. | |
| 2010/0292611 A1 | 11/2010 | Lum et al. | |
| 2010/0324452 A1 | 12/2010 | Freeman et al. | 600/583 |
| 2010/0324582 A1 | 12/2010 | Nicholls et al. | |
| 2011/0041449 A1 | 2/2011 | Espinosa | |
| 2011/0077478 A1 | 3/2011 | Freeman et al. | |
| 2011/0077553 A1 | 3/2011 | Alroy | 600/573 |
| 2011/0098541 A1 | 4/2011 | Freeman et al. | 600/309 |
| 2011/0178429 A1 | 7/2011 | Jacobs | |
| 2011/0184448 A1 | 7/2011 | Brown et al. | |
| 2012/0149999 A1 | 6/2012 | Freeman et al. | 600/309 |
| 2012/0184876 A1 | 7/2012 | Freeman et al. | |
| 2012/0232425 A1 | 9/2012 | Freeman et al. | 600/583 |
| 2012/0271197 A1 | 10/2012 | Castle et al. | 600/583 |
| 2012/0296233 A9 | 11/2012 | Freeman | 600/583 |
| 2013/0261500 A1 | 10/2013 | Jacobs | |

FOREIGN PATENT DOCUMENTS

| | | | | |
|---|---|---|---|---|
| DE | 3538313 A1 | 4/1986 | | B08B 5/02 |
| DE | 4212315 A1 | 10/1993 | | A61B 5/14 |
| DE | 4320347 | 12/1994 | | C07D 239/82 |
| DE | 4344452 | 6/1995 | | C07D 471/04 |
| DE | 4420232 | 12/1995 | | |
| DE | 29800611 U | 7/1998 | | A61B 17/32 |
| DE | 19819407 | 11/1999 | | G01N 33/48 |
| DE | 200 09 475 | 9/2000 | | |
| DE | 20009475 | 10/2000 | | A61B 5/15 |
| DE | 29824204 | 10/2000 | | G01N 33/48 |
| DE | 10053974 | 12/2000 | | A61M 1/00 |
| DE | 10032042 | 1/2002 | | G01N 27/327 |
| DE | 10057832 | 2/2002 | | |
| DE | 10142232 | 3/2003 | | A61B 5/15 |
| DE | 10208575 | 8/2003 | | |
| DE | 10208575 C1 | 8/2003 | | |
| DE | 10245721 | 12/2003 | | |
| DE | 10361560 | 7/2005 | | |
| EP | 0112498 A2 | 7/1984 | | A47L 1/00 |
| EP | 137975 A2 | 4/1985 | | A61B 5/14 |
| EP | 0160768 | 11/1985 | | A61B 5/00 |
| EP | 199484 | 10/1986 | | |
| EP | 0199484 A2 | 10/1986 | | |
| EP | 0254246 | 1/1988 | | G01N 21/03 |
| EP | 0289 269 | 11/1988 | | G01N 27/40 |
| EP | 0317847 A1 | 5/1989 | | A61B 5/14 |
| EP | 0320109 | 6/1989 | | A61B 5/00 |
| EP | 359831 | 3/1990 | | |
| EP | 364208 | 4/1990 | | |
| EP | 0364208 A1 | 4/1990 | | |
| EP | 0170375 | 5/1990 | | G01N 33/48 |
| EP | 0136362 | 12/1990 | | G01N 27/327 |
| EP | 406304 | 1/1991 | | |
| EP | 0449525 | 10/1991 | | A61B 5/14 |
| EP | 0453283 | 10/1991 | | A61B 5/00 |
| EP | 0449147 A2 | 8/1992 | | A61M 5/32 |
| EP | 505475 | 9/1992 | | |
| EP | 505494 | 9/1992 | | |
| EP | 505504 | 9/1992 | | |
| EP | 0530994 | 3/1993 | | C07D 239/80 |
| EP | 0374355 | 6/1993 | | A61M 37/00 |
| EP | 552223 | 7/1993 | | |
| EP | 0351891 | 9/1993 | | G01N 27/30 |
| EP | 0593096 | 4/1994 | | G01N 27/327 |
| EP | 0630609 A2 | 12/1994 | | A61B 5/14 |
| EP | 0415388 | 5/1995 | | G01N 27/237 |
| EP | 0654659 | 5/1995 | | G01N 3/52 |
| EP | 0505494 | 7/1995 | | C12M 1/40 |
| EP | 0662367 A1 | 7/1995 | | B24C 1/00 |
| EP | 0359831 | 8/1995 | | G01N 27/28 |
| EP | 0471986 | 10/1995 | | C12M 1/40 |
| EP | 0368474 | 12/1995 | | C12M 1/40 |
| EP | 0461601 | 12/1995 | | C12Q 1/00 |
| EP | 0429076 | 1/1996 | | C12M 1/140 |
| EP | 0552223 | 7/1996 | | G01N 33/48 |
| EP | 0735363 | 10/1996 | | G01N 27/327 |
| EP | 759553 | 2/1997 | | |
| EP | 0505504 | 3/1997 | | G01R 27/02 |
| EP | 0777123 | 6/1997 | | G01N 33/487 |
| EP | 0406304 | 8/1997 | | C12Q 1/00 |
| EP | 0537761 | 8/1997 | | C12M 1/40 |
| EP | 0795601 | 9/1997 | | |

(56) References Cited

FOREIGN PATENT DOCUMENTS

| | | | |
|---|---|---|---|
| EP | 0562370 | 11/1997 | ........... G01N 27/327 |
| EP | 0415393 | 12/1997 | ............. G01N 27/38 |
| EP | 817809 | 1/1998 | |
| EP | 0823239 | 2/1998 | .............. A61N 1/36 |
| EP | 0560336 | 5/1998 | ............. C12M 1/40 |
| EP | 847447 | 6/1998 | |
| EP | 0878 708 | 11/1998 | ........... G01N 27/327 |
| EP | 874984 | 11/1998 | |
| EP | 0505475 | 3/1999 | ............ G06F 19/00 |
| EP | 898936 | 3/1999 | |
| EP | 0898936 A2 | 3/1999 | |
| EP | 0901018 | 3/1999 | ............. G01N 33/48 |
| EP | 0470649 | 6/1999 | ............. G01N 27/42 |
| EP | 937249 | 8/1999 | |
| EP | 938493 | 9/1999 | |
| EP | 951939 | 10/1999 | |
| EP | 0951939 A2 | 10/1999 | |
| EP | 0847447 | 11/1999 | ............. C12Q 1/00 |
| EP | 0964059 | 12/1999 | ............. C12Q 1/00 |
| EP | 0964060 | 12/1999 | ............. C12Q 1/00 |
| EP | 0969097 | 1/2000 | ............. C12Q 1/00 |
| EP | 985376 | 3/2000 | |
| EP | 0985376 A1 | 3/2000 | |
| EP | 1021950 | 7/2000 | .............. A01K 11/00 |
| EP | 0894869 | 2/2001 | ............... C12Q 1/00 |
| EP | 1074832 | 2/2001 | ........... G01N 27/327 |
| EP | 1093854 | 4/2001 | ............... B01L 3/00 |
| EP | 1101443 A2 | 5/2001 | |
| EP | 1114995 | 7/2001 | ............. G01N 33/487 |
| EP | 0736607 | 8/2001 | ........... G01N 27/327 |
| EP | 1 157 660 | 11/2001 | |
| EP | 1157660 | 11/2001 | .............. A61B 5/15 |
| EP | 0730037 | 12/2001 | ............. C12Q 1/26 |
| EP | 0636879 | 1/2002 | ........... G01N 27/327 |
| EP | 1174083 | 1/2002 | |
| EP | 0851224 | 3/2002 | ........... G01N 27/327 |
| EP | 0856586 | 5/2002 | ............. C12Q 1/00 |
| EP | 0817809 | 7/2002 | ............ C08G 77/26 |
| EP | 0872728 | 7/2002 | ........... G01N 27/327 |
| EP | 0795748 | 8/2002 | ........... G01N 27/327 |
| EP | 0685737 | 9/2002 | ........... G01N 27/327 |
| EP | 1337182 | 8/2003 | |
| EP | 0880692 | 1/2004 | ........... G01N 27/327 |
| EP | 1374770 | 2/2004 | |
| EP | 1401233 | 4/2004 | |
| EP | 1404232 | 4/2004 | |
| EP | 1404233 | 4/2004 | .............. A61B 5/15 |
| EP | 1246688 | 5/2004 | ............ B01D 71/10 |
| EP | 1486766 | 12/2004 | ............... G01N 1/00 |
| EP | 1492457 A1 | 1/2005 | |
| EP | 1502614 | 2/2005 | |
| EP | 1643908 | 4/2006 | |
| EP | 1779780 A2 | 5/2007 | |
| EP | 1790288 | 5/2007 | .............. A61B 5/151 |
| EP | 1790288 A1 | 5/2007 | |
| EP | 1881322 A1 | 1/2008 | ........... G01N 33/487 |
| EP | 1921992 | 5/2008 | |
| EP | 2039294 | 3/2009 | .............. A61B 5/151 |
| EP | 2039294 A1 | 3/2009 | |
| EP | 2119396 A1 | 11/2009 | |
| EP | 2130493 A1 | 12/2009 | .............. A61B 5/15 |
| FR | 2555432 | 5/1985 | |
| FR | 2622457 | 11/1987 | .............. A61M 5/20 |
| GB | 1558111 | 12/1979 | .............. A61B 5/05 |
| GB | 2168815 | 6/1986 | ............. G01N 27/30 |
| GB | 2331936 | 6/1999 | |
| GB | 2335860 | 10/1999 | |
| GB | 2335990 | 10/1999 | |
| JP | 04-194660 | 7/1992 | |
| JP | 194660 | 7/1992 | ............. G01N 27/28 |
| JP | 1996010208 | 12/1992 | ........... G01N 27/327 |
| JP | 9-276235 | 10/1997 | ............. A61B 5/00 |
| JP | 10-104906 | 1/1998 | |
| JP | 1014906 | 1/1998 | ............. A61B 5/14 |
| JP | 2000-116768 | 4/2000 | ............. A61M 1/02 |
| JP | 2009082631 A | 4/2009 | |
| WO | WO 80/01389 | 7/1980 | ............. C12Q 1/54 |
| WO | WO 85/04089 | 9/1985 | .............. A61B 5/14 |
| WO | WO 86/07632 | 12/1985 | ............. G01N 27/30 |
| WO | WO86/05966 | 10/1986 | .............. A61B 5/00 |
| WO | WO 91/09139 | 6/1991 | ............. C12Q 1/54 |
| WO | WO92/03099 | 3/1992 | ............. A61B 17/32 |
| WO | WO92/06971 | 4/1992 | ........... C07D 401/06 |
| WO | WO92/07263 | 4/1992 | ............. C12Q 1/00 |
| WO | WO92/07468 | 5/1992 | ............. A01N 43/90 |
| WO | WO93/00044 | 1/1993 | ............. A61B 17/32 |
| WO | WO 93/02720 | 2/1993 | .............. A61M 5/00 |
| WO | WO 93/06979 | 4/1993 | ............... B26F 1/24 |
| WO | WO93/09723 | 5/1993 | ............. A61B 17/32 |
| WO | WO 93/12726 | 7/1993 | ............. A61B 17/34 |
| WO | WO 93/25898 | 12/1993 | ........... G01N 27/327 |
| WO | WO 94/27140 | 11/1994 | ........... G01N 27/327 |
| WO | WO 94/29703 | 12/1994 | ............. G01N 27/26 |
| WO | WO 94/29704 | 12/1994 | ............. G01N 27/26 |
| WO | WO 94/29731 | 12/1994 | ............. G01N 33/86 |
| WO | WO 95/00662 | 1/1995 | ............. C12Q 1/26 |
| WO | WO 95/06240 | 3/1995 | |
| WO | WO 95/10223 | 4/1995 | |
| WO | WO95/012583 | 5/1995 | ........... C07D 239/80 |
| WO | WO 95/22597 | 8/1995 | ............. C12M 1/40 |
| WO | WO96/14799 | 5/1996 | ............. A61B 17/32 |
| WO | WO 96/30431 | 10/1996 | ............ C08G 77/26 |
| WO | WO96/37148 | 11/1996 | .............. A61B 5/15 |
| WO | WO 97/02359 | 1/1997 | ........... G01N 27/327 |
| WO | WO 97/02487 | 1/1997 | ........... G01N 27/327 |
| WO | WO 97/11883 | 4/1997 | ............... B65B 1/00 |
| WO | WO 97/11883 A1 | 4/1997 | |
| WO | WO 97/18464 | 5/1997 | ........... G01N 27/403 |
| WO | WO97/028741 | 8/1997 | .............. A61B 5/15 |
| WO | WO 97/30344 | 8/1997 | ............. C12Q 1/00 |
| WO | WO 97/42882 | 11/1997 | ............. A61B 17/14 |
| WO | WO 97/42888 | 11/1997 | .............. A61B 5/00 |
| WO | WO 97/45720 | 12/1997 | ........... G01N 27/327 |
| WO | WO 98/03431 | 1/1998 | .............. C01G 5/02 |
| WO | WO98/14436 | 4/1998 | ............ C07B 59/00 |
| WO | WO 98/19159 | 5/1998 | ............. G01N 33/52 |
| WO | WO98/19609 | 5/1998 | ............. A61B 17/32 |
| WO | WO 98/20332 | 5/1998 | ........... G01N 27/327 |
| WO | WO 98/20348 | 5/1998 | ............. G01N 33/52 |
| WO | WO98/20867 | 5/1998 | ............. A61K 31/00 |
| WO | WO 98/24366 | 6/1998 | |
| WO | WO 98 24373 | 6/1998 | |
| WO | WO 98/35225 | 8/1998 | ........... G01N 27/327 |
| WO | WO98/45276 | 10/1998 | ........... C07D 239/80 |
| WO | WO 99/03584 | 1/1999 | ............... B01L 3/00 |
| WO | WO 99/05966 | 2/1999 | .............. A61B 5/14 |
| WO | WO99/07295 | 2/1999 | |
| WO | WO 99/07431 | 2/1999 | |
| WO | WO 99/13100 | 3/1999 | ............. C12Q 1/00 |
| WO | WO 99/62576 | 3/1999 | |
| WO | WO 99/19507 | 4/1999 | ............. G01N 27/30 |
| WO | WO 99/19717 | 4/1999 | ............. G01N 25/22 |
| WO | WO 99/27852 | 6/1999 | ............. A61B 5/103 |
| WO | WO 99/13100 | 12/1999 | |
| WO | WO 99/62576 | 12/1999 | ............. A61M 5/168 |
| WO | WO 99/64580 | 12/1999 | ............. C12N 15/00 |
| WO | WO 00/09184 | 2/2000 | |
| WO | WO 00/20626 | 4/2000 | ............. C12Q 1/00 |
| WO | WO00/29577 | 5/2000 | ........... C07K 14/705 |
| WO | WO 00/30186 | 5/2000 | ............. H01L 41/09 |
| WO | WO 00/39914 | 7/2000 | |
| WO | WO 00/44084 | 7/2000 | ............. H02K 37/12 |
| WO | WO00/46854 | 8/2000 | ............. G02F 1/1333 |
| WO | WO 00/50771 | 8/2000 | ............... F03G 7/00 |
| WO | WO00/55915 | 9/2000 | ............. H01L 21/98 |
| WO | WO 00/60340 | 10/2000 | ........... G01N 27/327 |
| WO | WO 00/64022 | 10/2000 | ............. H02H 3/33 |
| WO | WO 00/67245 | 11/2000 | |
| WO | WO 00/67268 | 11/2000 | ............. H01H 1/00 |
| WO | WO 01/00090 | 1/2001 | .............. A61B 5/15 |
| WO | WO 01/7220 A1 | 2/2001 | |
| WO | WO 01/15807 A1 | 3/2001 | |
| WO | WO 01/16578 A1 | 3/2001 | |
| WO | WO 01/75433 | 3/2001 | ............. G01N 33/00 |

(56) References Cited

FOREIGN PATENT DOCUMENTS

| | | | |
|---|---|---|---|
| WO | WO 01/23885 | 4/2001 | ........... G01N 33/487 |
| WO | WO 01/25775 | 4/2001 | .............. G01N 27/30 |
| WO | WO 01/26813 | 4/2001 | ................ B01L 3/00 |
| WO | WO01/29037 | 4/2001 | .............. A61K 31/44 |
| WO | WO 01/33216 | 5/2001 | ........... G01N 33/487 |
| WO | WO 01/34029 | 5/2001 | ............... A61B 5/15 |
| WO | WO 01/36955 | 5/2001 | ........... G01N 27/327 |
| WO | WO 01/45014 A1 | 6/2001 | |
| WO | WO 01/40788 | 7/2001 | ........... G01N 27/327 |
| WO | WO 01/57510 | 8/2001 | .............. G01N 27/30 |
| WO | WO 01/63271 | 8/2001 | ........... G01N 27/327 |
| WO | WO 01/64105 | 9/2001 | |
| WO | WO 01/66010 | 9/2001 | ............... A61B 5/15 |
| WO | WO-0166010 A1 | 9/2001 | |
| WO | WO 01/72225 | 10/2001 | ............... A61B 5/15 |
| WO | WO 01/73124 | 10/2001 | ................ C12Q 1/68 |
| WO | WO 01/73395 | 10/2001 | ................ G01N 1/00 |
| WO | WO 01/89691 | 11/2001 | |
| WO | WO 01/91634 A2 | 12/2001 | ............... A61B 5/00 |
| WO | WO 01/95806 | 12/2001 | ............... A61B 5/15 |
| WO | WO01/95806 | 12/2001 | ............... A61B 5/15 |
| WO | WO 02/00101 | 1/2002 | |
| WO | WO 02/02796 | 1/2002 | ................ C12Q 1/00 |
| WO | WO 02/08750 | 1/2002 | ............. G01N 33/487 |
| WO | WO 02/08753 | 1/2002 | ............. G01N 33/50 |
| WO | WO 02/08950 | 1/2002 | ............. G06F 17/20 |
| WO | WO 02/18940 | 3/2002 | ............. G01N 33/50 |
| WO | WO 02/32559 | 4/2002 | ............. B01D 71/10 |
| WO | WO 02/41779 | 5/2002 | ............... A61B 5/15 |
| WO | WO 02/44948 | 6/2002 | ............. G06F 17/30 |
| WO | WO 02/49507 | 6/2002 | ............. A61B 10/00 |
| WO | WO/0249507 | 6/2002 | ............. A61B 10/00 |
| WO | WO 02/056769 | 7/2002 | ............... A61B 5/00 |
| WO | WO 02/059734 | 8/2002 | ............... G06F 3/00 |
| WO | WO 02/069791 | 9/2002 | ............... A61B 5/00 |
| WO | WO 02/077638 | 10/2002 | |
| WO | WO 02/100251 | 12/2002 | |
| WO | WO 02/100252 | 12/2002 | |
| WO | WO 02/100253 | 12/2002 | |
| WO | WO 02/100254 | 12/2002 | |
| WO | WO 02/100460 | 12/2002 | |
| WO | WO 02/100461 | 12/2002 | |
| WO | WO 02/101343 | 12/2002 | |
| WO | WO 02/101359 | 12/2002 | |
| WO | WO 03/000321 | 1/2003 | ............... A61B 5/15 |
| WO | WO 03/023389 | 3/2003 | ............. G06F 17/30 |
| WO | WO 03/042691 | 5/2003 | ............... A61M 5/32 |
| WO | WO 03039369 A | 5/2003 | ............. A61B 10/00 |
| WO | WO 03/045557 | 6/2003 | ........... G01N 27/333 |
| WO | WO 03/046542 | 6/2003 | ........... G01N 33/487 |
| WO | WO 03/049609 | 6/2003 | |
| WO | WO 03/050534 | 6/2003 | ........... G01N 33/487 |
| WO | WO 03/066128 | 8/2003 | |
| WO | WO 03/070099 | 8/2003 | ............... A61B 5/15 |
| WO | WO 03/071940 | 9/2003 | ............... A61B 5/00 |
| WO | WO 03/082091 | 10/2003 | ............... A61B 5/00 |
| WO | WO 03/082091 A2 | 10/2003 | |
| WO | WO 03/088824 | 10/2003 | ............... A61B 5/15 |
| WO | WO 03/088834 | 10/2003 | ............... A61B 5/00 |
| WO | WO 03/088835 | 10/2003 | ............... A61B 5/15 |
| WO | WO/03088834 | 10/2003 | |
| WO | WO 2004/008130 | 1/2004 | ............. G01N 27/37 |
| WO | WO-2004017964 A1 | 3/2004 | |
| WO | WO 2004/026130 | 4/2004 | ............... A61B 5/00 |
| WO | WO 2004/041082 | 5/2004 | ............... A61B 5/00 |
| WO | WO 2004/045375 | 6/2004 | ............... A61B 5/15 |
| WO | WO 2004/054455 | 7/2004 | ............. A61B 17/32 |
| WO | WO 2004/060174 | 7/2004 | ............. A61B 17/14 |
| WO | WO 2004/060446 | 7/2004 | ............. G01N 21/76 |
| WO | WO 2004/091693 | 10/2004 | |
| WO | WO 2004/107964 | 12/2004 | |
| WO | WO 2004/107975 | 12/2004 | ............... A61B 5/00 |
| WO | WO 2004/112602 | 12/2004 | ............... A61B 5/00 |
| WO | WO 2004/112612 | 12/2004 | ............... A61B 5/15 |
| WO | WO 2004/112612 A1 | 12/2004 | |
| WO | WO-2004103147 A2 | 12/2004 | |
| WO | WO 2005/001418 | 1/2005 | |
| WO | WO 2005/013824 | 2/2005 | ............... A61B 5/15 |
| WO | WO 2005045414 A1 | 5/2005 | ................ C12Q 1/00 |
| WO | WO2005/084546 A2 | 9/2005 | ............... A61B 5/15 |
| WO | WO 2005/104948 | 11/2005 | ............... A61B 5/15 |
| WO | WO 2005/104948 A1 | 11/2005 | |
| WO | WO 2005/114185 | 12/2005 | ............. G01N 21/64 |
| WO | WO 2005/120197 | 12/2005 | ............. A61B 17/14 |
| WO | WO 2005/120199 | 12/2005 | ............... A61B 5/00 |
| WO | WO 2005/120365 | 12/2005 | ............. A61B 17/32 |
| WO | WO 2006/001797 | 1/2006 | ............. A61B 17/14 |
| WO | WO-2006005545 A1 | 1/2006 | |
| WO | WO 2006/015615 | 2/2006 | ................ C12Q 1/00 |
| WO | WO 2006/031920 | 3/2006 | ............... A61B 5/00 |
| WO | WO-2006037646 A2 | 4/2006 | |
| WO | WO 2006/105146 | 10/2006 | ............... A61B 5/05 |
| WO | WO 2006/116441 | 11/2006 | ............. A61B 5/151 |
| WO | WO 2007/010087 A2 | 1/2007 | ............. A61B 5/151 |
| WO | WO 2007/025635 | 3/2007 | ............... A61B 5/15 |
| WO | WO 2007/044834 | 4/2007 | ............... A61B 5/00 |
| WO | WO 2007/054335 | 5/2007 | ............... A61B 5/15 |
| WO | WO 2007/070719 | 6/2007 | ............... A61B 5/00 |
| WO | WO 2007/084367 | 7/2007 | ............... A61B 5/00 |
| WO | WO 2007/088905 A1 | 8/2007 | ........... A61B 5/1473 |
| WO | WO 2007/106470 | 9/2007 | ................ G01N 1/00 |
| WO | WO 2007/119900 | 10/2007 | ............. A61B 5/157 |
| WO | WO 2008/085052 A2 | 7/2008 | ............... A61B 5/15 |
| WO | WO 2008/112268 | 9/2008 | ............. A61B 17/32 |
| WO | WO 2008/112279 | 9/2008 | ............. A61B 5/155 |
| WO | WO-2008112268 A2 | 9/2008 | |
| WO | WO-2008112279 A1 | 9/2008 | |
| WO | WO 2010109461 A1 | 9/2010 | ............. A61B 5/151 |

OTHER PUBLICATIONS

G. Jarzabek, Z. Borkowska, On the Real Surface of Smooth Solid Electrodes, 1997, Electrochimica Acta, vol. 42, No. 19, pp. 2915-1918.

* cited by examiner

Puncture hole from patient side

Puncture hole from device side

METHOD AND APPARATUS FOR A FLUID SAMPLING DEVICE

CROSS-REFERENCE TO RELATED APPLICATIONS

This application is a continuation-in-part of U.S. Ser. No. 12/088,370 filed Mar. 27, 2008, which application is the U.S. national stage filing of PCT/US05/19445 filed Jun. 3, 2005, which application claims the benefit of U.S. Ser. Nos. 60/577,376 filed Jun. 30, 2004, and 60/577,412, filed Jun. 30, 2004, all of which applications are fully incorporated herein by reference.

TECHNICAL FIELD

The technical field relates to analyte detecting devices, and more specifically, device for obtaining a fluid sample.

BACKGROUND ART

Lancing devices are known in the medical health-care products industry for piercing the skin to produce blood for analysis. Typically, a drop of blood for this type of analysis is obtained by making a small incision in the fingertip, creating a small wound, which generates a small blood droplet on the surface of the skin.

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. The device may be held against the skin and mechanically triggered to ballistically launch the lancet. Unfortunately, the pain associated with each lancing event using known technology discourages patients from testing. In addition to vibratory stimulation of the skin as the driver impacts the end of a launcher stop, known spring based devices have the possibility of firing lancets that harmonically oscillate against the patient tissue, causing multiple strikes due to recoil. This recoil and multiple strikes of the lancet is one major impediment to patient compliance with a structured glucose monitoring regime.

Success rate generally encompasses the probability of producing a blood sample with one lancing action, which is sufficient in volume to perform the desired analytical test. The blood may appear spontaneously at the surface of the skin, or may be "milked" from the wound. Milking generally involves pressing the side of the digit, or in proximity of the wound to express the blood to the surface. In traditional methods, the blood droplet produced by the lancing action must reach the surface of the skin to be viable for testing.

When using existing methods, blood often flows from the cut blood vessels but is then trapped below the surface of the skin, forming a hematoma. In other instances, a wound is created, but no blood flows from the wound. In either case, the lancing process cannot be combined with the sample acquisition and testing step. Spontaneous blood droplet generation with current mechanical launching system varies between launcher types but on average it is about 50% of lancet strikes, which would be spontaneous. Otherwise milking is required to yield blood. Mechanical launchers are unlikely to provide the means for integrated sample acquisition and testing if one out of every two strikes does not yield a spontaneous blood sample.

Many diabetic patients (insulin dependent) are required to self-test for blood glucose levels five to six times daily. The large number of steps required in traditional methods of glucose testing ranging from lancing, to milking of blood, applying blood to the test strip, and getting the measurements from the test strip discourages many diabetic patients from testing their blood glucose levels as often as recommended. Tight control of plasma glucose through frequent testing is therefore mandatory for disease management. The pain associated with each lancing event further discourages patients from testing. Additionally, the wound channel left on the patient by known systems may also be of a size that discourages those who are active with their hands or who are worried about healing of those wound channels from testing their glucose levels.

Another problem frequently encountered by patients who must use lancing equipment to obtain and analyze blood samples is the amount of manual dexterity and hand-eye coordination required to properly operate the lancing and sample testing equipment due to retinopathies and neuropathies particularly, severe in elderly diabetic patients. For those patients, operating existing lancet and sample testing equipment can be a challenge. Once a blood droplet is created, that droplet must then be guided into a receiving channel of a small test strip or the like. If the sample placement on the strip is unsuccessful, repetition of the entire procedure including re-lancing the skin to obtain a new blood droplet is necessary.

Early methods of using test strips required a relatively substantial volume of blood to obtain an accurate glucose measurement. This large blood requirement made the monitoring experience a painful one for the user since the user may need to lance deeper than comfortable to obtain sufficient blood generation. Alternatively, if insufficient blood is spontaneously generated, the user may need to "milk" the wound to squeeze enough blood to the skin surface. Neither method is desirable as they take additional user effort and may be painful. The discomfort and inconvenience associated with such lancing events may deter a user from testing their blood glucose levels in a rigorous manner sufficient to control their diabetes.

A further impediment to patient compliance is the amount of time that at lower volumes, it becomes even more important that blood or other fluid sample be directed to a measurement device without being wasted or spilled along the way. Known devices do not effectively handle the low sample volumes in an efficient manner. Accordingly, improved sensing devices are desired to increase user compliance and reduce the hurdles associated with analyte measurement.

A further concern is the use of blood glucose monitoring devices in a professional setting. For the professional health care market, single device multiple user is the norm. A sterility barrier between patients is required or a single use professional lancing device is used and then discarded after use. To interface an integrated point of care lancing, sampling and analyte detection device with a multiple user paradigm, each lancet analyte detecting member pair may be isolated from the previous and subsequent user.

SUMMARY OF THE INVENTION

An object of the present invention is to provide an improved body fluid sampling apparatus that provides for the release of penetrating members from a disposable.

Another object of the present invention is to provide an improved body fluid sampling apparatus that has a mechanical assembly with a cam and is actuated by a manually actuated button.

Still another object of the present invention is to provide a body fluid sampling apparatus with a sweeper arm coupled to a gripper.

A further object of the present invention is to provide a body fluid sampling apparatus that has where a sweeper arm acts as a safety arm for penetrating members.

Yet another object of the present invention is to provide a body fluid sampling apparatus that has a finger interface section at an exterior of the housing.

These and other objects of the present invention are achieve in a blood analyzer device that has a housing with a top section coupled to a bottom section, a driver and a plurality of penetrating members housed in a disposable positionable in the housing. A gripper engages each of penetrating member with the driven prior to launch of a penetrating member during a lancing event. A manually actuated button advances the disposable to move penetrating members into launch positions. A power source is coupled to the driver. A display is positioned at the housing.

BRIEF DESCRIPTION OF THE DRAWINGS

FIGS. 18 through 21 are cut-away views of various elements of a device according to the present invention.

FIGS. 24-28 show various embodiments of a tissue interface.

DESCRIPTION OF THE SPECIFIC EMBODIMENTS

The present invention provides a solution for body fluid sampling. Specifically, some embodiments of the present invention provides a method for improving release of penetrating members for a disposable. The invention may use a high density penetrating member design. It may use penetrating members of smaller size, such as but not limited to diameter or length, than those of conventional penetrating members known in the art. The device may be used for multiple lancing events without having to remove a disposable from the device. The invention may provide improved sensing capabilities. At least some of these and other objectives described herein will be met by embodiments of the present invention.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

Figure 1:
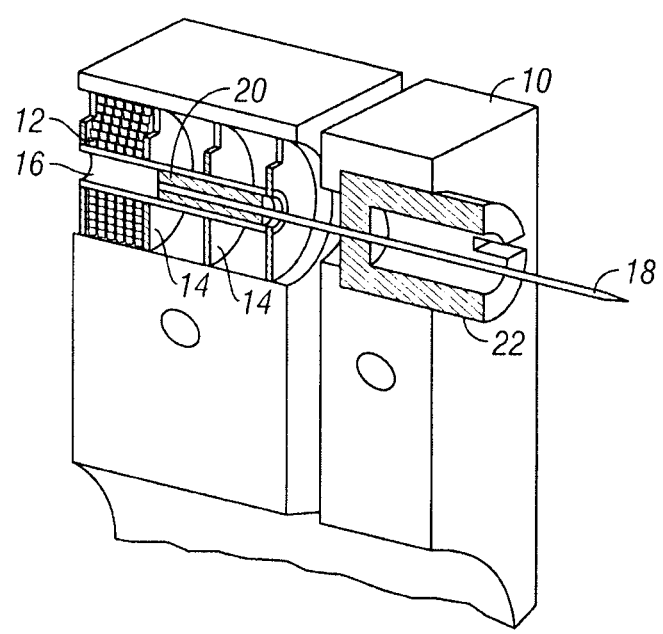
FIG. 1 illustrates an embodiment of a controllable force driver in the form of a cylindrical electric penetrating member driver using a coiled solenoid-type configuration.

The present invention may be used with a variety of different penetrating member drivers. It is contemplated that these penetrating member drivers may be spring based, solenoid based, magnetic driver based, nanomuscle based, or based on any other mechanism useful in moving a penetrating member along a path into tissue. It should be noted that the present invention is not limited by the type of driver used with the penetrating member feed mechanism. One suitable penetrating member driver for use with the present invention is shown in FIG. 1. This is an embodiment of a solenoid type electromagnetic driver that is capable of driving an iron core or slug mounted to the penetrating member assembly using a direct current (DC) power supply. The electromagnetic driver includes a driver coil pack that is divided into three separate coils along the path of the penetrating member, two end coils and a middle coil. Direct current is alternated to the coils to advance and retract the penetrating member. Although the driver coil pack is shown with three coils, any suitable number of coils may be used, for example, 4, 5, 6, 7 or more coils may be used.

Referring to the embodiment of FIG. 1, the stationary iron housing 10 may contain the driver coil pack with a first coil 12 flanked by iron spacers 14 which concentrate the magnetic flux at the inner diameter creating magnetic poles. The inner insulating housing 16 isolates the penetrating member 18 and iron core 20 from the coils and provides a smooth, low friction guide surface. The penetrating member guide 22 further centers the penetrating member 18 and iron core 20. The penetrating member 18 is protracted and retracted by alternating the current between the first coil 12, the middle coil, and the third coil to attract the iron core 20. Reversing the coil sequence and attracting the core and penetrating member 18 back into the housing retracts the penetrating member 18. The penetrating member guide 22 also serves as a stop for the iron core 20 mounted to the penetrating member 18.

Figure 2A:
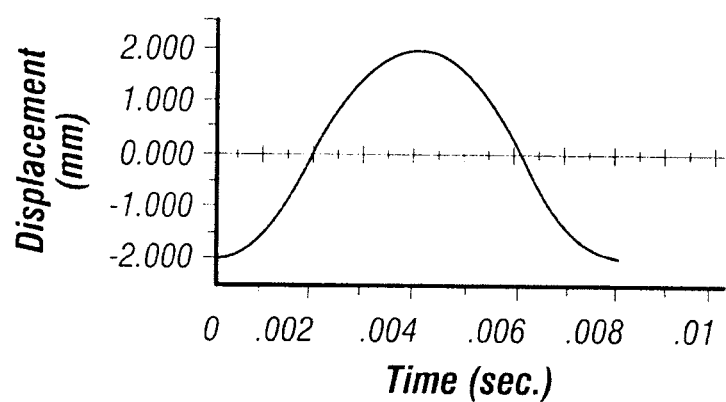
FIG. 2A illustrates a displacement over time profile of a penetrating member driven by a harmonic spring/mass system.
Figure 2B:
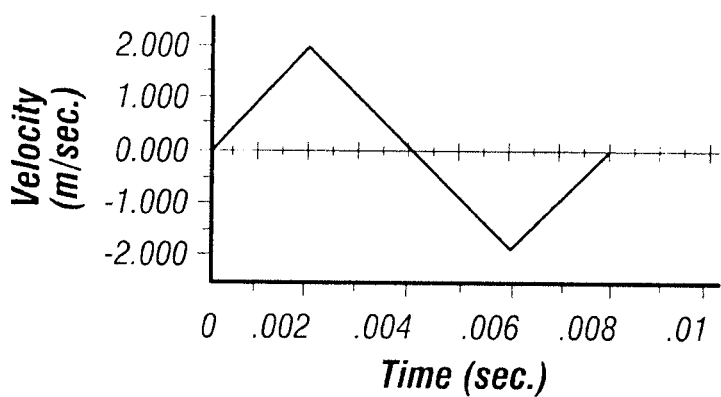
FIG. 2C illustrates a displacement over time profile of an embodiment of a controllable force driver.
Figure 2C:
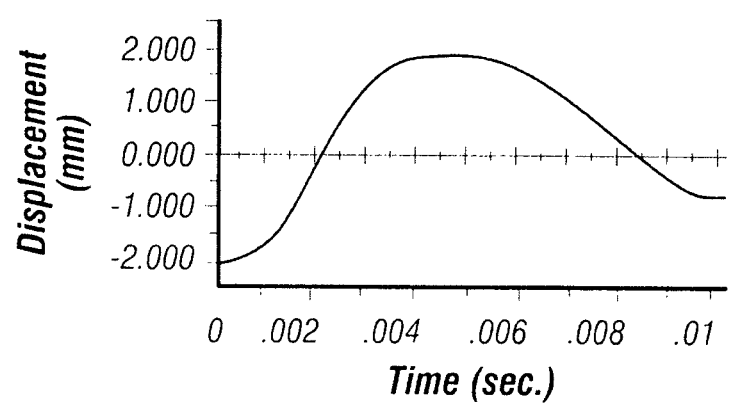
Figure 2D:
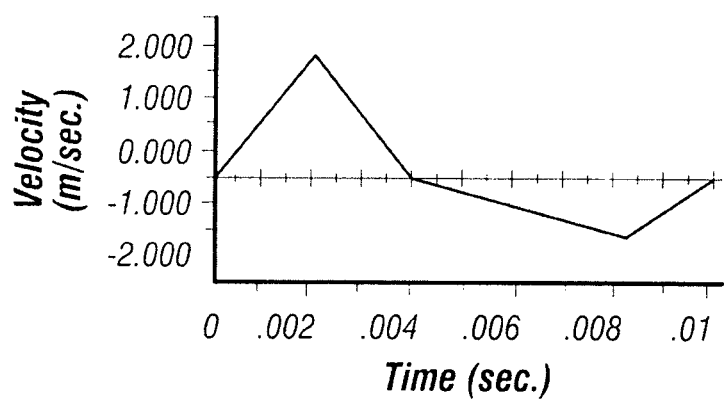
Figure 3:
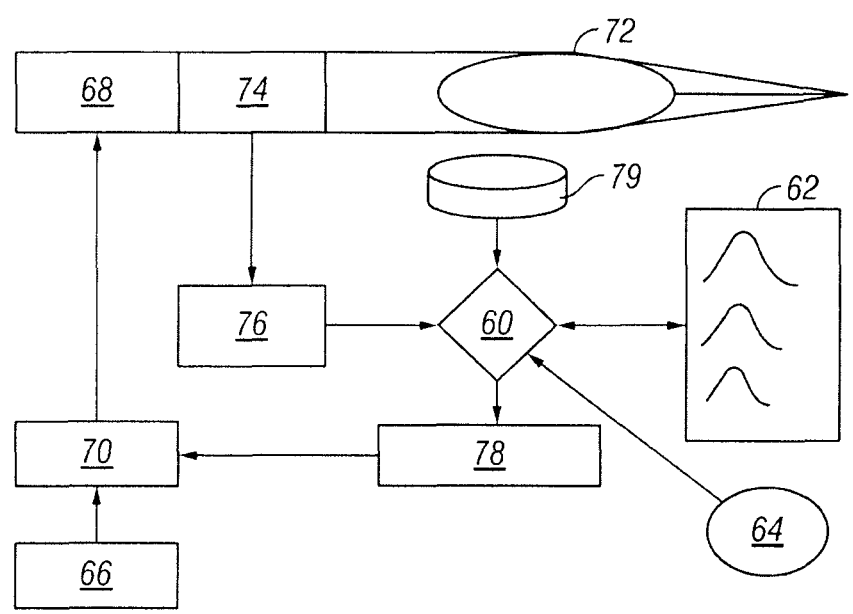
FIG. 3 is a diagrammatic view illustrating a controlled feed-back loop.

As discussed above, tissue penetration devices which employ spring or cam driving methods have a symmetrical or nearly symmetrical actuation displacement and velocity profiles on the advancement and retraction of the penetrating member 18 as shown in FIGS. 2 and 3. In most of the available lancet devices, once the launch is initiated, the stored energy determines the velocity profile until the energy is dissipated. Controlling impact, retraction velocity, and dwell time of the penetrating member 18 within the tissue can be useful in order to achieve a high success rate while accommodating variations in skin properties and minimize pain. Advantages can be achieved by taking into account of the fact that tissue dwell time is related to the amount of skin deformation as the penetrating member 18 tries to puncture the surface of the skin and variance in skin deformation from patient to patient based on skin hydration.

In this embodiment, the ability to control velocity and depth of penetration may be achieved by use of a controllable force driver where feedback is an integral part of driver control. Such drivers can control either metal or polymeric penetrating members 18 or any other type of tissue penetration element. The dynamic control of such a driver is illustrated in FIG. 2C which illustrates an embodiment of a controlled displacement profile and FIG. 20 which illustrates an embodiment of a the controlled velocity profile. These are compared to FIGS. 2A and 28, which illustrate embodiments of displacement and velocity profiles, respectively, of a harmonic spring/mass powered driver. Reduced pain can be achieved by using impact velocities of greater than about 2 m/sentry of a tissue penetrating element, such as a lancet, into tissue. Other suitable embodiments of the penetrating member driver 68 are described in commonly assigned, copending U.S. patent application Ser. No. 10/127,395, filed Apr. 19, 2002 and previously incorporated herein.

FIG. 3 illustrates the operation of a feedback loop using a processor 60. The processor 60 stores profiles 62 in non-volatile memory. A user inputs information 64 about the desired circumstances or parameters for a lancing event. The processor 60 selects a driver profile 62 from a set of alternative driver profiles that have been preprogrammed in the processor 60 based on typical or desired tissue penetration device performance determined through testing at the factory or as programmed in by the operator. The processor 60 may customize by either scaling or modifying the profile based on additional user input information 64. Once the processor has chosen and customized the profile, the processor 60 is ready to modulate the power from the power supply 66 to the penetrating member driver 68 through an amplifier 70. The processor 60 may measure the location of the penetrating member 72 using a position sensing mechanism 74 through an analog to digital converter 76 linear encoder or other such transducer. Examples of position sensing mechanisms have been described in the embodiments above and may be found in the specification for U.S. patent application Ser. No. 10/127,395, filed Apr. 19, 2002 and previously incorporated herein. The processor 60 calculates the movement of the penetrating member 72 by comparing the actual profile of the penetrating member 72 to the predetermined profile. The processor 60 modulates the power to the penetrating member driver 68 through a signal generator 78, which may control the amplifier 70 so that the actual velocity profile of the penetrating member 72 does not exceed the predetermined profile by more than a preset error limit. The error limit is the accuracy in the control of the penetrating member 72.

After the lancing event, the processor 60 can allow the user to rank the results of the lancing event. The processor 60 stores these results and constructs a database 80 for the individual user. Using the database 79, the processor 60 calculates the profile traits such as degree of painlessness, success rate, and blood volume for various profiles 62 depending on user input information 64 to optimize the profile to the individual user for subsequent lancing cycles. These profile traits depend on the characteristic phases of penetrating member advancement and retraction. The processor 60 uses these calculations to optimize profiles 62 for each user. In addition to user input information 64, an internal clock allows storage in the database 79 of information such as the time of day to generate a time stamp for the lancing event and the time between lancing events to anticipate the user's diurnal needs. The database stores information and statistics for each user and each profile that particular user uses.

In addition to varying the profiles, the processor 60 can be used to calculate the appropriate penetrating member 72 diameter and geometry suitable to realize the blood volume required by the user. For example, if the user requires about 1-5 microliter volume of blood, the processor 60 may select a 200 micron diameter penetrating member 72 to achieve these results. For each class of lancet, both diameter and lancet tip geometry, is stored in the processor 60 to correspond with upper and lower limits of attainable blood volume based on the predetermined displacement and velocity profiles.

The lancing device is capable of prompting the user for information at the beginning and the end of the lancing event to more adequately suit the user. The goal is to either change to a different profile or modify an existing profile. Once the profile is set, the force driving the penetrating member 72 is varied during advancement and retraction to follow the profile. The method of lancing using the lancing device comprises selecting a profile, lancing according to the selected profile, determining lancing profile traits for each characteristic phase of the lancing cycle, and optimizing profile traits for subsequent lancing events.

Figure 4:
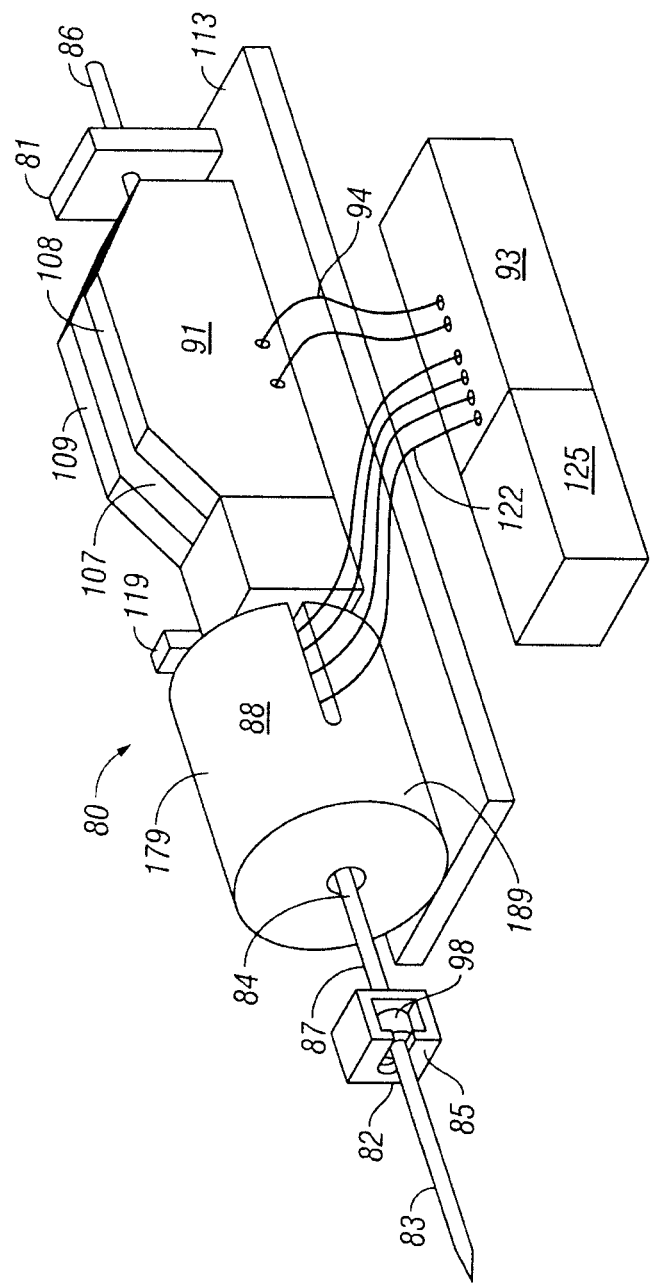
FIG. 4 is a perspective view of a tissue penetration device having features of the invention.

FIG. 4 illustrates an embodiment of a tissue penetration device, more specifically, a lancing device 80 that includes a controllable driver 179 coupled to a tissue penetration element. The lancing device 80 has a proximal end 81 and a distal end 82. At the distal end 82 is the tissue penetration element in the form of a penetrating member 83, which is coupled to an elongate coupler shaft 84 by a drive coupler 85. The elongate coupler shaft 84 has a proximal end 86 and a distal end 87. A driver coil pack 88 is disposed about the elongate coupler shaft 84 proximal of the penetrating member 83. A position sensor 91 is disposed about a proximal portion 92 of the elongate coupler shaft 84 and an electrical conductor 94 electrically couples a processor 93 to the position sensor 91. The elongate coupler shaft 84 driven by the driver coil pack 88 controlled by the position sensor 91 and processor 93 form the controllable driver, specifically, a controllable electromagnetic driver.

Figure 5:
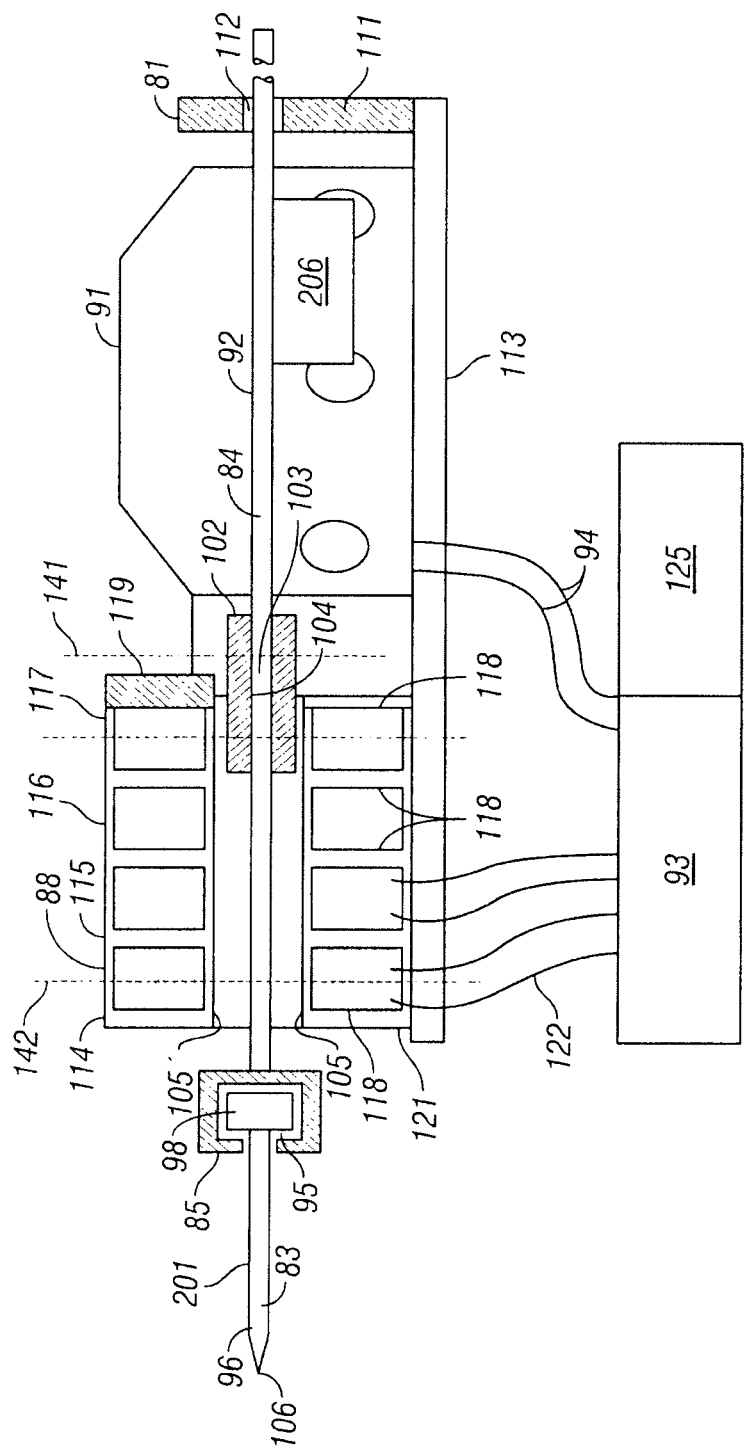
FIG. 5 is an elevation view in partial longitudinal section of the tissue penetration device of FIG. 4.

Referring to FIG. 5, the lancing device 80 can be seen in more detail, in partial longitudinal section. The penetrating member 83 has a proximal end 95 and a distal end 96 with a sharpened point at the distal end 96 of the penetrating member 83 and a drive head 98 disposed at the proximal end 95 of the penetrating member 83. A penetrating member shaft 201 is disposed between the drive head 98 and the sharpened point 97. The penetrating member shaft 201 may be comprised of stainless steel, or any other suitable material or alloy and have a transverse dimension of about 0.1 to about 0.4 mm. The penetrating member shaft 201 may have a length of about 3 mm to about 50 mm, specifically, about 15 mm to about 20 mm. The drive head 98 of the penetrating member 83 is an enlarged portion having a transverse dimension greater than a transverse dimension of the penetrating member shaft 201 distal of the drive head 98. This configuration allows the drive head 98 to be mechanically captured by the drive coupler 85. The drive head 98 may have a transverse dimension of about 0.5 to about 2 mm.

A magnetic member 102 is secured to the elongate coupler shaft 84 proximal of the drive coupler 85 on a distal portion 203 of the elongate coupler shaft 84. The magnetic member 102 is a substantially cylindrical piece of magnetic material having an axial lumen 204 extending the length of the magnetic member 102. The magnetic member 102 has an outer transverse dimension that allows the magnetic member 102 to slide easily within an axial lumen 105 of a low friction, possibly lubricious, polymer guide tube 105' disposed within the driver coil pack 88. The magnetic member 102 may have an outer transverse dimension of about 1.0 to about 5.0 mm, specifically, about 2.3 to about 2.5 mm. The magnetic member 102 may have a length of about 3.0 to about 5.0 mm, specifically, about 4.7 to about 4.9 mm. The magnetic member 102 can be made from a variety of magnetic materials including ferrous metals such as ferrous steel, iron, ferrite, or the like. The magnetic member 102 may be secured to the distal portion 203 of the elongate coupler shaft 84 by a variety of methods including adhesive or epoxy bonding, welding, crimping or any other suitable method.

Proximal of the magnetic member 102, an optical encoder flag 206 is secured to the elongate coupler shaft 84. The optical encoder flag 206 is configured to move within a slot 107 in the position sensor 91. The slot 107 of the position sensor 91 is formed between a first body portion 108 and a second body portion 109 of the position sensor 91. The slot 107 may have separation width of about 1.5 to about 2.0 mm. The optical encoder flag 206 can have a length of about 14 to about 18 mm, a width of about 3 to about 5 mm and a thickness of about 0.04 to about 0.06 mm.

The optical encoder flag 206 interacts with various optical beams generated by LEOs disposed on or in the position sensor body portions 108 and 109 in a predetermined manner. The interaction of the optical beams generated by the LEOs of the position sensor 91 generates a signal that indicates the longitudinal position of the optical flag 206 relative to the position sensor 91 with a substantially high degree of resolution. The resolution of the position sensor 91 may be about 200 to about 400 cycles per inch, specifically, about 350 to about 370 cycles per inch. The position sensor 91 may have a speed response time (position/time resolution) of 0 to about 120,000 Hz, where one dark and light stripe of the flag constitutes one Hertz, or cycle per second. The position of the optical encoder flag 206 relative to the magnetic member 102, driver coil pack 88 and position sensor 91 is such that the optical encoder 91 can provide precise positional information about the penetrating member 83 over the entire length of the penetrating member's power stroke.

An optical encoder that is suitable for the position sensor 91 is a linear optical incremental encoder, model HEOS 9200, manufactured by Agilent Technologies. The model HEOS 9200 may have a length of about 20 to about 30 mm, a width of about 8 to about 12 mm, and a height of about 9 to about 11 mm. Although the position sensor 91 illustrated is a linear optical incremental encoder, other suitable position sensor embodiments could be used, provided they posses the requisite positional resolution and time response. The HEDS 9200 is a two channel device where the channels are 90 degrees out of phase with each other. This results in a resolution of four times the basic cycle of the flag. These quadrature outputs make it possible for the processor to determine the direction of penetrating member 83 travel. Other suitable position sensors include capacitive encoders, analog reflective sensors, such as the reflective position sensor discussed above, and the like.

A coupler shaft guide 111 is disposed towards the proximal end 81 of the lancing device 80. The guide 111 has a guide lumen 112 disposed in the guide 111 to slidingly accept the proximal portion 92 of the elongate coupler shaft 84. The guide 111 keeps the elongate coupler shaft 84 centered horizontally and vertically in the slot 102 of the optical encoder 91.

Figure 6:
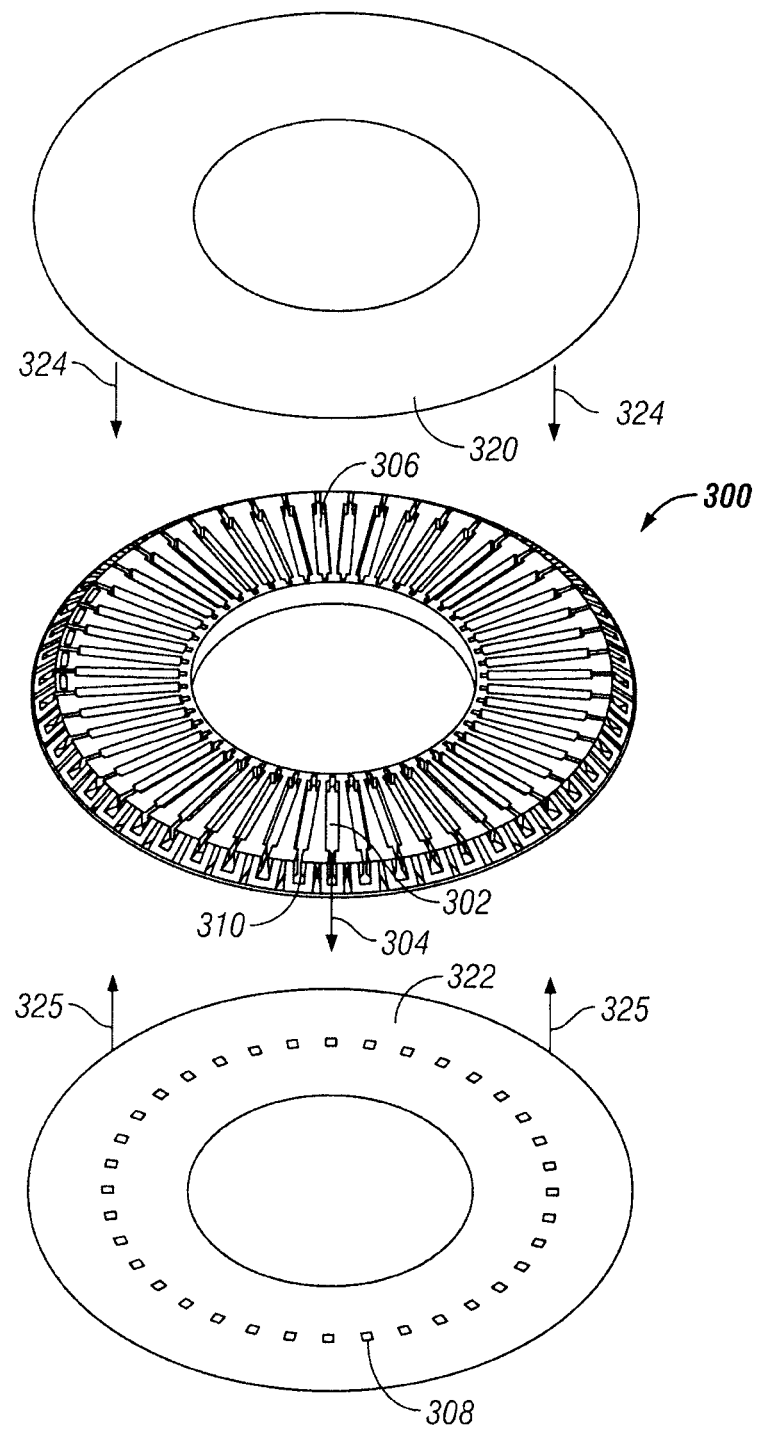
FIG. 6 shows an exploded perspective view of one embodiment of a device according to the present invention.

Referring now to FIG. 6, a still further embodiment of a disposable according to the present invention will be described. FIG. 6 shows one embodiment of a disposable 300 which may be removably inserted into an apparatus for driving penetrating members 302 to pierce skin or tissue. The disposable 300 has a plurality of penetrating members 302 that may be individually or otherwise selectively actuated so that the penetrating members 302 may extend outward from the disposable, as indicated by arrow 304, to penetrate tissue. In the present embodiment, the disposable 300 may be based on a flat disc with a number of penetrating members 302 such as, but in no way limited to, (25, 50, 75, 100, . . . ) arranged radially on the disc or disposable 800. It should be understood that although the disposable 300 is shown as a disc or a disc-shaped housing, other shapes or configurations of the disposable 300 may also work without departing from the spirit of the present invention of placing a plurality of penetrating members 302 to be engaged, singly or in some combination, by a penetrating member driver.

Each penetrating member 302 may be contained in a cavity 306 in the disposable 300 with the penetrating member's sharpened end facing radially outward and may be in the same plane as that of the disposable. The cavity 306 may be molded, pressed, forged, or otherwise formed in the disposable. Although not limited in this manner, the ends of the cavities 306 may be divided into individual fingers (such as one for each cavity) on the outer periphery of the disc. The particular shape of each cavity 306 may be designed to suit the size or shape of the penetrating member 302 therein or the amount of space desired for placement of the analyte detecting members 808. For example and not limitation, the cavity 306 may have a V-shaped cross-section, a U-shaped cross-section, C-shaped cross-section, a multi-level cross section or the other cross-sections. The opening 810 through which a penetrating member 302 may exit to penetrate tissue may also have a variety of shapes, such as but not limited to, a circular opening, a square or rectangular opening, a U-shaped opening, a narrow opening that only allows the penetrating member 302 to pass, an opening with more clearance on the sides, a slit, a configuration as shown in FIG. 75, or the other shapes.

In this embodiment, after actuation, the penetrating member 302 is returned into the disposable and may be held within the disposable 300 in a manner so that it is not able to be used again. By way of example and not limitation, a used penetrating member 302 may be returned into the disposable and held by the launcher in position until the next lancing event. At the time of the next lancing, the launcher may disengage the used penetrating member 302 with the disposable 300 turned or indexed to the next clean penetrating member 302 such that the cavity holding the used penetrating member 302 is position so that it is not accessible to the user (i.e. turn away from a penetrating member exit opening). In some embodiments, the tip of a used penetrating member 302 may be driven into a protective stop that hold the penetrating member 302 in place after use. The disposable 300 is replaceable with a new disposable 300 once all the penetrating members 302 have been used or at such other time or condition as deemed desirable by the user.

Referring still to the embodiment in FIG. 6, the disposable 300 may provide sterile environments for penetrating members 302 via seals, foils, covers, polymeric, or similar materials used to seal the cavities and provide enclosed areas for the penetrating members 302 to rest in. In the present embodiment, a sterility barrier or seal layer 320 is applied to one surface of the disposable 300. The seal layer 320 may be made of a variety of materials such as a metallic foil or other seal materials and may be of a tensile strength and other quality that may provide a sealed, sterile environment until the seal layer 320 is penetrate by a suitable or penetrating device providing a preselected or selected amount of force to open the sealed, sterile environment. Each cavity 306 may be individually sealed with a layer 320 in a manner such that the opening of one cavity does not interfere with the sterility in an adjacent or other cavity in the disposable 800. As seen in the embodiment of FIG. 6, the seal layer 320 may be a planar material that is adhered to a top surface of the disposable 800.

Depending on the orientation of the disposable 300 in the penetrating member driver apparatus, the seal layer 320 may be on the top surface, side surface, bottom surface, or other positioned surface. For ease of illustration and discussion of the embodiment of FIG. 6, the layer 320 is placed on a top surface of the disposable 800. The cavities 306 holding the penetrating members 302 are sealed on by the sterility barrier layer 320 and thus create the sterile environments for the penetrating members 302. The sterility barrier layer 320 may seal a plurality of cavities 306 or only a select number of cavities as desired.

In a still further feature of FIG. 6, the disposable 300 may optionally include a plurality of analyte detecting members 308 on a substrate 822 which may be attached to a bottom surface of the disposable 300. The substrate may be made of a material such as, but not limited to, a polymer, a foil, or other material suitable for attaching to a disposable and holding the analyte detecting members 308. As seen in FIG. 6, the substrate 322 may hold a plurality of analyte detecting members, such as but not limited to, about 10-50, 50-100, or other combinations of analyte detecting members. This facilitates the assembly and integration of analyte detecting members 308 with disposable 300. These analyte detecting members 308 may enable an integrated body fluid sampling system where the penetrating members 302 create a wound tract in a target tissue, which expresses body fluid that flows into the disposable 300 for analyte detection by at least one of the analyte detecting members 308. The substrate 322 may contain any number of analyte detecting members 308 suitable for detecting analytes in disposable having a plurality of cavities 306. In one embodiment, many analyte detecting members 308 may be printed onto a single substrate 322 which is then adhered to the disposable to facilitate manufacturing and simplify assembly. The analyte detecting members 308 may be electrochemical in nature. The analyte detecting members 308 may further contain enzymes, dyes, or other detectors which react when exposed to the desired analyte. Additionally, the analyte detecting members 308 may comprise of clear optical windows that allow light to pass into the body fluid for analyte analysis. The number, location, and type of analyte detecting member 308 may be varied as desired, based in part on the design of the disposable, number of analytes to be measured, the need for analyte detecting member calibration, and the sensitivity of the analyte detecting members. If the disposable 300 uses an analyte detecting member arrangement where the analyte detecting members are on a substrate attached to the bottom of the disposable, there may be through holes (as shown in FIG. 76), wicking elements, capillary tube or other devices on the disposable 300 to allow body fluid to flow from the disposable to the analyte detecting members 308 for analysis. In other configurations, the analyte detecting members 308 may be printed, formed, or otherwise located directly in the cavities housing the penetrating members 302 or areas on the disposable surface that receive blood after lancing.

The use of the seal layer 320 and substrate or analyte detecting member layer 822 may facilitate the manufacture of the disposable 300. For example, a single seal layer 320 may be adhered, attached, or otherwise coupled to the disposable 300 as indicated by arrows 324 to seal many of the cavities 306 at one time. A sheet 322 of analyte detecting members may also be adhered, attached, or otherwise coupled to the disposable 300 as indicated by arrows 325 to provide many analyte detecting members on the disposable at one time. During manufacturing of one embodiment of the present invention, the disposable 300 may be loaded with penetrating members 302, sealed with layer 320 and a temporary layer (not shown) on the bottom where substrate 322 would later go, to provide a sealed environment for the penetrating members 302. This assembly with the temporary bottom layer is then taken to be sterilized. After sterilization, the assembly is taken to a clean room (or it may already be in a clear room or equivalent environment) where the temporary bottom layer is removed and the substrate 322 with analyte detecting members is coupled to the disposable as shown in FIG. 6. This process allows for the sterile assembly of the disposable with the penetrating members 302 using processes and/or temperatures that may degrade the accuracy or functionality of the analyte detecting members on substrate 322. As a nonlimiting example, the entire disposable 300 may then be placed in a further sealed container such as a pouch, bag, plastic molded container, etc. . . . to facilitate contact, improve ruggedness, and/or allow for easier handling.

In some embodiments, more than one seal layer 320 may be used to seal the cavities 306. As examples of some embodiments, multiple layers may be placed over each cavity 306, half or some selected portion of the cavities may be sealed with one layer with the other half or selected portion of the cavities sealed with another sheet or layer, different shaped cavities may use different seal layer, or the like. The seal layer 320 may have different physical properties, such as those covering the penetrating members 302 near the end of the disposable may have a different color such as red to indicate to the user (if visually inspectable) that the user is down to say 10, 5, or other number of penetrating members 302 before the disposable should be changed out.

Figure 7:
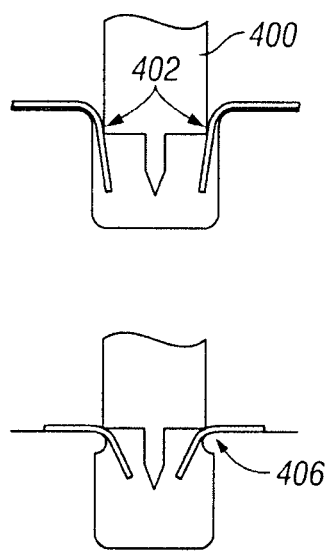
FIG. 7 shows a cross-sectional view of one embodiment of a punch according to the present invention.
Figure 8:
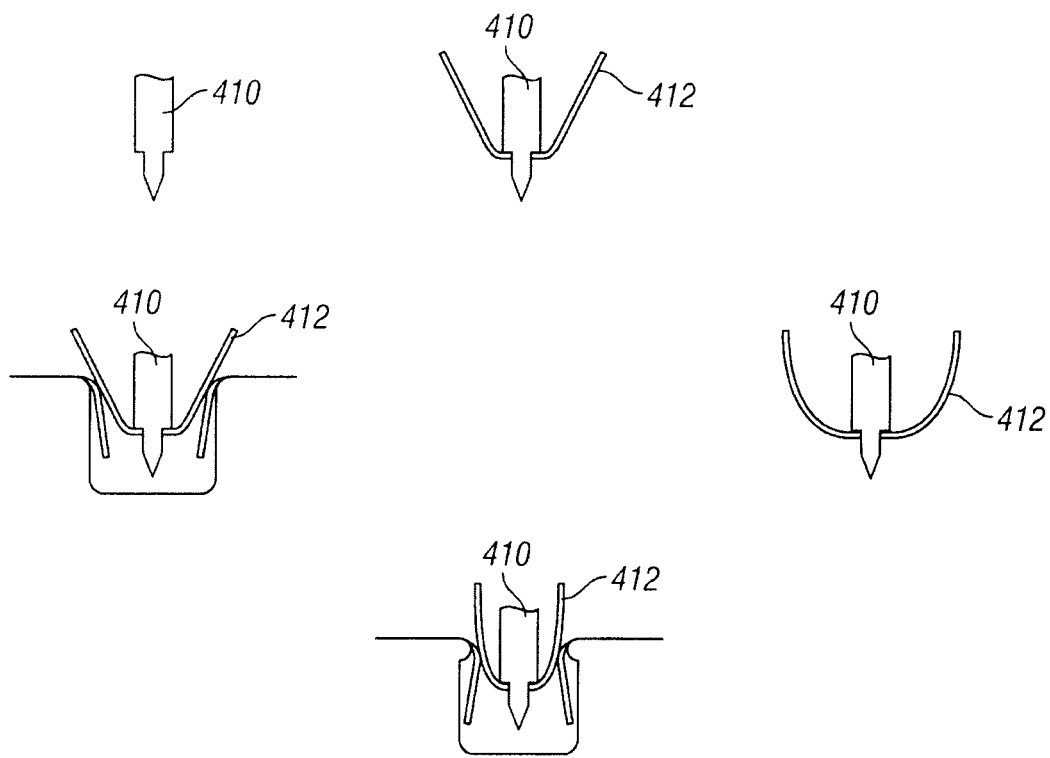
FIG. 8 shows another embodiment of a punch according to the present invention.

Referring now to FIGS. 7 and 8, various embodiments of the present invention will now be described in further detail. Improvements have been made to the punch device 400. The present invention addresses issues with the punch 400 moving the cut sterility barrier seal 320 to the sides of the chamber, so that the sterility barrier seal 320 springs back and you get some end effects where the punch 400 angles the sterility barrier seal 320 into the corner, resulting in tearing rather than a clean cut to open the sterility barrier. The gripper has to bend the sterility barrier seal 320 out of the way, as it runs along the channel and this results in the half Newton range or force required.

FIG. 7 shows an embodiment of the punch 400 with a widened portion 402 that tightly fits against the opening of the cavity. Some embodiments may also have a flash portion 406 that interferes with the punch 400 during punching. The helps push the flaps of the sterility barrier seal 320 to the side and does not interfere with the gripper during travel.

FIG. 8 shows yet another embodiment with a narrow punch 410 with winged portions 412. The wings 412 are of sufficient size and stiffness to push the sterility barrier seal 320 pieces against the side of the cavities.

Referring now to FIGS. 9 through 16, a still further embodiment of the present invention describes a shield or guide rail attached to the gripper and not the punch 400. Thus the shield is in placed while the gripper is coupled to the penetrating member 302. It does not need to be fitted to be exactly the same size as the cavity width, such as may be needed by a punch 400, thus allowing for easier manufacturability.

Figure 9:
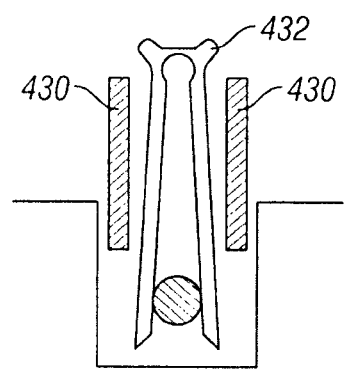
FIG. 9 shows one embodiment of a gripper with a shield.
Figure 10:
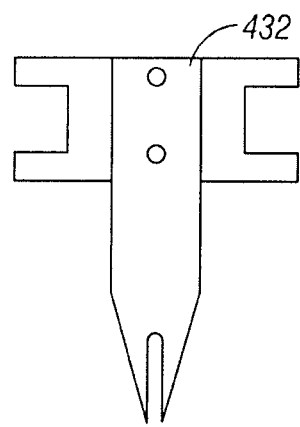
FIGS. 10-12 show other embodiments of a gripper.

Referring now to FIGS. 9 and 10, in this embodiment the shield 430 is mounted above the gripper 432. This hollow open channel rides over the gripper and is fixed to the track. It also guards from accidentally touching the gripper itself. The present invention uses the guard to bend the sterility barrier seal 320 out of the way.

Figure 11:
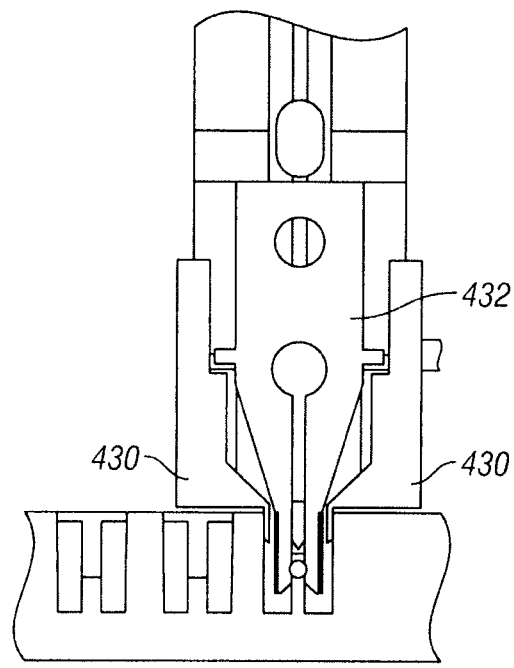
Figure 12:
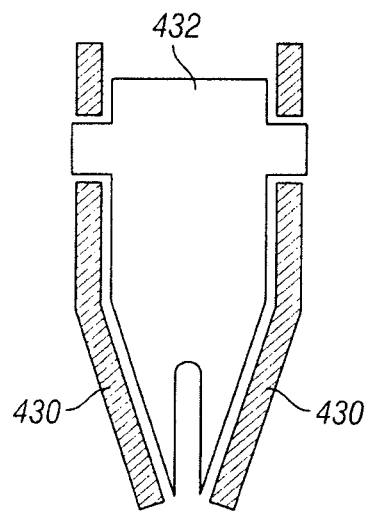
Figure 13:
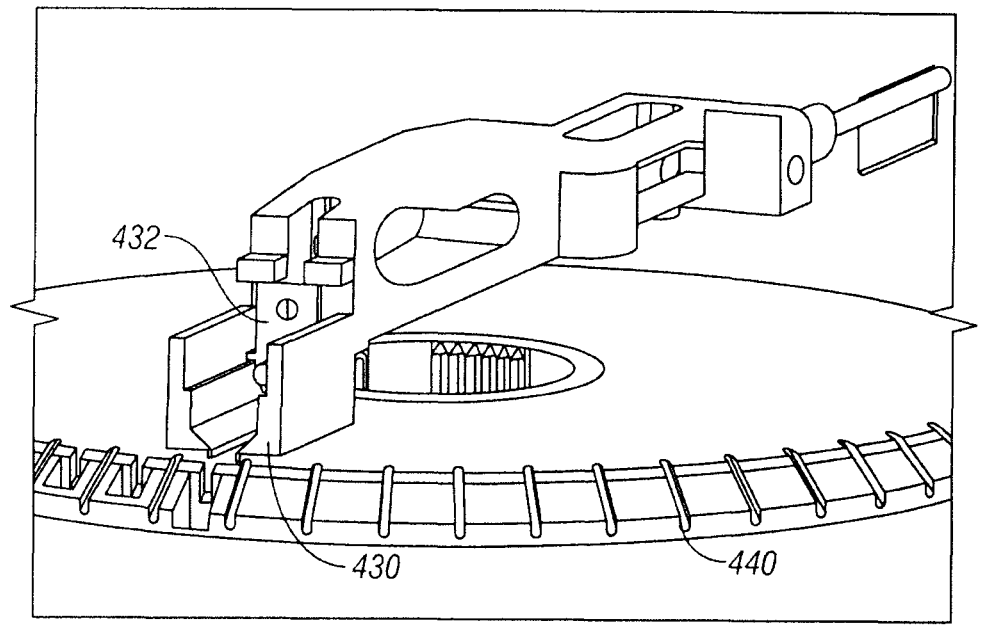
FIGS. 13-14 show embodiments of a gripper and a drive assembly.
Figure 14:
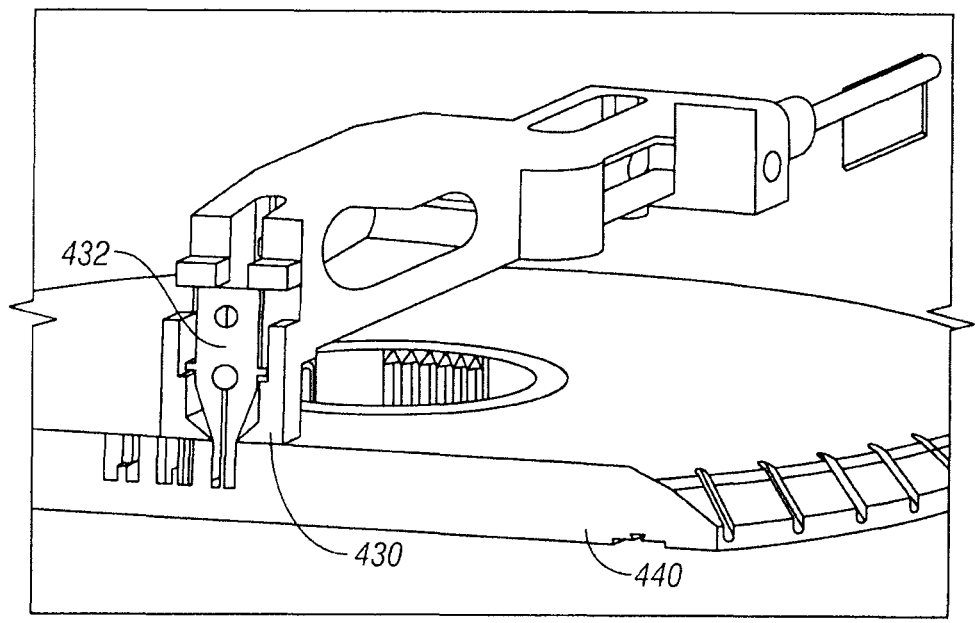

Referring now to FIG. 11, a view of the gripper 432 engaged to a penetrating member 302 and a shield 430 pushing sterility barrier seal 320 aside is shown. FIG. 12 shows yet another cross-section of the gripper 432 and shield 430. FIGS. 13 and 14 shows yet another depiction with the entire gripper and drive assembly positioned over a disposable 440 containing a plurality of penetrating members 302.

Figure 15:
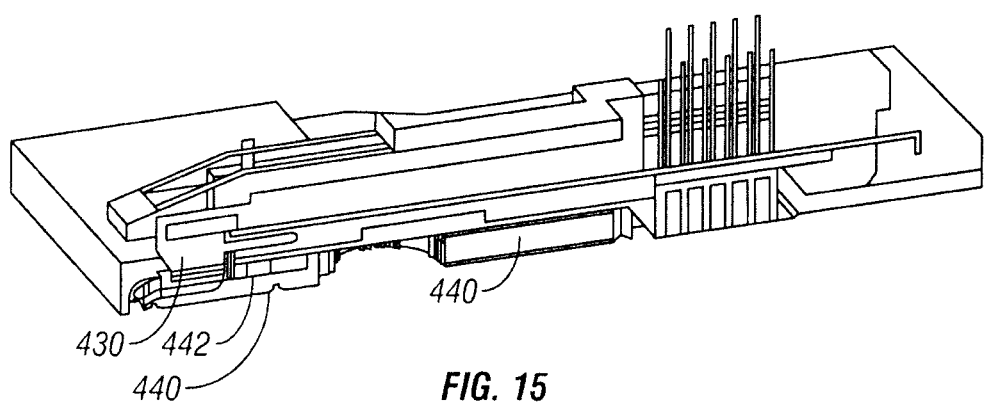
FIGS. 15-16 show a cross-section and side view of one embodiment of the gripper and the drive assembly.
Figure 16:
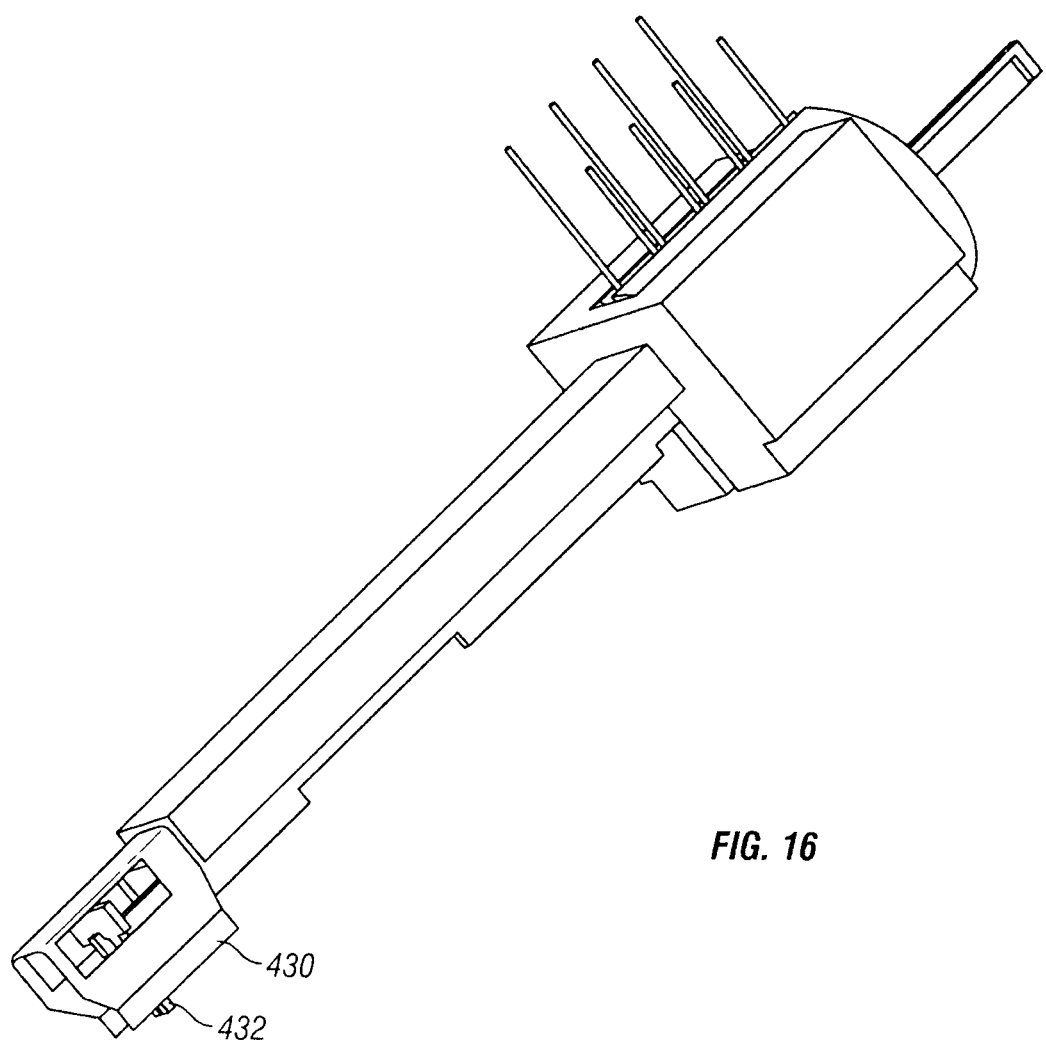

FIG. 15 shows a cross-section view with the entire gripper and drive assembly positioned over a disposable 440 containing a plurality of penetrating members 442. FIG. 16 shows a perspective view of just the gripper and drive assembly.

In yet another embodiment of the present invention, a punch 400 is provided that produces less friction and minimizes or eliminates a razor sharp blade effect. Instead, the punch 400 has a blunt blade. In this embodiment, punch 400 has an "H" blade geometry, leaving an "H" cut which the guard can fold out of the way. The blade can be angled like a guillotine with feet at either end to reduce the force needed to cut open the sterility barrier seal 320 and hence the sterility barrier seal 320 thickness can be increased. As a non-limiting example, the sterility barrier seal 320 thickness can be about 20 microns to avoid pinholes, and hence bacteria/spores In one specific embodiment, the foil on the disposable is 201-J thick aluminum with 71-J of heat seal lacquer.

In a still further embodiment, the present invention may include an improved armature design. In one embodiment, the armature is made stiffer, by increasing diameter of the rod or going to a rectangular cross section in the place that suffers the most deflection. Bearings can also be modified (in the disposable 440); currently it is a round lancet in a square bearing. The plan is to set the lancet in a "V" channel and then to provide a light downward force pressing the lancet into the "V". As the lancet wants to move due to the asymmetrical chamfer, that force will be overcome and then it can move in compliance with eh chamfer force. We apply this force to the top of the gripper using a "V" shape top on the gripper, the gripper is now stabilized so that it can't rattle around, while maintaining the compliance for the lancet to move because of the chamfer. The end result is dampening of the oscillations in the armature, thus reducing the jitter.

Space: to reduce the length of the travel of the slider due to space constraints. One solution would be to ramp quickly and ramp up only when needed, therefore it becomes a non-linear cam arrangement. This gets us reduced length. In addition, it allows us to shorten the stroke. To get height for PCB we can go from a double-sided cam to a single sided cam with a spring to provide the force in two directions.

Figure 17:
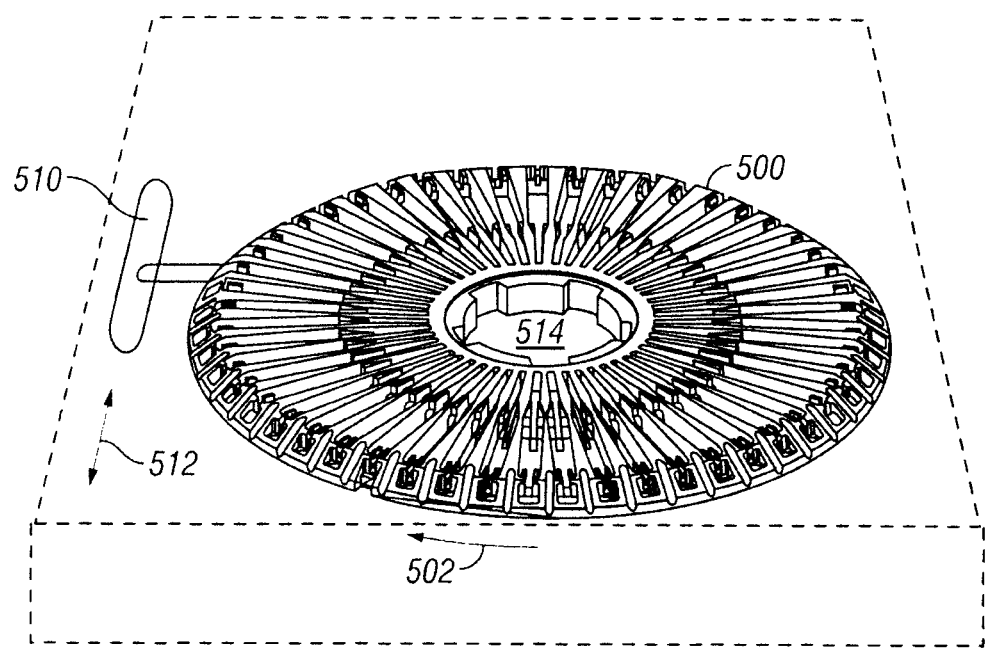
FIG. 17 shows a schematic of one embodiment of a slider used to rotate a disc.

Referring now to FIG. 17, yet another aspect of the present invention will now be described. To bring a new, unused penetrating member to use, the disposable 500 may be rotated as indicated by arrow 502. A linear slider 510 moves forward and backward as indicated by arrow 512. The forward motion of the slider 510 rotates the disposable 500, among other things. In some embodiments, backward motion may be used to rotate the disposable 500 (it all depends on where the slider starts). Rotation occurs when a keyed gear (not shown) that the opening 514 fits over is rotated by motion of the slider 510. Of course, the slider 510 in the present embodiment also actuates a plurality of other motions such as clearing the gripper, shield, and drive assembly, to lift them clear so that the disposable 500 can rotate.

Figure 18:
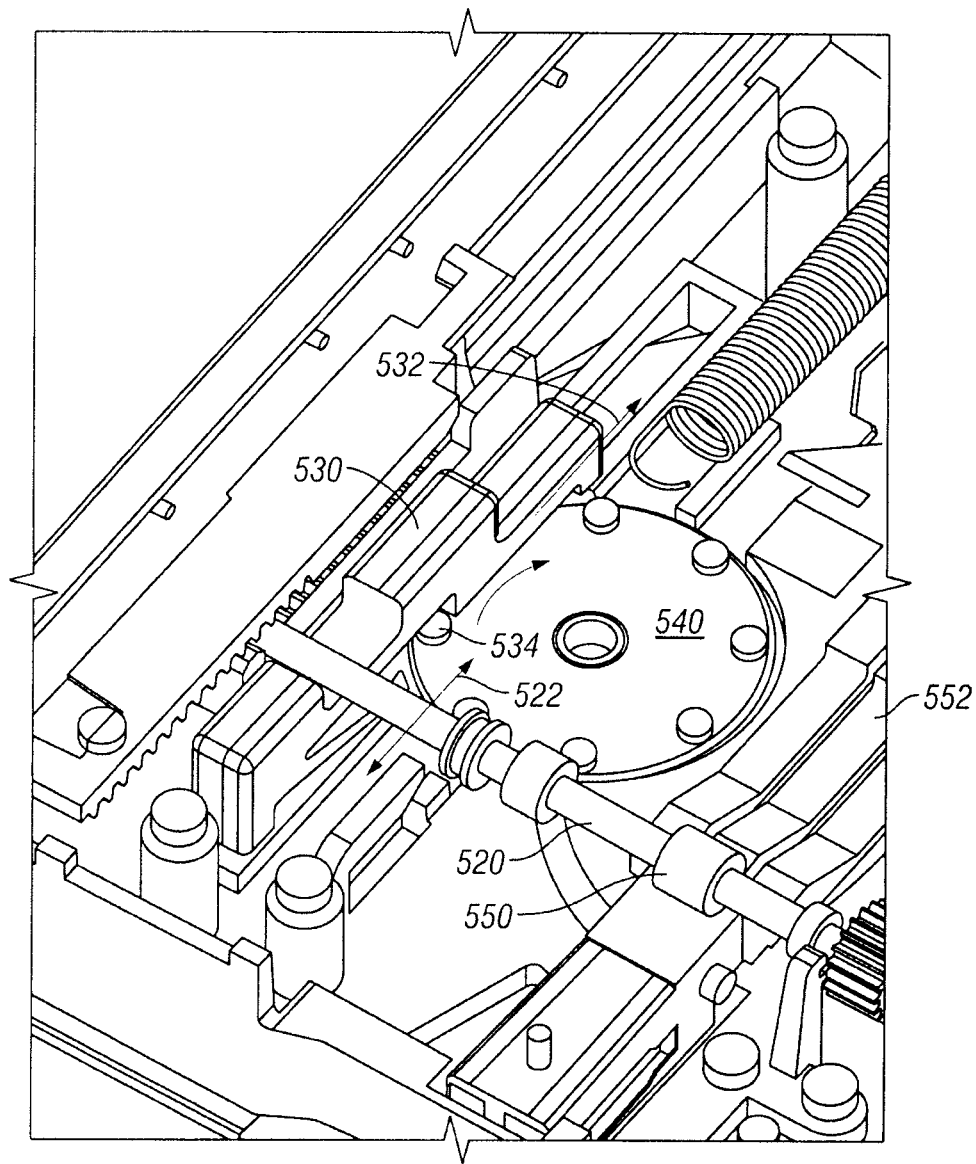

Referring now to FIG. 18 shows how movement of the slider 510 moves rod 520 as indicate by arrows 522. For ease of illustration, certain portions of the device are removed to allow easier visualization of the moving parts. The motion of rod 522 causes a second slider 530 to move as indicated by arrow 532 and engage a stub 534 on the rotating wheel 540. This wheel 540 turns the gear the fits inside the opening 514, which rotates the disposable 500. In the present embodiment, a roller 550 also travels on a cam surface 552.

Figure 19:
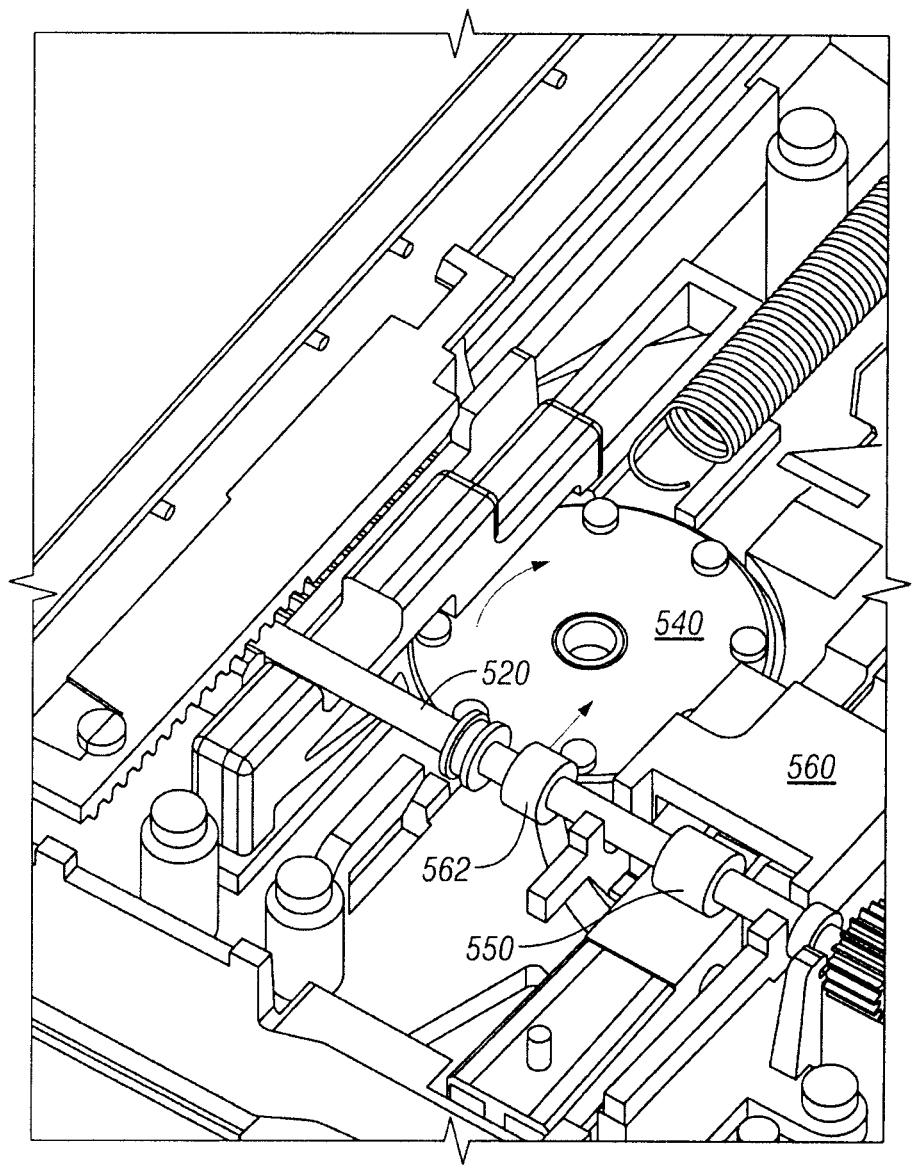
Figure 20:
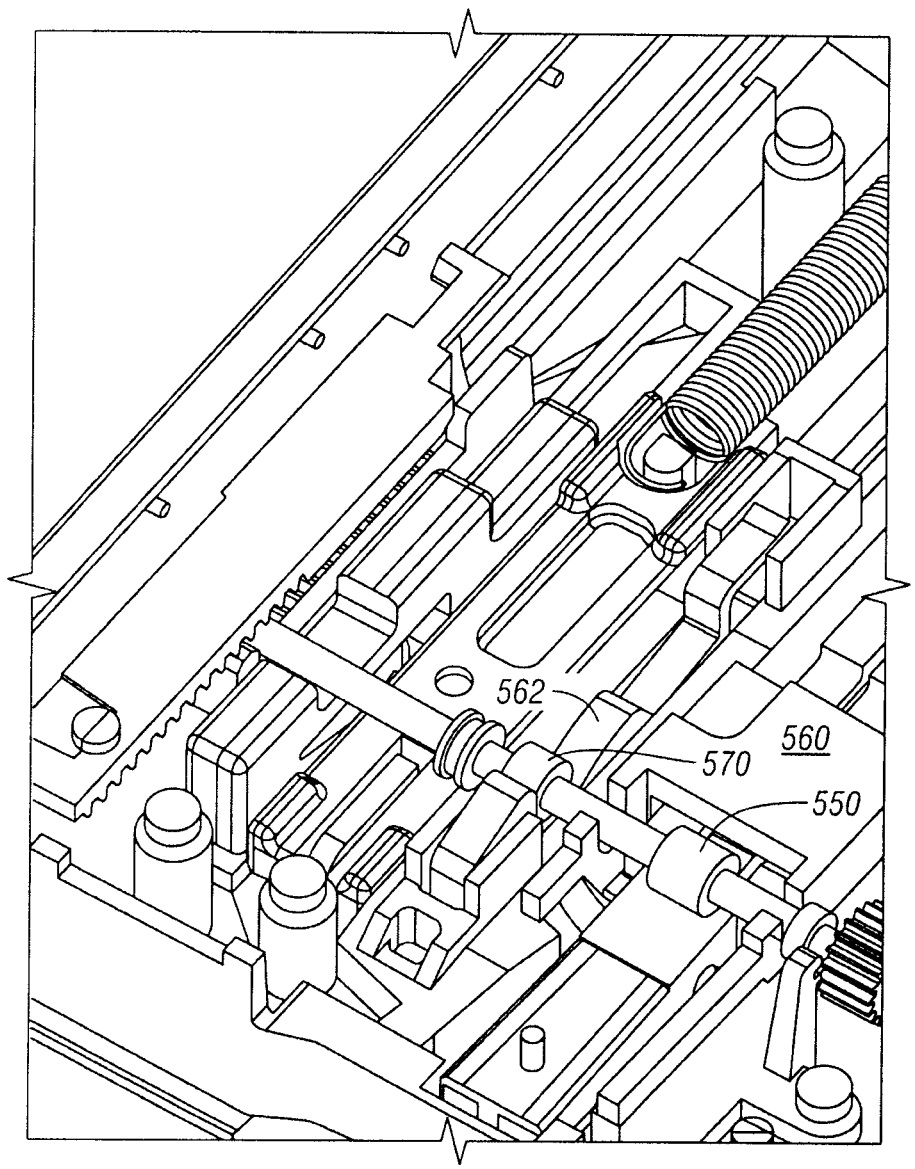
FIG. 20 illustrates a velocity over time profile of an embodiment of a controllable force driver.
Figure 21A:
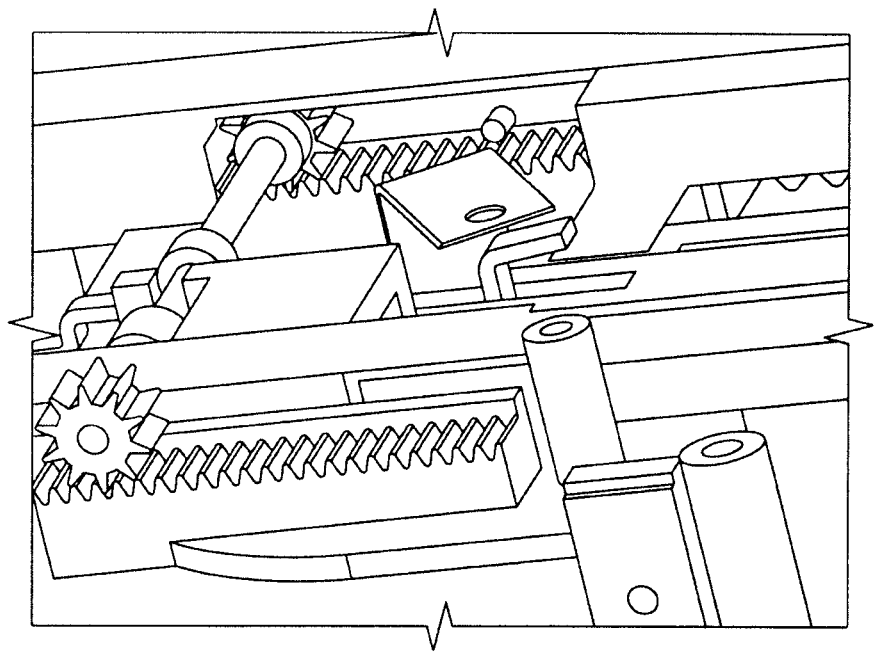
Figure 21A:
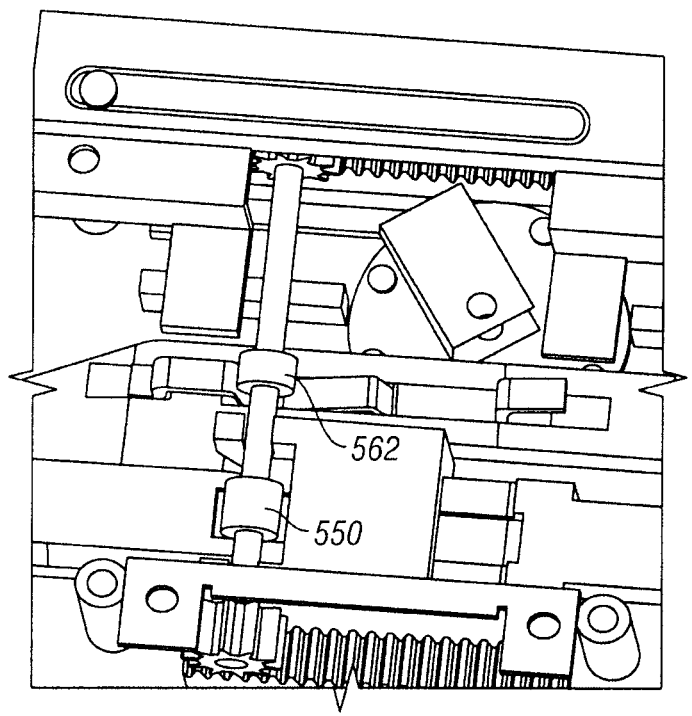
Figure 21B:
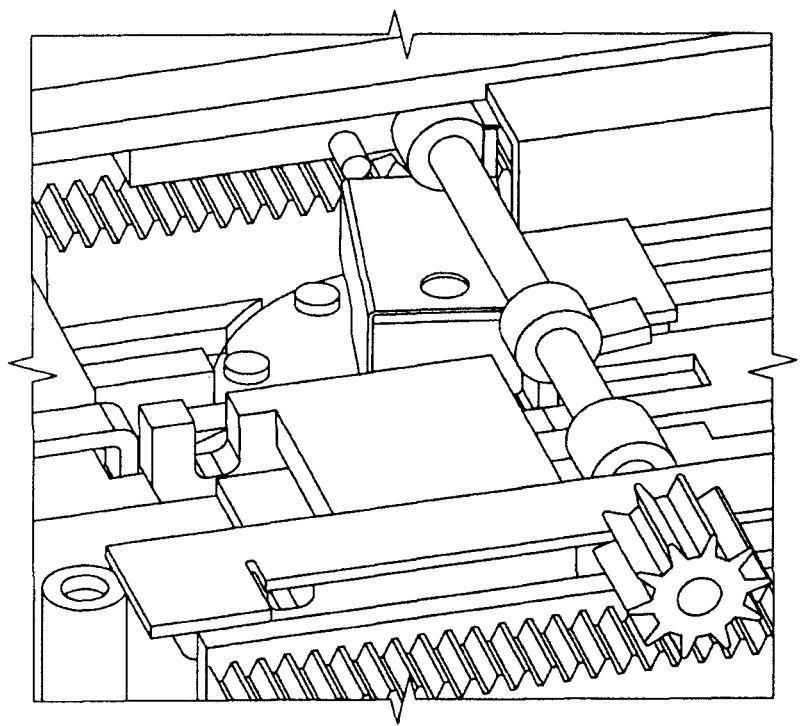
Figure 22:
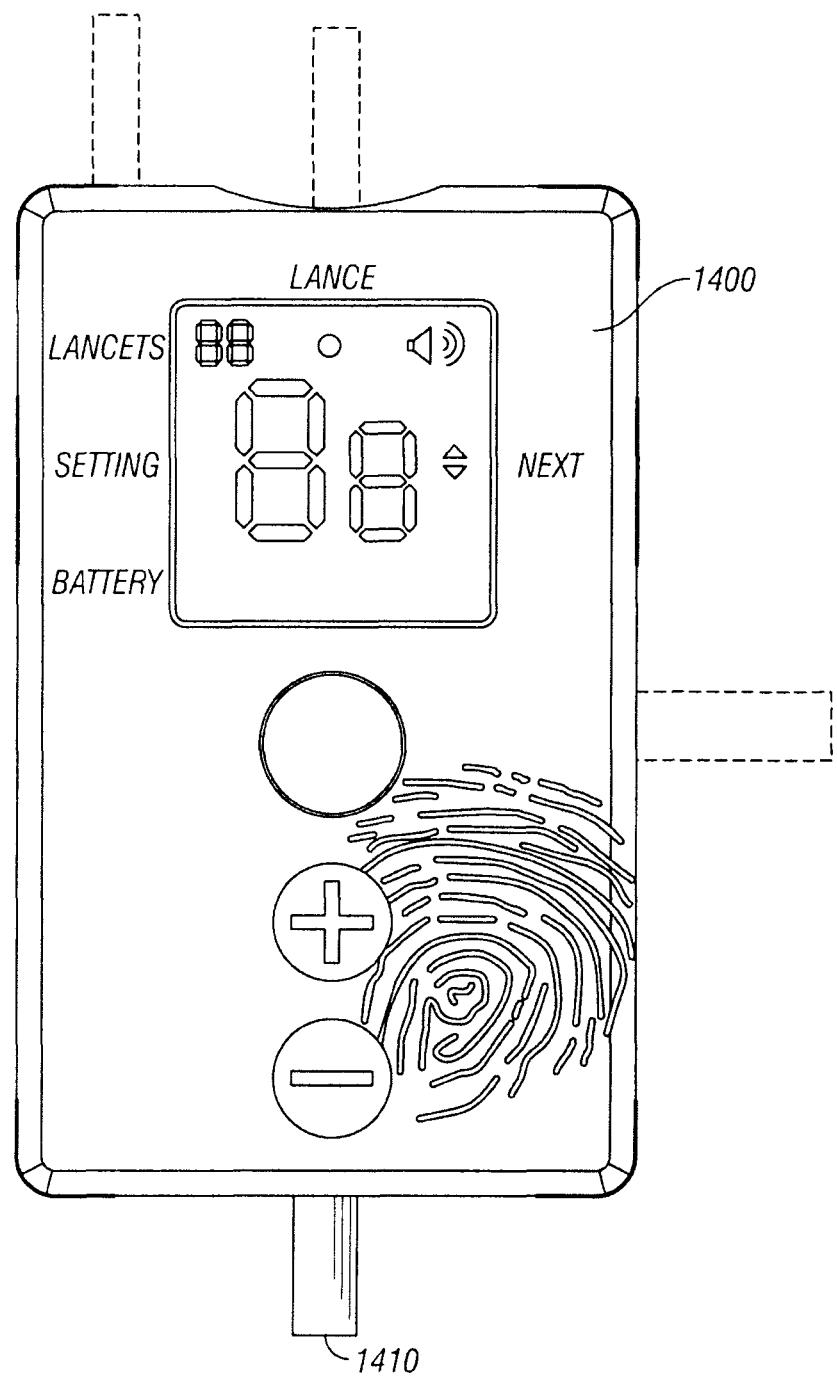
FIGS. 22-23 show embodiments of an analyte testing device for use with a test strip.

As seen in FIG. 19, the roller 550 also move a slider 560. The rod 520 also includes yet another roller 562. This roller as seen in FIG. 20, follows another cam surface 570. The cam surfaces 552 (FIG. 18) and 570 (FIG. 20) allow for raising and lowering of the punch 400, shield, gripper, drive assembly, etc. . . . to allow for the disposable 500 to rotate and a new penetrating member cavity to be opened and a member loaded for firing. In some embodiments, the various steps that need to happen are similar to those described in commonly assigned copending U.S. patent application Ser. No. 10/323,623 (38187-2607) filed Dec. 18, 2002. FIG. 21 shows still further embodiments of the present invention. It more clearly shows some of the elements such as roller 562. Embodiments using the linear motion of the slider 510 and linear motion of the rod 520 pushing linear sliders and pushing rollers to follow linear cam surfaces are very robust and will not easily fail. It should be understood that in some embodiments, a motor may be coupled to the slider to advance it instead of relying on user force.

Figure 23:
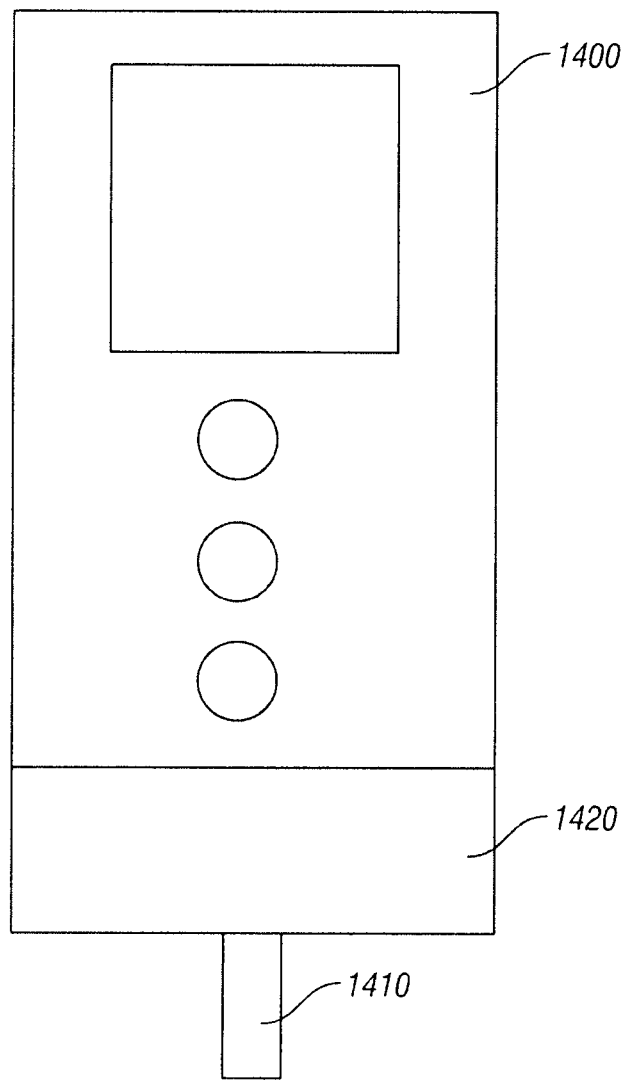

Referring now to FIG. 23, a still further embodiment is shown where an attachment 1420 may be added to an electronic lancing device. This attachment, in one embodiment, contains a plurality of test strips for dispensing. In another embodiment, it may provide the electronics used for functioning as glucose or other analyte meter.

Referring now to FIGS. 24 through 28, these embodiments of the present invention relate to Point of Care lancing, sampling, sensing, and disposable. The present invention provides a single device, suitable for use with multiple users in situations such as POC applications in adults or neonates. In one embodiment, the present invention address the issue by having a removable front end that both functions as a sample acquisition device and a sterility barrier between uses of a single device with multiple users in a professional care environment.

Figure 24:
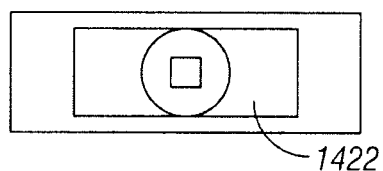
Figure 25:
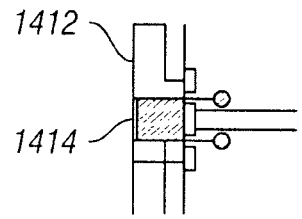

Referring now to FIGS. 24 and 25, sample capture from the surface of the finger may be carried out after the lancing step. A shield or guard may protect the front end from contamination and transfer of biohazard between successive patients. FIG. 24 shows that a portion 1422 may be hydrophobic. FIG. 25 shows that there may be hydrophobic plate 1412 and a hydrophilic mesh 1414.

Figure 26:
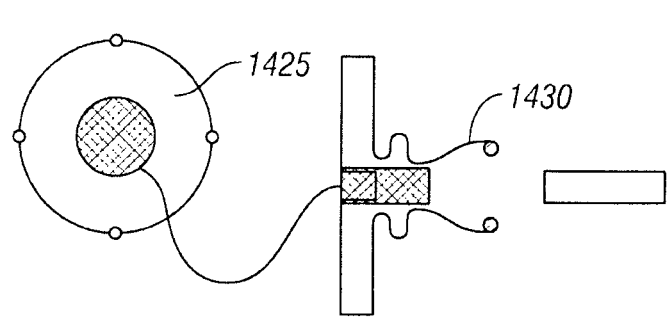
Figure 27:
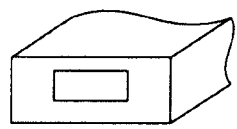
Figure 28:
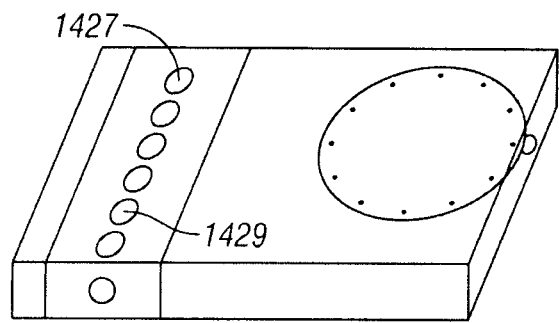
FIG. 28 illustrates the velocity over time profile of a penetrating member driver by a harmonic spring/mass system.

Referring now to FIG. 26, one embodiment of the present invention is a device 1425 that has a plastic molded part with "tentacles" 1430 designed to remove the sterility barrier seal 320 covering of the analyte detecting member at the time the test is taking place. FIG. 27 shows some sizing of opening on the housing. The plug may snap into the aperture of the front end. It protects back plate and front end from blood. Clips also remove packaging. FIG. 28 shows a perspective view of a fluid sampling device having a plurality of front ends 1425 on the device that are ready for use. FIG. 28 shows that old or used front ends 1427 and new front ends 1429 may be placed on the housing. By way of example and not limitation, they may be mounted on band on a back portion of the housing. In one embodiment, the lancing is carried out in a separate operation and the surface of the finger is touched to the wicking or sip-in treated front end of the disposable "limpet" 1425. Blood is guided into the analyte detecting member channel and the test is carried out. Post testing the "limpet" front end 1425 is removed and the disk indexed before inserting the next "limpet" for the next diagnostic test. The sample acquisition channel of the limpet can be configured with mesh to guide the sample to the analyte detecting member or hydrophillically treated to guide the blood to the analyte detecting member. Since POC tests require higher amounts of blood volume the dead space for the priming of the channel leading to the not considered limiting. Limpets can be stored on board in the instrument and dispensed as a cassette. They can also be disposed of in the same cassette as used and then the entire cassette thrown way at the end of 25 or 50 patients have been tested.

In another embodiment, a fluid device is combined with analyte detecting members on a disk. The punch 400 mechanism of the lancing device can open the seal. The function f the limpet would them be to attach and for a sterility barrier on the front end, allow passage of the penetrating member through the center and perhaps contain surface treatment or mesh to guide the sample into the analyte detecting member chamber. The limpet can be configured to prevent contamination in a side-to-side aspect between analyte detecting members by forming a physical barrier between adjacent analyte detecting members. It can be configured to prevent splatter of blood on the back plane (inside of the front end) of the instrument. It may also function as a finger positioning device as it can be contoured and shaped without affecting the front face of the instrument.

Figure 29A:
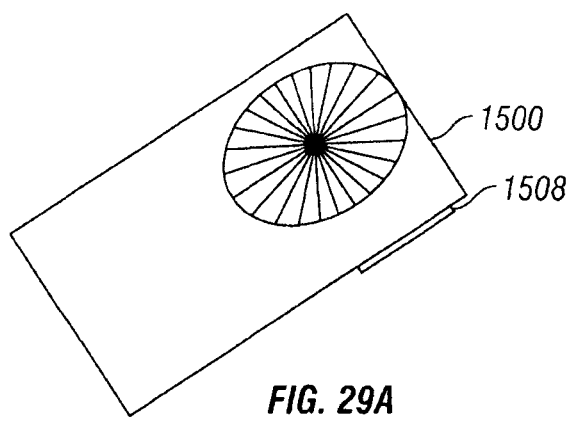
FIG. 29 shows one embodiment analyte testing strip dispenser.
Figure 29B:
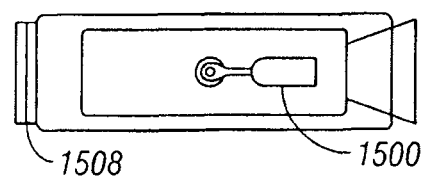

Referring now to FIG. 29, these embodiments of the present invention relate to lancing, sampling, sensing, disposable, and manufacture. In one embodiment, It is an integrated sampling I glucose-sensing system. The present invention may integrate multiple lancings with multiple electrochemical glucose sensing events. It is solved here, in some embodiments, in a very simple way by integrating the functions without integrating the two different activities (lancing and sensing) in the same physical device.

Referring again to FIG. 29, one particular simple integration of the functions of blood sampling and glucose-sensing is shown. In this embodiment, a small package of disposable glucose sensing strips 1500 in a dispenser 1508 is physically adjoined to the lancing device. In order to perform a glucose analysis, a user tears off I peels off a strip from the dispenser, sticks it to the front end of the lancing device (using suitable registration features on both the strip and the front end), and then uses the device to lance and obtain blood. The strip 1500 has many of the blood collection features, notably a woven lollipop structure to guide blood over an electrochemical glucose analyte detecting member which is an integral part of the strip (the strip is very similar in function to any glucose test strip). The front end of the lancing device may have electrode contacts which can either actively or passively make contact with the electrochemical "signal out" pads of the strip. In a particular embodiment of this concept, a hinged door be deployed from the lancing device front end to aid in registering the glucose strip and to make contact with the "signal out" pads. Following use, the disposable glucose strip is removed from the front end of the device and disposed of in the normal way.

A somewhat similar, but more integrated, approach can be utilized. In this embodiment, the glucose-sensing strips are kept physically separate from the multi-lancing elements, and are only functionally integrated. In this embodiment, the glucose-sensing strips are integrated into their own multi-strip roll. Using this multi-strip roll (in a disposable very similar to an old 110 film canister), the indexing of the penetrating member launcher can be used to move forward new, glucose strips. The glucose strips in their roll move across the front end of the fluid sampling device, and perform similarly to the strips in the concept above. The strips have registration features corresponding to registration features on the front end, and they have blood acquisition means, like a woven lollipop structure, to guide blood from the finger-lancing site to the electrochemical analyte detecting members. Contact to the "signal out" pads of the glucose test strips are accomplished by electrode contacts integral to the front end of the fluid sampling device. But in this case, there are no individual strips either to put on the front end of the fluid sampling, or to remove from the front end after use. The strips are deployed from a film canister-type disposable, and are rolled back up into a similar canister feature on the other side of the fluid sampling after use. It is clear that a multi-strip canister of this sort could be functionally integrated with a multiple penetrating member system of various forms. A multiple-strip canister may be functionally integrated with multiple penetrating members in the form of a penetrating member magazine, or a radial penetrating member disposable.

Figure 30:
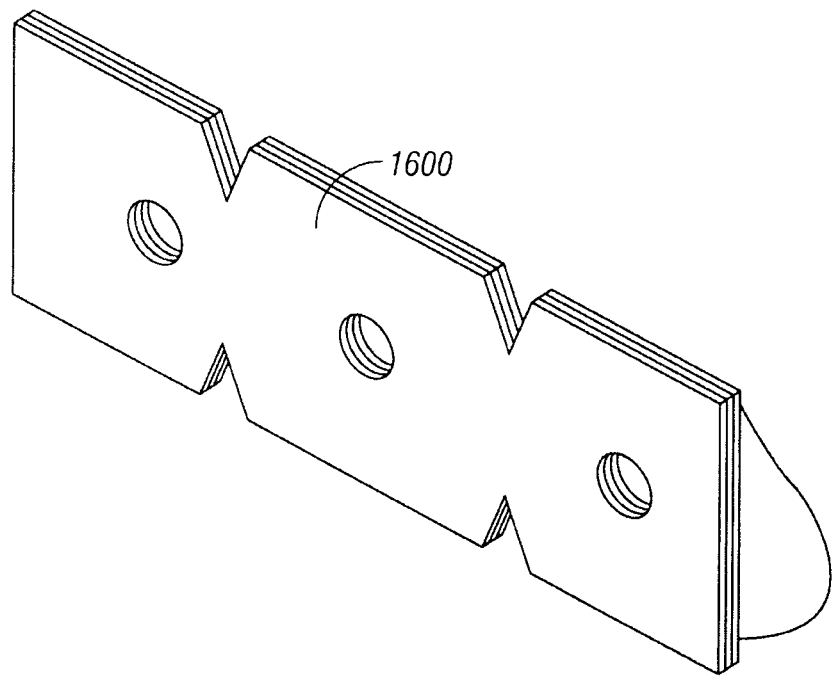
FIG. 30 through 35 shows various views of embodiments of a barrier according to the present invention.
Figure 30:
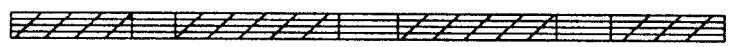
Figure 30:
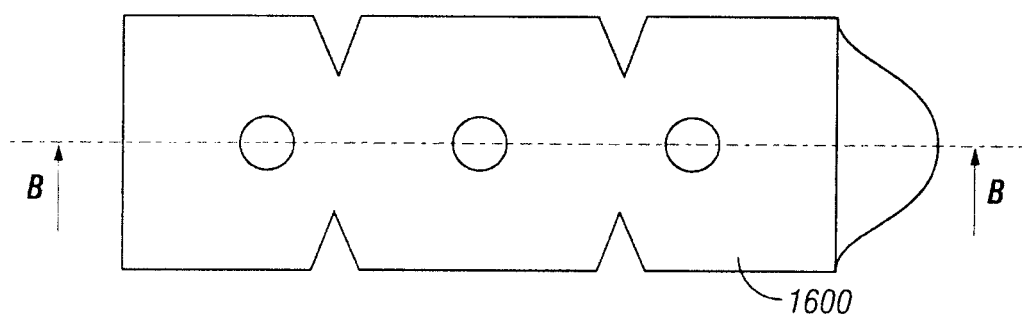

Referring now to FIG. 30, an embodiment is disclosed that relates to lancing, blood acquisition, contamination avoidance, sterile disposable materials. Most systems for gaining access to blood are single-use devices. Systems that are used to gain access to the blood of multiple people have the burden of showing that blood cannot be carried from one user to another. A means for avoiding that "blood carry-over" is the subject of this invention. That means is basically a specific material and design of tape that is used, and then discarded after use, between each patient.

Figure 31:
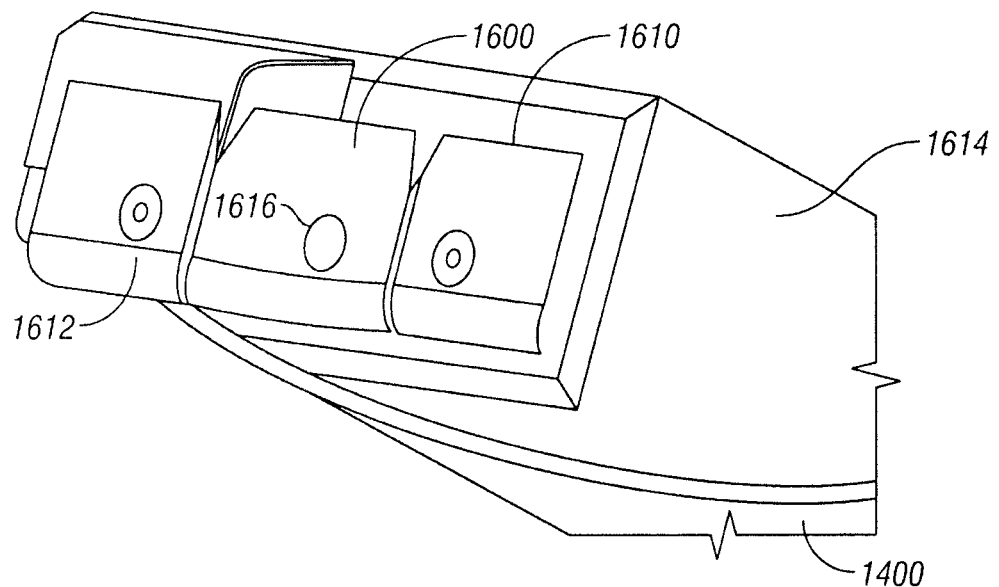

Referring now to FIG. 30, one embodiment of a sterile disposable adhesive blood barrier 1600 is to be placed between the device and the patient. The barrier 1600 may be applied to the exterior surface of the device before use with each patient and disposed of immediately after use. In the present embodiment, the adhesive blood barrier 1600 prevents contamination of any part of the device that may act as a pathway for transmission of pathogens between patients. Illustrations of the design are shown in FIG. 30 shows the barrier by itself. FIG. 31 shows the barrier 1600 attached to a fluid sampling device 1400. The barrier 1600 may have a bend relief 1610, foam offset 1612 and location features 1614 to help position the barrier properly. The port 1616 is where a penetrating member exits to piece tissue.

As seen in FIG. 31, the user applies the sterile adhesive blood barrier 1600 with foam pad to the front of the device and then place the patients' fingertip or other skin surface against the high-density foam offset pad in the firing area. The foam offset pad 1612 serves to maintain a small air gap between the patients' finger and the blood barrier film. The penetrating member then is fired through the sterile adhesive blood barrier 1600 and enters the patient before retracting back into the disposable. Testing described below has shown that the small hole created by the penetrating member, in combination with the air gap created by the foam, is highly resistant to fluid flow. The blood barrier 1600 acts effectively in preventing transfer of blood to the device despite the presence of such a hole.

In one embodiment, the selected film for the barrier 1600 is manufactured by 3M Medical Tapes and Adhesives under the catalog name "3M™ Tan 5 mil Polyethylene Medical Tape 1523, 63# Liner".

The selected foam is sold by Scapa Medical UK under the catalog name "Medifix 4005/868 Single Coated Medical Pressure Sensitive Polyurethane Foam". The offset pad is made up to the required thickness as a multi-layer laminate.

Figure 32:
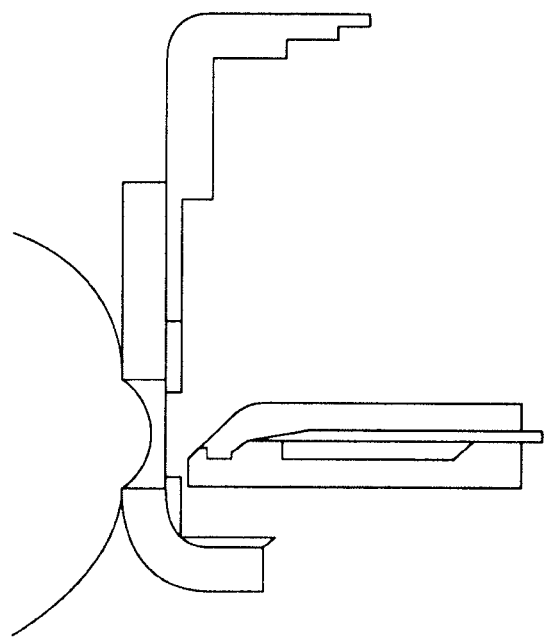

FIG. 32 is a cross-sectional diagram shows the relative dimensions of the proposed system prior to firing.

Figure 33:
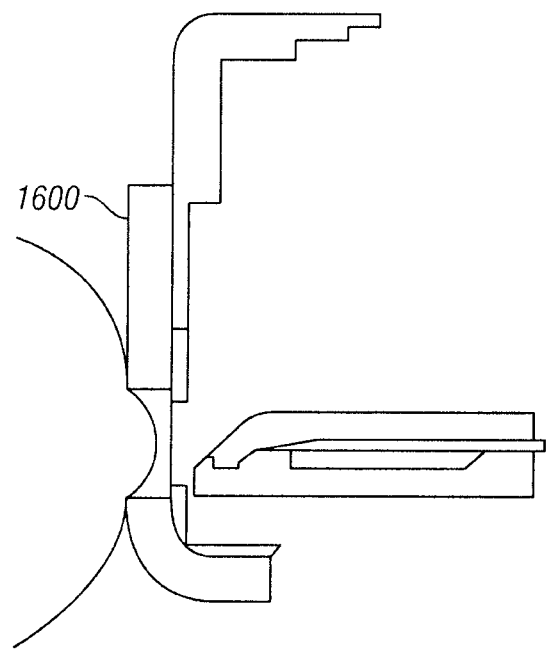
Figure 34:
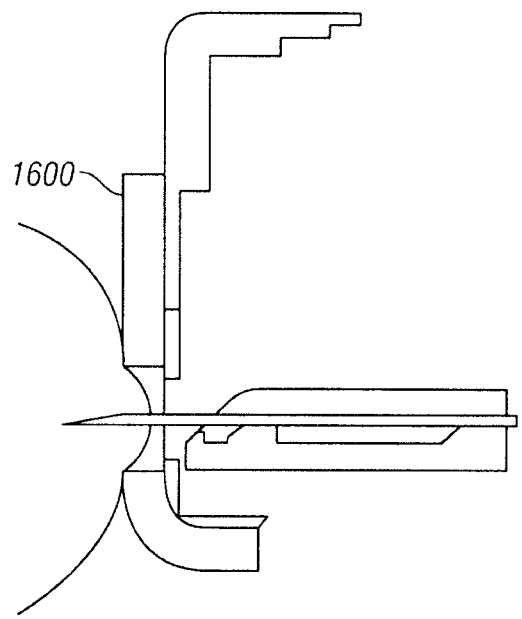
Figure 35:
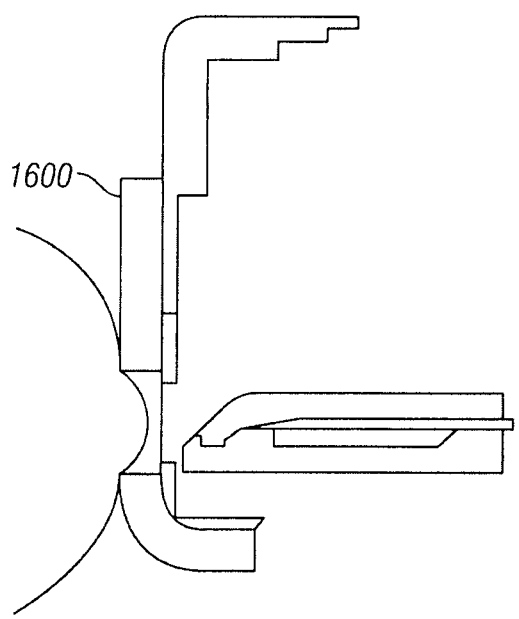

FIGS. 33, 34, and 35 are three diagrams that illustrate each phase of the lancing operation.

In this embodiment, the film and foam prevent blood being left on the casework of the device by being a simple physical barrier. In one embodiment, the blood barrier 1600 will cover nearly the entire front of the device and also wrap underneath the device. User instructions require that the user clean any obvious blood contamination that is spread outside the area of the barrier with a suitable disinfectant method.

The chief risk is that the blood will be transmitted to the device via the hole created in the barrier film by the lancing operation. The success of the design relies on the elasticity of the selected film closing the hole, the surface tension and viscosity of the blood making passage through the small hole difficult, and the air gap providing for an alternative route in which the blood pressure can be released avoiding a pressure difference across the film.

Several experiments were completed to select a film and confirm that it satisfied the requirement of preventing contamination of the device.

EXAMPLE 1

Hydrostatic Pressure Test

The objective is to test whether a suitable film and air gap could withstand a blood pressure equal to that in the capillary blood vessels of the patient after being pierced by a penetrating member.

The method that was used employed a length of tubing filled with water that was capped at one end by a piece of film intended to simulate skin. Offset from this "skin" was a sample of the film being tested. The height of the free surface of water was set to the maximum pressure likely to be transmitted to the film by the capillary bed, approximately 45 cmH20 (see below). A penetrating member was pushed through the test film and the "skin" and then slowly withdrawn whilst backlit and being filmed by a high speed macro video camera. This process was repeated for a variety of films of differing material and thickness.

The results are presented in Table 1 and it is shown that the selected film will prevent fluid transmission for pressures of at least 45 cmH20 when offset from the skin by 0.6 mm.

| Test | Film | Description | Nature of film | Pressure (cmH20) | Air Gap (mm) | Penetration (Yes/No) |
| --- | --- | --- | --- | --- | --- | --- |
| 1 | 6016/877 | 40 um PU | Hydrophilic | 9 | 0 | N |
| 2 | | | and elastic | 10 | 0 | N |
| 3 | | | | 12.5 | 0 | y |
| 4 | | | | 16 | 0 | y |
| 5 | Bioflex 140 | 25 um PU | Hydrophilic | 10 | 0 | N |
| 6 | | | and elastic | 10.5 | 0 | y |
| 7 | RX941PLT | 40 um PET | Hydrophobic | 10 | 0.6 | N |
| 8 | | | and inelastic | 16 | 0.6 | y |
| 9 | 1523 | 130 um PE | Hydrophobic | 20 | 0 | y |
| 10 | | | and elastic | 25 | 0.6 | N |
| 11 | | | | 30 | 0.6 | N |
| 12 | | | | 32 | 0.6 | N |
| 13 | | | | 45 | 0.6 | N |
| 14 | | | | 45 | 0.6 | N |

Video footage shows the elastic closure of the hole as the penetrating member is retracted. This closure reduces the area of the hole to a fraction of the penetrating member diameter increasing the resistance to fluid flow tremendously.

The elastic closure also prevents the penetrating member carrying with it large drops of blood to the device side of the barrier which might otherwise be dislodged before the penetrating member is parked safely in the disposable. As the penetrating member retracts, the film closes around it, wiping off any blood. Very small amounts of blood that may adhere to the surface of the penetrating member and be carried back to the device side of the barrier will be contained within the penetrating member cavity.

Figure 36:
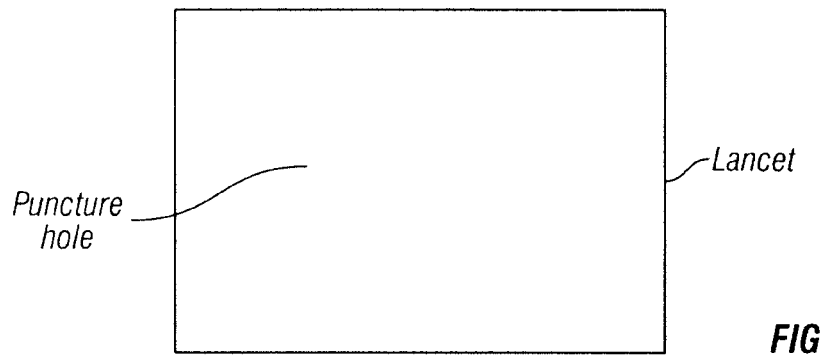
FIGS. 36 through 40 show various close-up views of areas of the barrier.

Theory governing fluid passage through a small hole states that the required driving pressure for liquid to move through a small hole is given by:

$$P = \frac{4a}{d} \qquad \text{Equation 1}$$

where: P is the driving pressure in Pa α
is the surface tension of the fluid in N/m and
d is the diameter of the hole in meters The surface tension of blood has been shown to be in the region of $56 \times 10^{-3}$ N/m. The crescent shaped hole left by the penetrating member after elastic closure is approximately $6 \times 10^{-9}$ m$^2$ in area (see "FIG. 36. Puncture hole with 0.317 mm diameter penetrating member for scale"), which is equivalent to hole with a diameter of $4.4 \times 10$-5 m. Equation 1 therefore gives a required driving pressure of 5.10 kPa. Adhesion of the blood to the sharp corners of the hole is likely to make the actual required driving pressure significantly higher than this The blood pressure in the capillary bed drops from a maximum of 30-35 mmHg at the arterial end to 12-15 mmHg at the venous end. A pressure of 30-35 mmHg equates to approximately 4.65 kPa or 45 em H20. The actual pressure witnessed by the barrier and hole is likely to be significantly lower than this due to the presence of the air gap and the resistance to flow through the outer epidermis.

Theory therefore predicts that because the actual driving pressure is less than that required, fluid flow will not occur.

EXAMPLE 2

In Vivo Test

To confirm the laboratory experimentation, the film selection by in vivo testing used a prototype device and live patient.

The barrier film and foam offset pad were applied to the prototype device. The device was then placed against the finger of the patient and fired. The barrier was inspected on the Mitutoyo after the lancing operation at 96× magnification.

The barrier film showed no transmission of blood. During this testing it was also shown that the blood is not smeared on the blood barrier and that a sufficient sample of blood is left on the patient skin for analytical testing.

Figure 37:
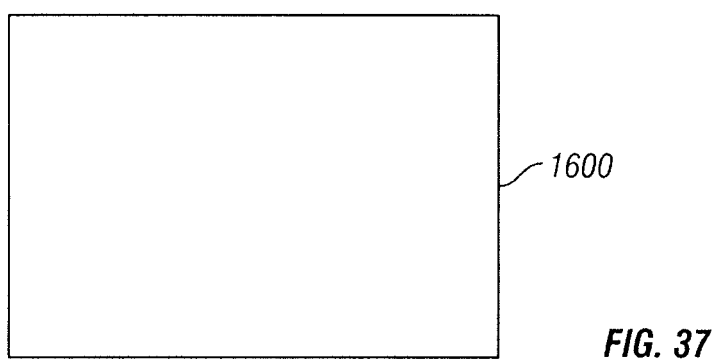
Figure 38:
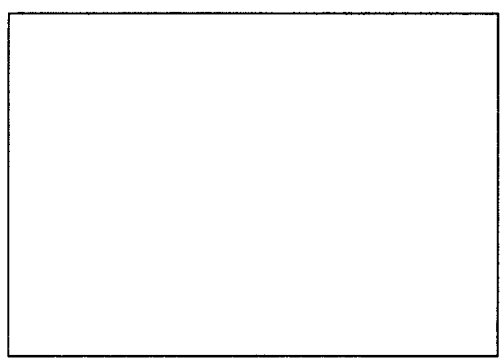
Figure 39:
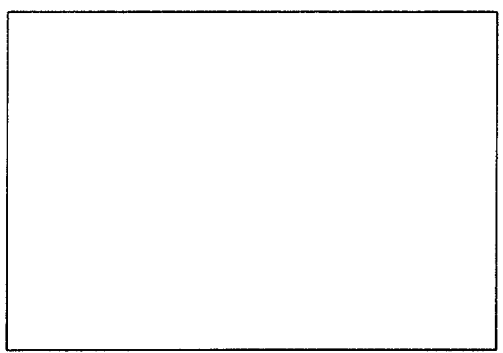
Figure 40:
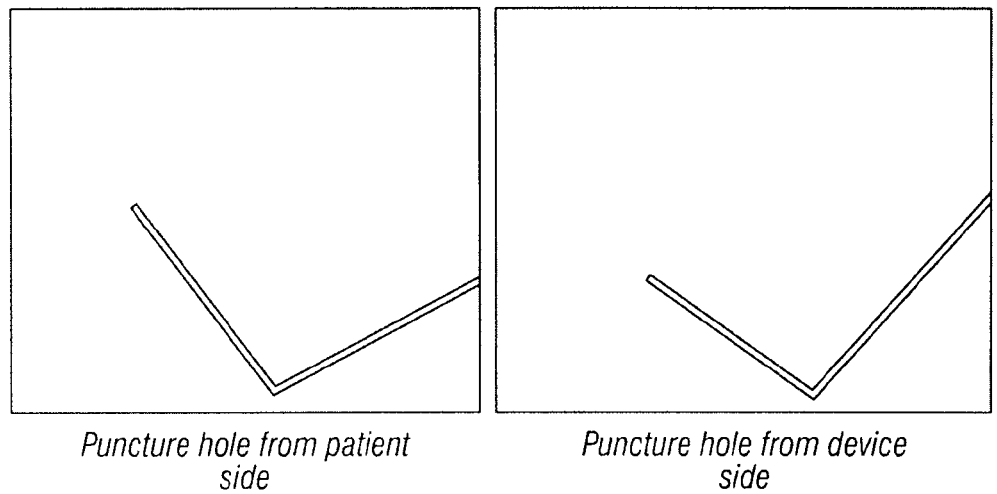

FIG. 37 shows a fluid sampling device with finger; FIG. 38 shows a blood drop on patient side of film (16×); FIG. 39 shows device side of film after firing into finger (96×).

The laboratory tests and theoretical equations support the hypothesis that the design is effective in preventing contamination of the device by blood.

EXAMPLE 3

Foreign Body Implantation

It is desirable that the penetrating member does not carry material from the adhesive blood barrier with it and implant it into the patient. The film is an elastic and ductile material being punctured by a sharpened point and it is therefore highly unlikely that pieces will be separated off and carried with the lubricated penetrating member tip. The following inspections were carried out to confirm this.

A digital photograph of the penetrating member was taken immediately after firing through the adhesive film. This inspection was made along the length of 10 penetrating members after firing through the adhesive film.

The film was inspected after firing through it.

A high frame-rate (2000 frames/second) digital video was taken of the lancing operation from the patient side.

No plastic material or adhesive was seen stuck to the penetrating member.

Inspection of the film using the Mitutoyo after piercing did not suggest that material had been removed (see "FIG. 25. Barrier film after puncture (96× magnification)").

No material removal was seen in the video footage.

Inspection of the penetrating member, the film and the process suggest that material is not removed during the firing process.

EXAMPLE 4

Sterility of the Blood Barrier

In one embodiment, the adhesive blood barrier 1600 will be prepared and packaged in a cleanroom environment and then gamma sterilized. Their respective manufacturers have declared the selected film and foam suitable for gamma sterilization. All manufacturing will be completed by an EN 13485 certified manufacturer and in accordance with that standard. The barrier film is presented to the user on a sterilized impermeable carrier and covered by another impermeable protective. The blood barrier film is then only exposed to possible contaminants once it is removed from its packaging in preparation for use. Applicator tabs and location details will be help to reduce handling of the lancing area as much as possible.

Figure 42:
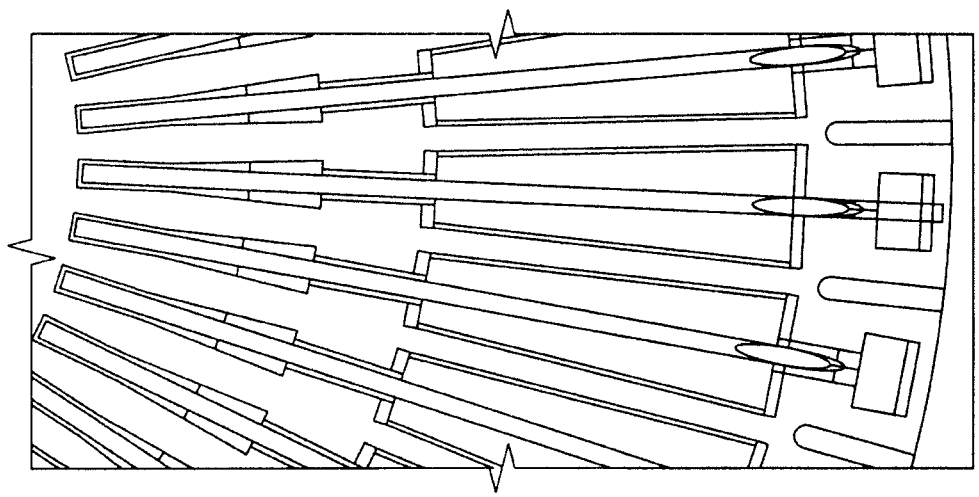
FIG. 42 shows a view of one portion of a disposable for use with the present invention.

Very small amounts of blood may adhere to the penetrating member and travel back into the disposable. Each penetrating member is contained within its own cavity that is separated from adjacent cavities and the mechanism. This separation is sufficient in size and geometry to prevent pathogens spreading. The adjacent unused sterile penetrating member is hermetically sealed up until the time of firing. FIG. 42 Plan view of part of the penetrating member disposable (protective foil not shown)" below show the layout of the disposable in which the penetrating members are contained. From these drawings it can be seen that the distance between penetrating members is large enough to prevent pathogens traveling between penetrating members even were they not sealed.

Operation of the device may be impeded and pain levels increased if the penetrating member were to be damaged by the film before it entered the patient skin. To check damage did not occur 5 penetrating members were inspected before and after a lancing operation using the device prototype. The penetrating members showed no visible damage to the sharpened tip during the firing process.

Incorrect application might place the high-density foam offset pad in the trajectory of the penetrating member or reduce the effectiveness of the foam in creating the air gap described above. To prevent such misapplication features are provided on the outer case of the fluid sampling Pro to match the geometry of the barrier film. These features make misapplication obvious and reinforce the user instructions. The features are shown in Referring to the information below, one embodiment of the instructions for users of the fluid sampling Pro Penetrating member Launcher Sterile Blood Barrier will be shown.

This device is for use by healthcare professionals only. It is recommended that the operator wear sterile gloves when using the device.

1. Prepare the skin of the patient in the area to be lanced with a sterile wipe.
2. Remove the protective covering from the packaging exposing a single item of sterile barrier film by pulling on the tab provided. Remove the sterile barrier film from the carrier by pulling on the applicator tab provided. (See illustrations below)
3. Apply the adhesive side to the front area of the device ensuring that both the outer circular holes in the barrier film fit around the matching circular bosses on the front of the device.
4. Press the sterile barrier film to the front and underside of the case taking care not to touch the firing area of the barrier film.
5. Prepare a penetrating member by operating the slider on the side of the device and depressing the fire button once. (See Lancing Device User Instructions)
6. Press the center circular cutout in the foam front of the barrier film against the patients skin in the area to be lanced.
7. Lance the patient by depressing the fire button a second time.
8. Remove the device from the patients skin and take the blood sample from their skin.
9. Carefully remove the barrier film from the front of the device using the tab provided and dispose of it properly.
10. Check that outer case of device has not been contaminated by blood and if necessary clean it with disinfectant.

Figure 41:
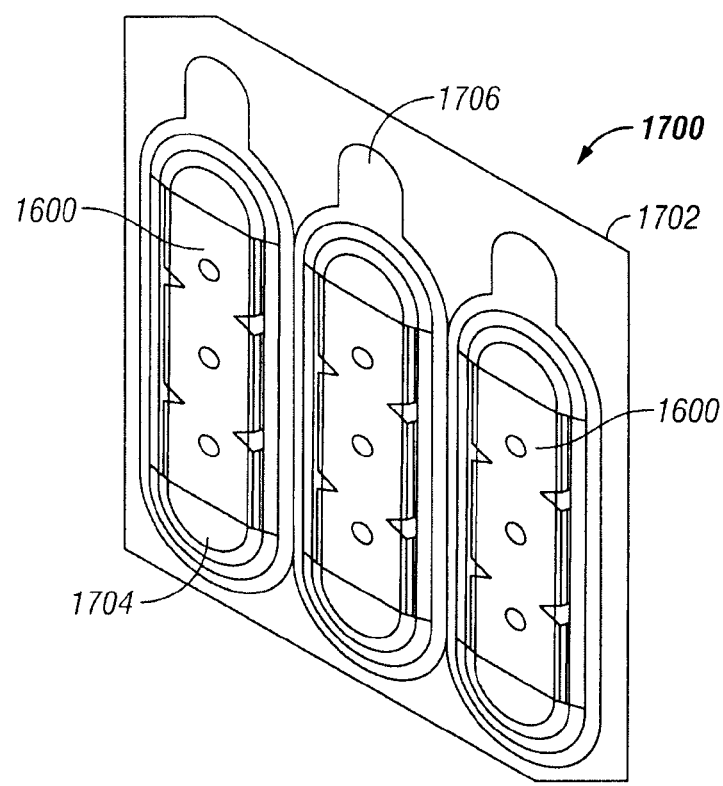
FIG. 41 shows one embodiment of packaging for use with a barrier according to the present invention.

FIG. 41 shows one embodiment of packaging for holding sterile barriers 1600. The packaging 1700 may include a sterile carrier 1702 and a protective cover 1704. Tabs 1706 may be used to facilitate pealing of the protective covers 1704.

FIG. 42 shows the possible areas of contamination and the barrier 1600 is designed to minimize the flow of blood to these areas or to prevent users from coming in to contact with any blood on these areas.

Figure 43:
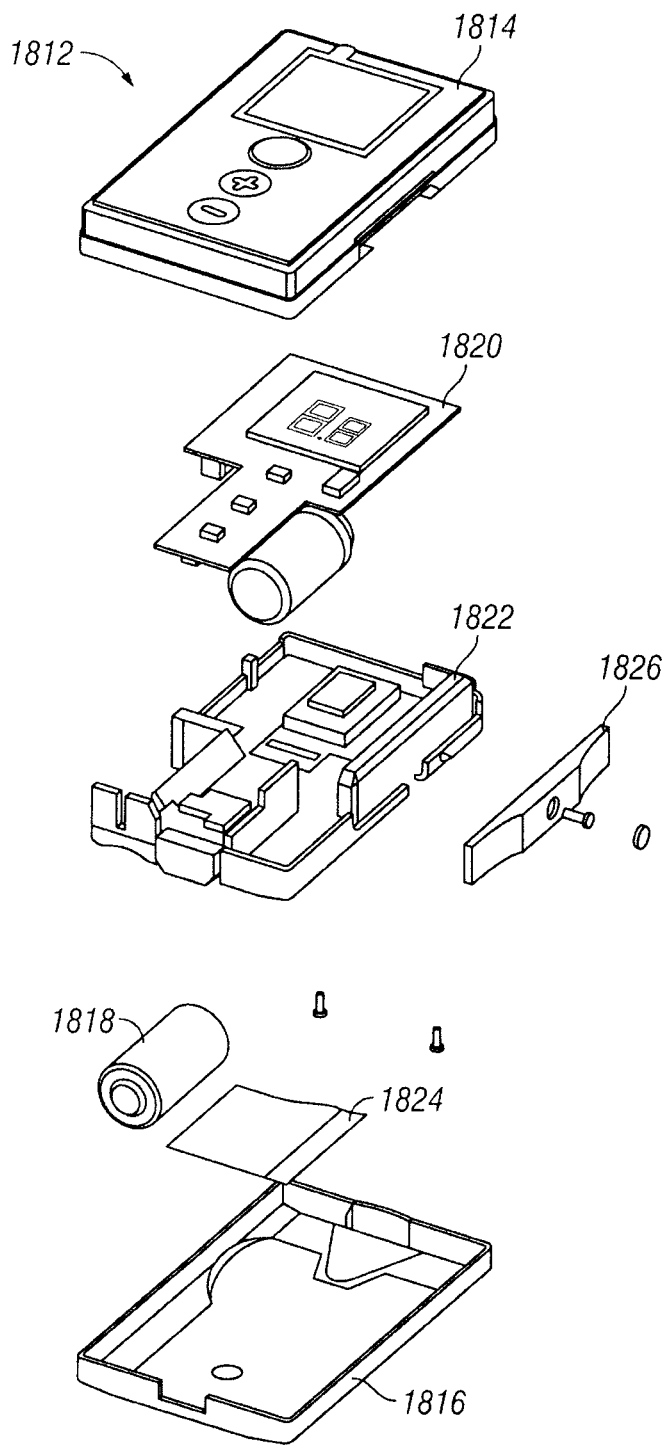
FIG. 43 is an exploded view illustrating one embodiment of a body fluid sampling device of the present invention.

In one embodiment of the present invention, illustrated in FIG. 43, the blood analyzer device 1810 includes a housing 1812 with an upper case 1814 coupled to a bottom case 1816, a battery 1818, which can be rechargeable and coupled to a recharging port, and a driver 1820. The housing 1812 can include a finger interface section. In one embodiment, the finger interface section is indented and conformable to an anatomy of a fingertip. Also included is a mechanical assembly 1822, a door assembly 1824 and a slider handle 1826.

Figure 44:
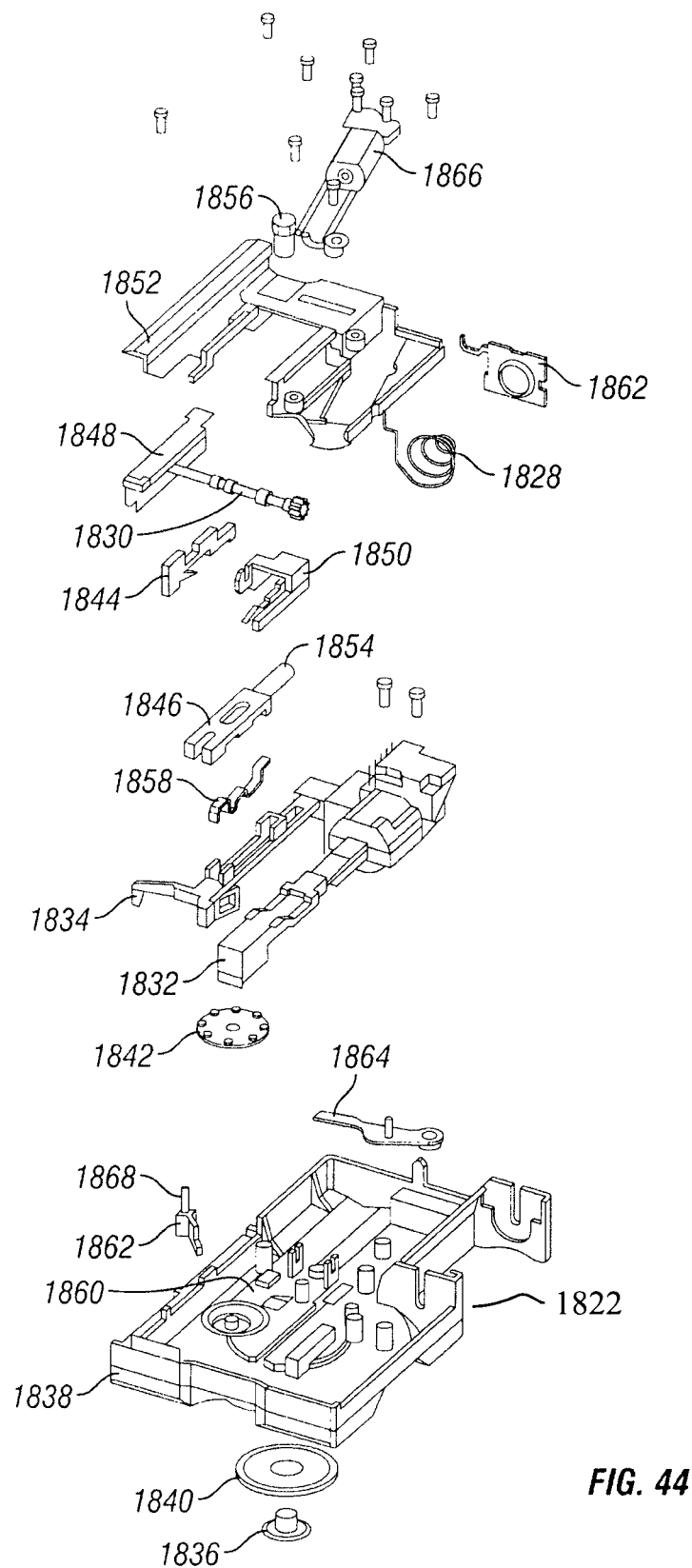
FIG. 44 is an exploded view illustrating one embodiment of a mechanical assembly of the FIG. 43 device.

As illustrated in FIG. 44, the mechanical assembly 1822 can include the following elements: a battery contact 1828, cam shaft overmold 1830, actuator assembly 1832, punch assembly 1834, bobbin retainer 1836, chassis subassembly 1838, bobbin 1840, drive gear 1842, indexer 1844, ratchet 1846, slider arm 1848, gripper stripper 1850, reaction plate 1852, ratchet tension spring 1854, disposable plunger 1856, return plate 1858, ratchet tension spring 1860, sterility barrier plunger 1862, Sweeper arm 1864, sweeper motor assembly 1866 and a sterility barrier detect spring 1868. As a non-limiting example, the return plate 1858 can be a cam follower driven by the cam shaft and slider handle 1826. The return plate 1858 drives the punch assembly 1834 that actually moves the sterility barrier seal 320. The sterility barrier seal 320 can be perforated, rolled, or folds out of a path of a launched penetrating member. A fire button is provided that launches the penetrating members.

The mechanical assembly 1822 can further include a cam actuated by the manually actuated slider handle 1826. A variety of devices can be used in place of the sweeper arm 1864, including but not limited to, a worm and sector gear, a bi-stable electromagnetic mechanism, a stepper motor, a lead screw and the like. Also provided are an insertion arm, shaft assembly, track and stripper.

A plurality of penetrating members are housed in a disposable that is positionable in the housing 1812. Each penetrating member is coupled with the driver 1820 prior to launch of a penetrating member for a lancing event. The slider handle 1826 and indexer 1844 advance the disposable and this moves penetrating members into launch positions. The battery 1818 is coupled to the driver 1820. One or more sterility barriers maintain the penetrating members in a sterile environment.

The punch assembly 1834 includes a sterility barrier opener, e.g., punch, that moves the sterility barrier out of the way of a launched penetrating member. In one embodiment, the sterility barrier opener is a punch that moves at least a portion of the sterility barrier out of a way of a launched penetrating member. The punch assembly 1834 can lift up at least a portion of the sterility barrier.

Figure 45:
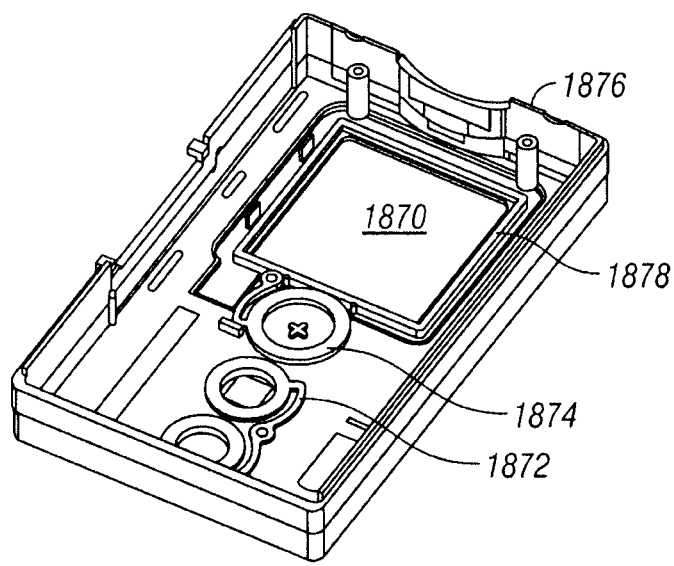
FIG. 45 illustrates one embodiment of an upper case assembly of the FIG. 43 device.
Figure 45:
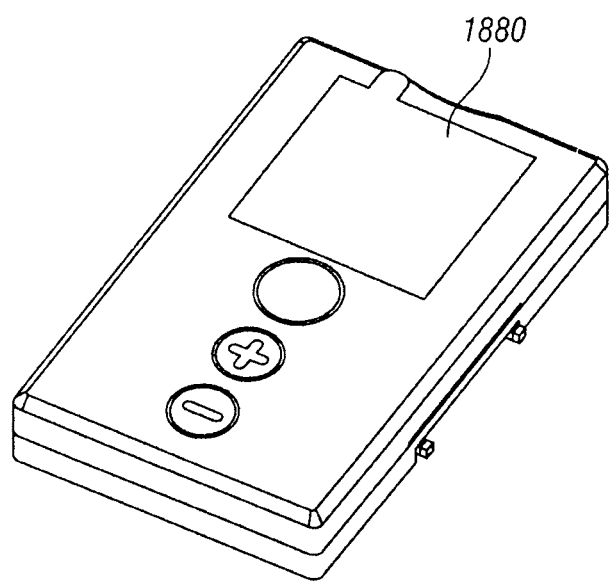

One embodiment of the upper case assembly 1014 is illustrated in FIG. 45 lin This embodiment includes, an LCD window 1870, a plus-minus button 1872, a fire button 1874, belt 1876, upper LCD gasket 1878 and a protective removeable film 1880. This film can be a standard anti-scratch cover for all plastic windows.

Figure 46:
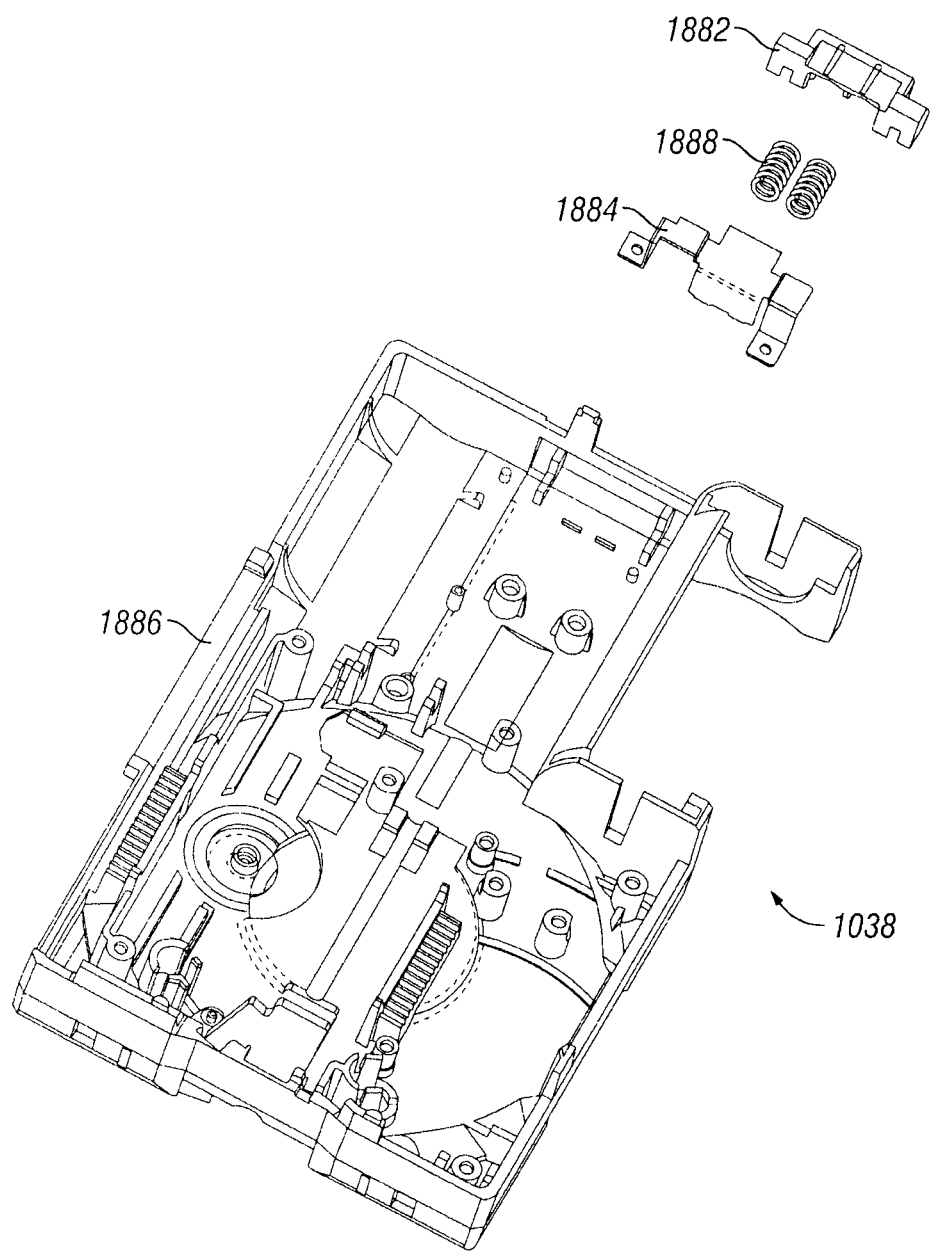
FIG. 46 illustrates one embodiment of a chassis subassembly of the FIG. 43 device.

Referring to FIG. 46, the chassis subassembly 1838 includes a door latch 1882, latch retainer 1884, chassis 1886 and a compression spring 1888

Figure 47:
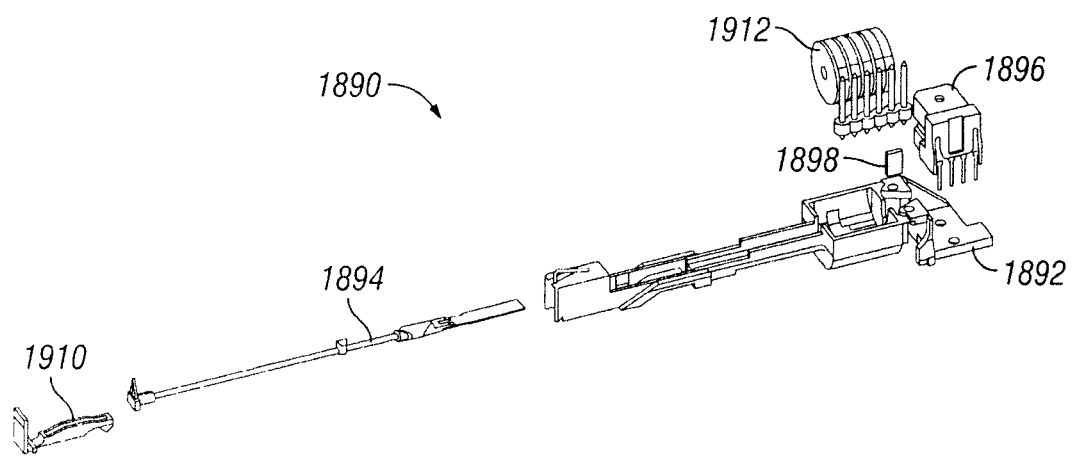
FIG. 47 illustrates one embodiment of an actuator or driver assembly of the FIG. 43 device.

Referring to the actuator assembly 1890 of FIG. 47, a gripper track 1892 is coupled to a gripper shaft assembly 1894. Also included are a sensor 1896, magnet 1898, gripper insertion arm 1910 and a solenoid sub assembly 1912. The magnet 1898 can be coupled to the sweeper arm 1864. In one embodiment, the sweeper arm 1842 and the magnet 1898 form an integrated assembly of components that include but are not limited to, the sweeper arm 1864, motor, motor mount, worm gear, sector gear, chassis, fasteners and the like. In one embodiment, the sweeper arm 1842 acts as a safety arm for penetrating members. Except during firing when in a non-blocking position, the sweeper arm 1864 physically retains the gripper shaft assembly and prevents it from accidentally exiting the housing 1812.

Figure 48:
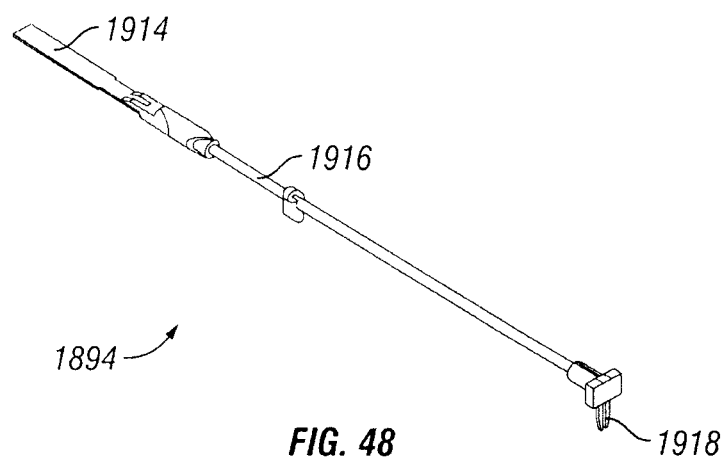
FIG. 48 illustrates one embodiment of a gripper shaft assembly of the FIG. 43 device.

The gripper shaft assembly, illustrated in FIG. 48, includes a flag 1914, gripper shaft overmold 1916. The arrow point at the carbon rod, and the plastic is overmolded around the carbon rod and the magnetic slug, as well as a stepped gripper portion 1918 that can capture and retain a penetrating member.

Figure 49:
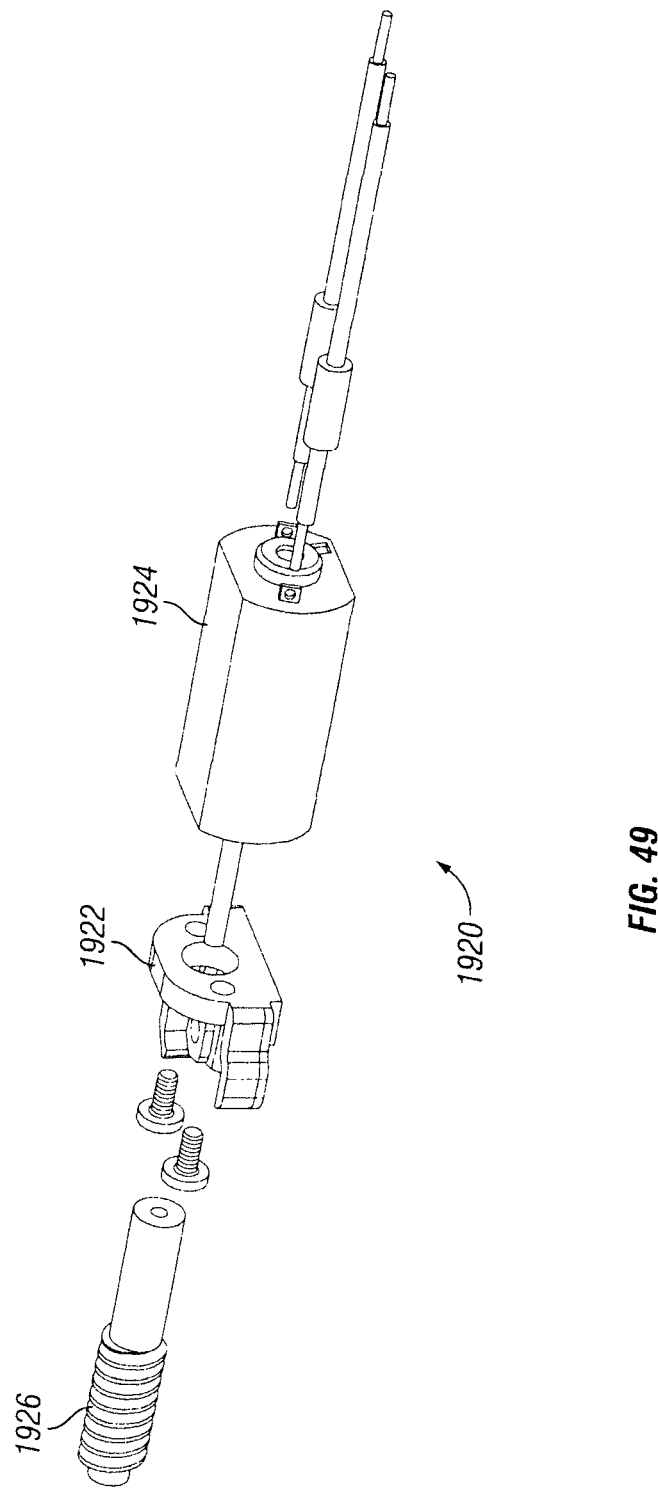
FIG. 49 illustrates one embodiment of a sweeper motor assembly of the FIG. 43 device.

The sweeper motor assembly 1920 of FIG. 49 includes a sweeper motor mount 1922, a DC motor 1924, and a sweeper worm 1926.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, the shield or other punch may be adapted for use with other disposables disclosed herein or in related applications. With any of the above embodiments, a motor may be directly coupled to rotate they cited. U.S. Provisional Application No. 60/577,412 (and U.S. Provisional Application No. 60/577,376 are fully incorporated herein by reference for all purposes.

Expected variations or differences in the results are contemplated in accordance with the objects and practices of the present invention. It is intended, therefore, that the invention be defined by the scope of the claims which follow and that such claims be interpreted as broadly as is reasonable.

The invention claimed is:

1. A blood analyzer device, comprising: a housing;
a penetrating member driver positioned in the housing; a plurality of penetrating members housed in a disposable positionable in the housing;
a gripper assembly that includes a gripper that engages a penetrating member of the plurality of penetrating members with the driver prior to launch of a penetrating member during a lancing event, an open channel that is positioned over the gripper in the gripper assembly, a gripper shaft assembly including a flag, a non-polymeric rod, a polymeric gripper shaft, a magnet and a stepped gripper portion that captures and retains a penetrating member;
an actuator assembly that includes a gripper track coupled to the gripper assembly, a sensor, and a gripper insertion arm;
a sweeper arm coupled to the gripper assembly, the sweeper arm configured to physically retain the gripper assembly and prevent it from accidentally exiting the housing; and
a power source coupled to a drive assembly and the penetrating member.

2. The device of claim 1, further comprising:
a sterility barrier that maintains the plurality of penetrating members in a sterile environment.

3. The device of claim 1, further comprising:
a mechanical assembly that includes a cam.

4. The device of claim 1, further comprising:
a sterility barrier opener that moves a sterility barrier out of the way of a launched penetrating member.

5. The device of claim 4, wherein a sterility barrier opener is a punch that moves at least a portion of the sterility barrier out of a way of a launched penetrating member.

6. The device of claim 5, wherein the punch lifts up at least a portion of the sterility barrier.

7. The device of claim 1, wherein the power source is a battery.

8. The device of claim 5, further comprising:
battery contacts.

9. The device of claim 1, further comprising:
a door assembly.

10. The device of claim 9, further comprising:
a door latch.

11. The device of claim 10, further comprising:
a door latch retainer.

12. The device of claim 1, wherein the top section of the housing includes a window.

13. The device of claim 12, further comprising:
a removable window protection film.

14. The device of claim 13, further comprising:
a display.

15. The device of claim 14, wherein the display is a liquid crystal display.

16. The device of claim 15, further comprising:
a liquid crystal display gasket positioned between the housing and the liquid crystal display.

17. The device of claim 1, wherein the housing includes a finger interface section.

18. The device of claim 17, wherein the finger interface section is indented.

19. The device of claim 18, wherein the finger interface section is conformable to an anatomy of a fingertip.

20. The device of claim 1, further comprising:
a fire button that launches penetrating members.

21. The device of claim 1, further comprising:
a slider handle.

22. The device of claim 1, further comprising:
a sterility barrier detect spring.

23. The device of claim 1, further comprising:
a sweeper arm motor assembly.

24. The device of claim 1, further comprising:
a ratchet tension spring.

25. The device of claim 1, further comprising:
an indexer.

26. The device of claim 1, further comprising:
a drive gear.

27. The device of claim 1, further comprising:
a bobbin.

28. The device of claim 1, further comprising:
a bobbin retainer.

29. The device of claim 1, further comprising:
a compression spring.

* * * * *